(12) United States Patent
Gerritz et al.

(10) Patent No.: US 7,612,069 B2
(45) Date of Patent: *Nov. 3, 2009

(54) ACYL GUANIDINES AS BETA-SECRETASE INHIBITORS

(75) Inventors: Samuel Gerritz, Guilford, CT (US); Weixu Zhai, Middletown, CT (US); Shuhao Shi, Madison, CT (US); Shirong Zhu, Cheshire, CT (US); Andrew C. Good, Wallingford, CT (US); Lorin A. Thompson, III, Higganum, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 435 days.

This patent is subject to a terminal disclaimer.

(21) Appl. No.: 11/471,125

(22) Filed: Jun. 20, 2006

(65) Prior Publication Data

US 2007/0015754 A1    Jan. 18, 2007

Related U.S. Application Data

(60) Provisional application No. 60/788,748, filed on Apr. 3, 2006, provisional application No. 60/692,600, filed on Jun. 21, 2005.

(51) Int. Cl.
*A61K 31/5377* (2006.01)
*A61K 31/55* (2006.01)
*A61K 31/416* (2006.01)
*C07D 231/12* (2006.01)

(52) U.S. Cl. .................. 514/235.5; 514/314; 514/372; 514/378; 514/406; 544/140; 546/176; 548/214; 548/248

(58) Field of Classification Search ................ None
See application file for complete search history.

(56) References Cited

U.S. PATENT DOCUMENTS 7,273,882 B2 * 9/2007 Gerritz et al. ............... 514/372

OTHER PUBLICATIONS

Jennings, L.D., et al. "Acylguanidines as Inhibitors of BACE-1: Variation of pyrrole ring substituents extending into the S1 and S3 pockets", *Abstracts of Papers*, 230th ACS National Meeting, Washington, D.C., (2005).
Hussain, I. et al., "Identification of a Novel Aspartic Protease (Asp 2) as β-Secretase", *Mol. Cell. Neurosci*, (1999) 14: 419-427.
Lin, X. et al., "Human aspartic protease memapsin 2 cleaves the β-secretase site of β-amyloid precursor protein", Proceedings of the National Academy of Sciences of the USA, (2000) 97: 1456-1460.
Luo, Y., et al., "Mice deficient in BACE1, the Alzheimer's β-secretase, have normal phenotype and abolished β-amyloid generation", *Nature Neuroscience* (2001) 4: 231-232.

Roberds, S.L. et al.,"BACE knockout mice are healthy despite lacking the primary β-secretase activity in brain: implications for Alzheimer's disease therapeutics", *Human Molecular Genetics* (2001) 10: 1317-1324.
Seiffert, D.; et al., "Presenilin-1 and -2 are molecular targets for γ-secretase inhibitors", *J. Biol. Chem.* (2000) 275, 34086-34091.
Selkoe, D. J., "Alzheimer's Disease: Genes, Proteins, and Therapy", *Physiol. Rev.* (2001) 81, 741-766.
Selkoe, D. J., "Biochemical Analyses of Alzheimer's Brain Lesions lead to the Identification of αβ and its Precursor", *Ann. Rev. Cell Biol.* (1994) 10: 374-403.
Sinha, S., et al., "Purification and cloning of amyloid precursor protein β-secretase from human brain", *Nature* (London) (1999) 402: 537-540.
Solvibile, W.R., et al., "Thiophene acyl guanidines as BACE1 Inhibitors", *Abstracts of Papers*, 230th ACS National Meeting, Washington, D.C., (2005).
Stock, J.R., et al., "Acylguanidines as small molecule BACE1 Inhibitors: Initial exploration of S1 and S2' pockets", *Abstracts of Papers*, 230th ACS National Meeting, Washington, D.C., (2005).
Sukhdeo, M.N., et al., "Acylguanidines as small molecule BACE1 Inhibitors: Optimization of the Si' region", *Abstracts of Papers*, 230th ACS National Meeting, Washington, D.C., (2005).
Thal, D. R., et al., "Two types of Sporadic Cerebral Amyloid Angiopathy", *J. Neuropath. and Exper. Neurology* (2002) 61: 282-293.
Vassar, R., et al., "β-Secretase cleavage of Alzheimer's amyloid precursor protein by the transmembrane aspartic protease BACE", *Science* (1999) 286: 735-741.
Walsh, D. M., et al., "Naturally secreted oligomers of amyloid β protein potently inhibit hippocampal long-term potentiation in vivo", *Nature* (2002) 416, 535-539.
Wolfe, M. S., "Secretase Targets for Alzheimer's Disease: Identification and Therapeutic Potential", *J. Med. Chem.* (2001) 44, 2039-2060.

(Continued)

*Primary Examiner*—Kamal A Saeed
(74) *Attorney, Agent, or Firm*—John F. Levis; Aldo A. Algieri

(57) ABSTRACT

There is provided a series of substituted acyl guanidines of Formula (I)

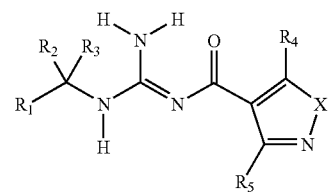

or a stereoisomer; or a pharmaceutically acceptable salt thereof, wherein $R_1$, $R_2$, $R_3$, $R_4$ and $R_5$ as defined herein, their pharmaceutical compositions and methods of use. These compounds inhibit the processing of amyloid precursor protein (APP) by β-secretase and, more specifically, inhibit the production of Aβ-peptide. The present disclosure is directed to compounds useful in the treatment of neurological disorders related to β-amyloid production, such as Alzheimer's disease and other conditions affected by anti-amyloid activity.

11 Claims, No Drawings

OTHER PUBLICATIONS

Yan, R. et al., "Membrane-anchored aspartyl protease with Alzheimer's disease β-secretase activity", *Nature* (1999) 402: 533-537.

Zhou, P., et al., "Acylguanidines as small molecule BACE1 Inhibitors: Exploration of the S1 pocket", *Abstracts of Papers*, 230th ACS National Meeting, Washington, D.C., (2005).

* cited by examiner

ACYL GUANIDINES AS BETA-SECRETASE INHIBITORS

CROSS-REFERENCE TO RELATED APPLICATIONS

This is a non-provisional application which claims the benefit of U.S. Provisional Application No. 60/788,748 filed Apr. 3, 2006 and U.S. Provisional Application No. 60/692,600 filed Jun. 21, 2005.

FIELD OF THE DISCLOSURE

This patent application provides substituted acyl guanidines having drug and bio-affecting properties, their pharmaceutical compositions and method of use. In particular, the disclosure is concerned with a series of acyl guanidines which are inhibitors of β-amyloid peptide (β-AP) production, thereby acting to prevent the accumulation of amyloid protein deposits in the brain and, therefore, are useful in the treatment of neurological disorders related to β-amyloid production. More particularly, the present disclosure relates to the treatment of Alzheimer's Disease (AD) and similar diseases.

BACKGROUND

Alzheimer's Disease is a progressive, neurodegenerative disorder characterized by memory impairment and cognitive dysfunction. AD is characterized pathologically by the accumulation of senile (neuritic) plaques, neurofibrillary tangles, amyloid deposition in neural tissues and vessels, synaptic loss, and neuronal death. It is the most common form of dementia and it now represents the third leading cause of death after cardiovascular disorders and cancer. The cost of Alzheimer's Disease is enormous (in the U.S., greater than $100 billion annually) and includes the suffering of the patients, the suffering of families, and the lost productivity of patients and caregivers. As the longevity of society increases, the occurrence of AD will markedly increase. It is estimated that more than 10 million Americans will suffer from AD by the year 2020, if methods for prevention and treatment are not found. Currently, AD is estimated to afflict 10% of the population over age 65 and up to 50% of those over the age of 85. No treatment that effectively prevents AD or reverses the clinical symptoms and underlying pathophysiology is currently available (for review see Selkoe, D. J. *Ann. Rev. Cell Biol.*, 1994, 10: 373-403).

Histopathological examination of brain tissue derived upon autopsy or from neurosurgical specimens in affected individuals reveals the occurrence of amyloid plaques and neurofibrillar tangles in the cerebral cortex of such patients. Similar alterations are observed in patients with Trisomy 21 (Down's syndrome). Biochemical and immunological studies reveal that the dominant proteinaceous component of the amyloid plaque is an approximately 4.2 kilodalton (kD) protein of about 39 to 43 amino acids. This protein is designated Aβ, β-amyloid peptide, and sometimes β/A4; referred to herein as Aβ. In addition to its deposition in amyloid plaques, Aβ is also found in the walls of meningeal and parenchymal arterioles, small arteries, capillaries, and sometimes, venules. Compelling evidence accumulated during the last decade reveals that Aβ is an internal polypeptide derived from a type 1 integral membrane protein, termed β-amyloid precursor protein (APP) (Selkoe, D. *Physiol. Rev.* 2001, 81, 741-766; Wolfe, M. *J. Med. Chem.* 2001, 44, 2039-2060). βAPP is normally produced by many cells both in vivo and in cultured cells, derived from various animals and humans. Several proteolytic fragments of APP are generated by proteinases referred to as secretases. A subset of these proteolytic fragments, designated β-amyloid peptide (Aβ), contains 39 to 43 amino acids and is generated by the combined action of β-secretase and γ-secretase. β-secretase is a membrane-bound, aspartyl protease that forms the N-terminus of the Aβ peptide. The C-terminus of the Aβ peptide is formed by γ-secretase, an apparently oligomeric complex that includes presenilin-1 and/or presenilin-2. Presenilin-1 and presenilin-2 are polytopic membrane-spanning proteins that may contain the catalytic components of γ-secretase (Seiffert, D.; Bradley, J. et al., *J. Biol. Chem.* 2000, 275, 34086-34091).

In addition to AD, excess production and/or reduced clearance of Aβ causes cerebral amyloid angiopathy (CAA) (reviewed in Thal, D., Gherbremedhin, E. et al., *J. Neuropath. Exp. Neuro.* 2002, 61, 282-293). In these patients, vascular amyloid deposits cause degeneration of vessel walls and aneurysms that may be responsible for 10-15% hemorrhagic strokes in elderly patients. As in AD, mutations in the gene encoding Aβ lead to an early onset form of CAA, referred to as cerebral hemorrhage with amyloidosis of the Dutch type, and mice expressing this mutant protein develop CAA that is similar to patients.

A logical approach to reducing Aβ levels is to interfere with the action of the secretases that are directly involved in the cleavage of APP to Aβ. The β-secretase enzyme (BACE) is responsible for cleaving APP and forms the amino-terminus of Aβ, initiating the amyloidogenic pathway. The BACE enzyme is a transmembrane aspartyl protease and was described in the literature by several independent groups [see Hussain, I. et al., (1999) *Mol. Cell. Neurosci.*, 14: 419-427; Lin, X. et al., (2000) *Proceedings of the National Academy of Sciences of the United States of America*, 97: 1456-1460; Sinha, S., et al., (1999) *Nature* (London), 402: 537-540; Vassar, R., et al., (1999) *Science* (Washington, D.C.), 286: 735-741; Walsh, D. M. et al., (2002); Wolfe, M. S. (2001); Yan, R. et al., (1999) *Nature* (London), 402: 533-537].

Removal of BACE activity in mice by gene targeting completely abolishes Aβ production [see Luo, Y., et al., (2001) *Nature Neuroscience*, 4: 231-232; Roberds, S. L. et al., (2001) *Human Molecular Genetics*, 10: 1317-1324].

BACE −/− mice also show no detectable negative phenotypes, suggesting that disruption of BACE-mediated cleavage of APP does not produce additional undesired effects. This demonstrates that a drug substance capable of inhibiting β-secretase activity should lower or halt the synthesis of Aβ and should provide a safe treatment for Alzheimer's disease.

At present there remains an urgent need to develop pharmaceutical agents capable for effective treatment in halting, slowing, preventing, and/or reversing the progression of Alzheimer's disease. Compounds that are effective inhibitors of beta-secretase, that inhibit beta-secretase mediated cleavage of APP, that are effective inhibitors of Aβ protein production by beta-secretase, and/or are effective in reducing soluble Aβ protein, amyloid beta deposits or amyloid beta plaques, are needed for effective treatment in halting, slowing, preventing, and/or reversing neurological disorders related to Aβ protein production, such as Alzheimer's disease.

SUMMARY OF THE DISCLOSURE

A series of acyl guanidine derivatives having the Formula (I)

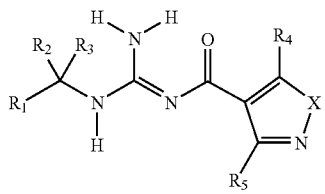

or a stereoisomer; or a pharmaceutically acceptable salt thereof, wherein $R_1$, $R_2$, $R_3$, $R_4$ and $R_5$ as defined below are effective inhibitors of the production of β-amyloid peptide (β-AP) from β-amyloid precursor protein (β-APP). The pharmacologic action of these compounds makes them useful for treating conditions responsive to the inhibition of β-AP in a patient; e.g., Alzheimer's Disease (AD) and Down's Syndrome. Therapy utilizing administration of these compounds or a pharmaceutical composition containing a therapeutically effective amount of at least one of these compounds to patients suffering from, or susceptible to, these conditions involves reducing β-AP available for accumulation and deposition in brains of these patients.

DETAILED DESCRIPTION

The present application comprises compounds of Formula I, their pharmaceutical formulations, and their use in inhibiting β-AP production in patients suffering from or susceptible to AD or other disorders resulting from β-AP accumulation in brain tissue. The compounds of Formula I which include stereoisomers and pharmaceutically acceptable salts thereof have the following formula and meanings:

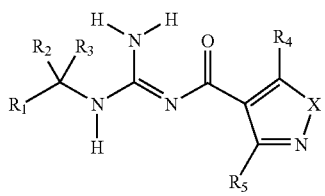

wherein
$R_1$ is naphthyl optionally substituted with halogen, quinolyl, thienyl, 2,3-dimethyl-1H-indol-5-yl, or phenyl in which said phenyl is optionally substituted with one or more groups selected from halogen, CN, $CF_3$, OH, —$NH_2$, $C_{3-6}$cycloalkyl, $C_{1-6}$alkoxy, $OR_{21}$, $C_{1-6}$alkyl optionally substituted with OH or —$NH_2$, —$(CH_2)_m$—NHC(=O)$OR_{17}$, —$(CH_2)_m$—NHC(=O)Ophenyl optionally substituted with halogen, —$(CH_2)_m$—NHC(=O)$R_{18}$, —NH(C=O)$R_{19}$, —$CH_2NH(SO_2)R_{20}$, $R_{22}$, $R_{23}$, and —$CH_2$morpholino;
$R_2$ and $R_3$ are each independently hydrogen, methyl or hydroxymethyl;
$R_4$ is hydrogen, $C_{1-6}$alkyl optionally substituted with $C_{1-4}$alkoxy or thiomethyl; or phenyl optionally substituted with one or more groups selected from halogen, $C_{1-4}$alkyl, $C_{1-4}$alkoxy, nitro and dimethylamino;

$R_5$ is hydrogen, $C_{1-6}$alkyl, or phenyl in which said phenyl is optionally substituted with one or more groups selected from halogen, —S(O)$_2$methyl, $C_{1-4}$alkyl and $C_{1-4}$alkoxy;
X is O, S, NH or $NHCH_3$;
m is 0 or 1;
$R_{17}$ is $C_{1-6}$ alkyl optionally substituted with $C_{1-4}$alkoxy, halogen, $C_{2-3}$alkynyl, 4-nitrophenyl, benzyloxy or benzothiophene 1,1-dioxide;
$R_{18}$ is $C_{1-6}$alkyl or $C_{3-6}$cycloalkyl in which each is optionally substituted with a group selected from halogen, CN, $CF_3$, —$N(CH_3)_2$, $C_{1-4}$alkoxy, $C_{3-6}$cycloalkyl, morpholino, thienyl, imidazolyl, pyridyl, azepinyl, benzothienyl, benzofuranyl, phenyl and methoxyphenyl;
$R_{19}$ is $C_{1-6}$alkyl optionally substituted with methoxyethyloxy or methylthio; $C_{1-4}$alkoxy optionally substituted with halogen; $C_{3-6}$cycloalkyl, phenyl, pyridyl optionally substituted with one or two halogen and $C_{1-4}$alkyl; benzothienyl, 1-methyl-2-pyrrolyl or furanyl;
$R_{20}$ is $C_{1-6}$alkyl, 1,2-dimethyl-1H-imidazolyl, thienyl or phenyl in which said phenyl is optionally substituted with a group selected from acetyl, $C_{1-4}$alkoxy, benzyloxy, halogen, NH(C=O)$CH_3$ and nitro;
$R_{21}$ is $C_{1-6}$alkyl optionally substituted with a group selected from $C_{1-4}$alkoxy, halogen, phenyl, furanyl and methylamino;
$R_{22}$ is —CH=CH-phenyl or —CH=CH—$C_{1-4}$alkyl optionally substituted with $C_{1-4}$alkoxy or OH; and
$R_{23}$ is pyridyl, thienyl, $C_{2-6}$alkenyl, or phenyl optionally substituted with halogen;

or a nontoxic pharmaceutically acceptable salt thereof.

The present application also provides a method for the treatment or alleviation of disorders associated with β-amyloid peptide, especially Alzheimer's Disease, cerebral amyloid angiopathy and Down's Syndrome, which comprises administering together with a conventional adjuvant, carrier or diluent a therapeutically effective amount of a compound of Formula (I) or a pharmaceutically acceptable salt thereof.

As used herein, the term "Aβ" denotes the protein designated Aβ, β-amyloid peptide, and sometimes β/A4, in the art. Aβ is an approximately 4.2 kilodalton (kD) protein of about 39 to 43 amino acids found in amyloid plaques, the walls of meningeal and parenchymal arterioles, small arteries, capillaries, and sometimes, venules. The isolation and sequence data for the first 28 amino acids are described in U.S. Pat. No. 4,666,829. The 43 amino acid sequence is well known in the art, see Colin Dingwall, *Journal of Clinical Investigation*, November 2001, 108 (9): 1243-1246; as well as PCT international patent application WO 01/92235, published Dec. 6, 2001, herein incorporated by reference in its entirety.

The term "APP", as used herein, refers to the protein known in the art as β amyloid precursor protein. This protein is the precursor for Aβ and through the activity of "secretase" enzymes, as used herein, it is processed into Aβ. Differing secretase enzymes, known in the art, have been designated β secretase, generating the N-terminus of Aβ, α secretase cleaving around the 16/17 peptide bond in Aβ, and "γ secretases", as used herein, generating C-terminal Aβ fragments ending at position 38, 39, 40, 42, and 43 or generating C-terminal extended precursors which are subsequently truncated to the above polypeptides.

The term "substituted," as used herein and in the claims, means that any one or more hydrogens on the designated atom is replaced with a selection from the indicated group, provided that the designated atom's normal valency is not exceeded, and that the substitution results in a stable compound.

As used herein and in the claims, "alkyl" or "alkylene" is intended to include both branched and straight-chain saturated aliphatic hydrocarbon groups having the specified number of carbon atoms; for example, "$C_{1-6}$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, pentyl, 3-methylbutyl, hexyl and the like. Preferred "alkyl" group, unless otherwise specified, is "$C_{1-4}$ alkyl". Additionally, unless otherwise specified, "propyl" denotes n-propyl or i-propyl; "butyl" denotes n-butyl, i-butyl, sec-butyl, or t-butyl.

As used herein and in the claims, "alkenyl" or "alkenylene" is intended to include hydrocarbon chains of either a straight or branched configuration and one or more unsaturated carbon-carbon bonds which may occur in any stable point along the chain, for example, "$C_{2-6}$ alkenyl" include but are not limited to ethenyl, 1-propenyl, 2-propenyl, 1-butenyl, 2-butenyl, 3-butenyl, 3-methyl-2-butenyl, 2-pentenyl, 3-pentenyl, hexenyl, and the like.

As used herein and in the claims, "alkynyl" or "alkynylene" is intended to include hydrocarbon chains of either a straight or branched configuration and one or more carbon-carbon triple bonds which may occur in any stable point along the chain, for example, "$C_{2-6}$ alkynyl" include but not limited to ethynyl, 1-propynyl, 2-propynyl, 1-butynyl, 2-butynyl, 3-butynyl, and the like.

"Alkoxy" or "alkyloxy" represents an alkyl group as defined above with the indicated number of carbon atoms attached through an oxygen bridge. Examples of "$C_{1-6}$alkoxy" include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

As used herein and in the claims, "halogen" refers to fluoro, chloro, bromo, and iodo. Unless otherwise specified, preferred halogens are fluoro and chloro. "Counterion" is used to represent a small, negatively charged species such as chloride, bromide, hydroxide, acetate, sulfate, and the like.

"Cycloalkyl" is intended to include saturated ring groups, having the specified number of carbon atoms. For example, "$C_{3-6}$ cycloalkyl" denotes such as cyclopropyl, cyclobutyl, cyclopentyl and cyclohexyl.

The compounds described herein may have asymmetric centers. It is understood, that whether a chiral center in an isomer is "R" or "S" depends on the chemical nature of the substituents of the chiral center. All configurations of compounds of the invention are considered part of the invention. Additionally, the carbon atom to which $R_2$ and $R_3$ is attached may describe a chiral carbon. Compounds of the present disclosure containing an asymmetrically substituted atom may be isolated in optically active or racemic forms. It is well known in the art how to prepare optically active forms, such as by resolution of racemic forms or by synthesis from optically active starting materials. Mixtures of isomers of the compounds of the examples or chiral precursors thereof can be separated into individual isomers according to methods which are known per se, e.g. fractional crystallization, adsorption chromatography or other suitable separation processes. Resulting racemates can be separated into antipodes in the usual manner after introduction of suitable salt-forming groupings, e.g. by forming a mixture of diastereosiomeric salts with optically active salt-forming agents, separating the mixture into diastereomeric salts and converting the separated salts into the free compounds. The enantiomeric forms may also be separated by fractionation through chiral high pressure liquid chromatography columns. Many geometric isomers of olefins and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein and in the claims, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

In the method of the present application, the term "therapeutically effective amount" means the total amount of each active component of the method that is sufficient to show a meaningful patient benefit, i.e., healing of acute conditions characterized by inhibition of β-amyloid peptide production. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases associated with β-amyloid peptide.

The compounds of the present application can be prepared in a number of ways well known to one skilled in the art of organic synthesis. The compounds of the present application can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The compounds may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Compounds of formula I are prepared as illustrated in Scheme 1. Treatment of commercially available PS-Wang-p-nitrophenyl carbonate resin (III) with S-methylthiourea to afford solid-supported intermediate of formula IIIa. Intermediate of formula IIIa are treated with intermediates of formula IV and an amide-bond forming reagent (e.g. diisopropylcarbodiimide) to provide solid-supported intermediates of formula V. Intermediates of formula IV can be obtained commercially, can be prepared by methods known in the literature, or can be readily prepared by one skilled in the art. Intermediates of formula V are treated with intermediates of formula VI to afford solid-supported intermediates of formula VII. Intermediates of formula VI can be obtained commercially, can be prepared by methods known in the literature, or can be readily prepared by one skilled in the art. Treatment of intermediates of formula VII with trifluoroacetic acid (TFA) will cleave the product from the solid support and provide compounds of formula I.

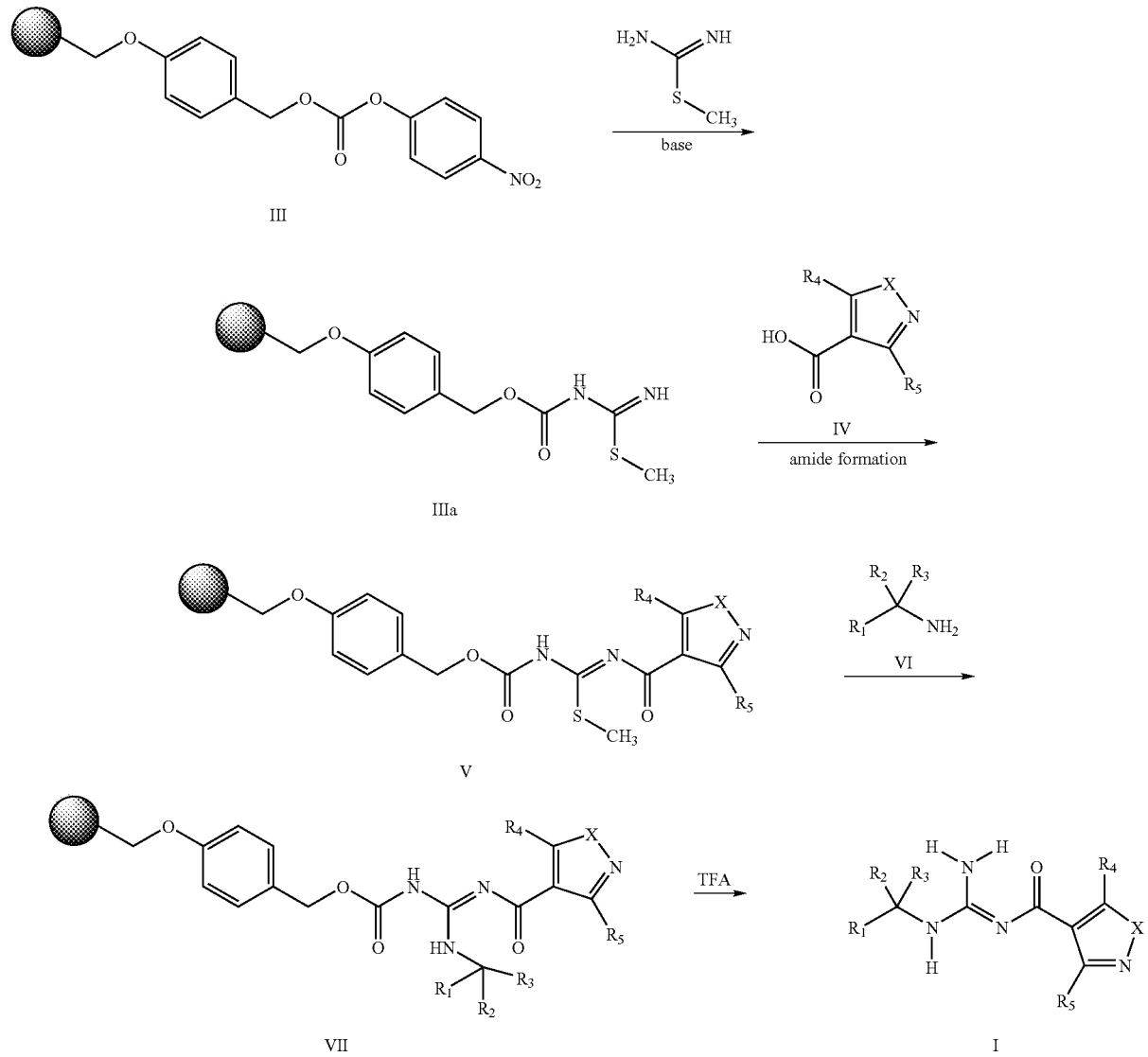

Scheme 1

Scheme 2

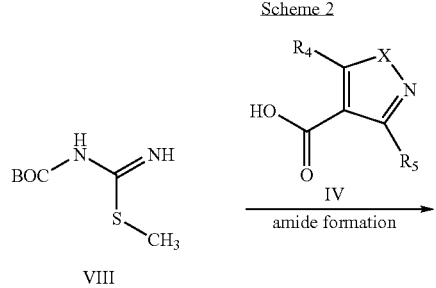

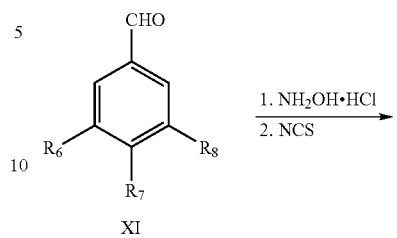

Scheme 3

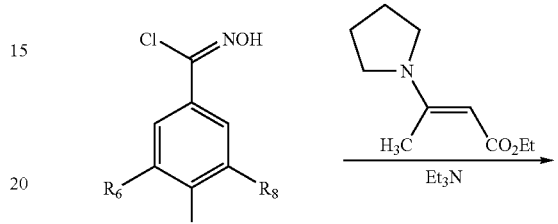

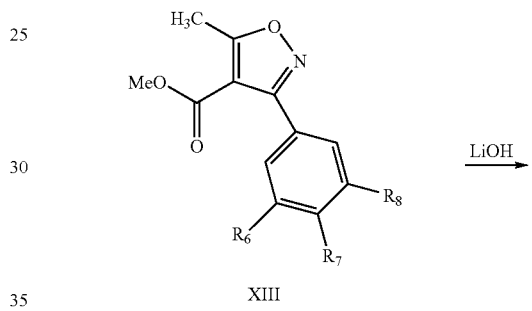

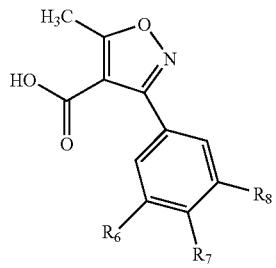

Alternatively, compounds of formula I are prepared as illustrated in Scheme 2. Intermediate of formula VIII is treated with intermediates of formula IV and an amide-bond forming reagent (e.g. diisopropylcarbodiimide) to provide intermediates of formula IX. Intermediate of formula VIII can be prepared by analogy to methods known in the literature (See: Yuan, C.; Williams, R. M. *Tetrahedron Lett.* 1996, 37, 1945-1948). Intermediates of formula IV can be obtained commercially, can be prepared by methods known in the literature, or can be readily prepared by one skilled in the art. Intermediates of formula IX are treated with intermediates of formula VI to afford intermediates of formula X. Intermediates of formula VI can be obtained commercially, can be prepared by methods known in the literature, or can be readily prepared by one skilled in the art. Treatment of intermediates of formula X with trifluoroacetic acid (TFA) removes the BOC protecting group and provides compounds of formula I.

Compounds of formula IVa are prepared as outlined in Scheme 3 and as described in the literature. [See: Gerald W. Zamponi, Stephanie C. Stotz, Richard J. Staples, Tina M. Andro, Jared K. Nelson, Victoria Hulubei, Alex Blumenfeld, and Nicholas R. Natale, J. Med. Chem., 2003, 46, 87-96.] Sequential treatment of benzaldehyde derivatives of formula XI with hydroxylamine hydrochloride, then N-chlorosuccinimide provides intermediates of formula XII. Benzaldehyde derivatives of formula XI can be obtained commercially, can be prepared by methods known in the literature, or can be readily prepared by one skilled in the art. Intermediates of formula XIII are prepared by treatment of chlorooximes of formula XII with (E)-ethyl 3-(pyrrolidin-1-yl) but-2-enoate to afford isoxazoles of formula XIII. Hydrolysis of the methyl ester of isoxazoles of formula XIII affords compounds of formula IVa.

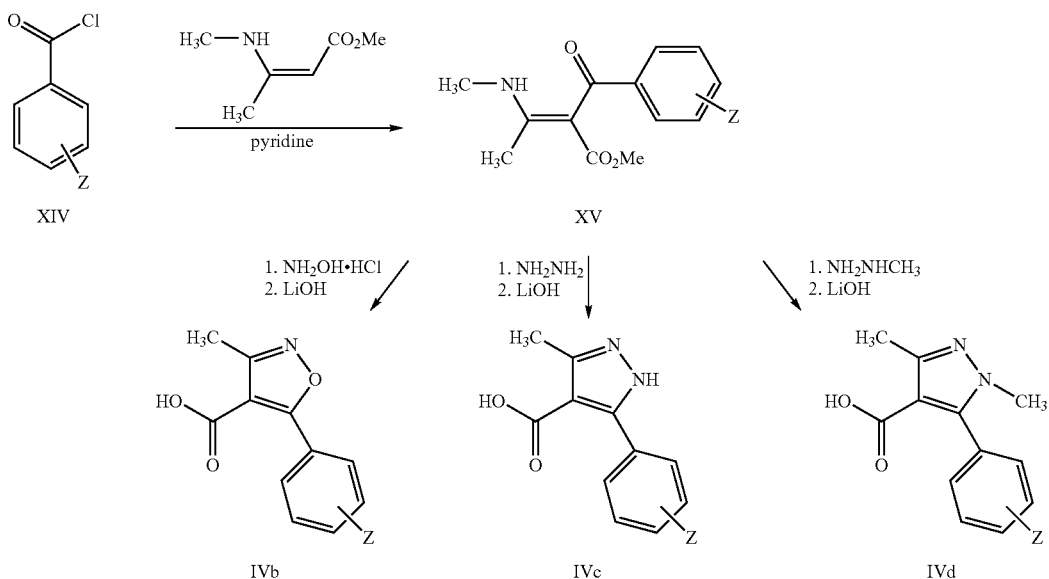

Compounds of formula IVb, IVc, and IVd in which Z represents art-recognized phenyl substituents are prepared from common intermediate XV as outlined in Scheme 4 and as described in the literature. [See: Ratheke, M. W.; Cowan, P. J. Org. Chem., 1985, 50, 2622.] Treatment of acid chlorides of formula XIV with (Z)-methyl 3-(methylamino) but-2-enoate provides intermediates of formula XV. Compounds of formula IVb are prepared by sequential treatment of intermediates of formula XV with hydroxylamine hydrochloride then lithium hydroxide. Compounds of formula IVc are prepared by sequential treatment of intermediates of formula XV with hydrazine then lithium hydroxide. Compounds of formula IVd are prepared by sequential treatment of intermediates of formula XV with methylhydrazine then lithium hydroxide.

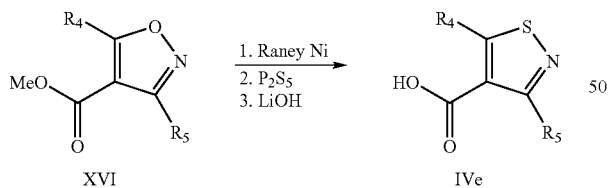

Compounds of formula IVe are prepared from intermediates of formula XVI as outlined in Scheme 5. (D. N. McGregor, U. Corbin, J. E. Swigor, and L. C. Cheney., Tetrahedron, 1969, 25, 389-395). Intermediate isooxazoles of formula XVI are treated with Raney Ni, then $P_2S_5$ to afford the corresponding isothiazole which upon hydrolysis with LiOH provides compounds of formula IVe. Intermediates of formula XVI can be obtained commercially, can be prepared as outlined in Schemes 3 and 4, or can be readily prepared by one skilled in the art.

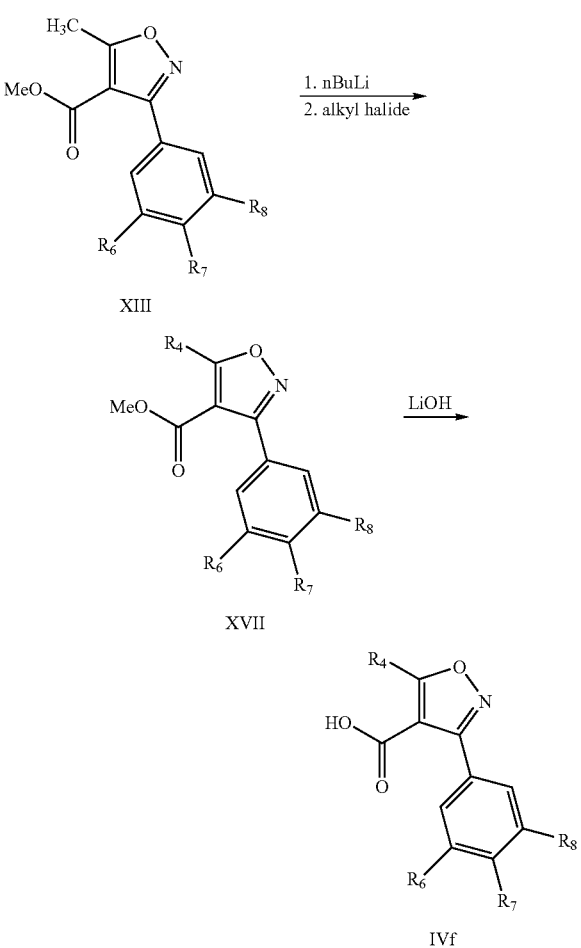

Compounds of formula IVf are prepared from intermediates of formula XIII as outlined in Scheme 6 and as described in the literature. [See: N. R. Natale, John I. McKenna, Chorng-Shyr Niou, and Mark Borth, J. Org. Chem., 1985, 50, 5660.] Intermediate isooxazoles of formula XIII are treated with nBuLi, then alkyl halides to afford intermediates of formula XVII. Alkyl halides can be obtained commercially, can be prepared by methods known in the literature, or can be readily prepared by one skilled in the art. Treatment of intermediates of formula XVII with LiOH can provide compounds of formula IVf.

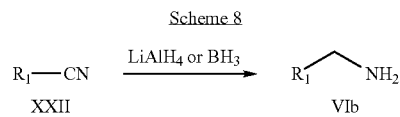

Compounds of formula VIb are also prepared from nitrile-containing intermediates of formula XXII as outlined in Scheme 8. Treatment of intermediates of formula XXII with strong hydride-based reducing agents such as lithium aluminum hydride or borane provides compounds of formula VIb.

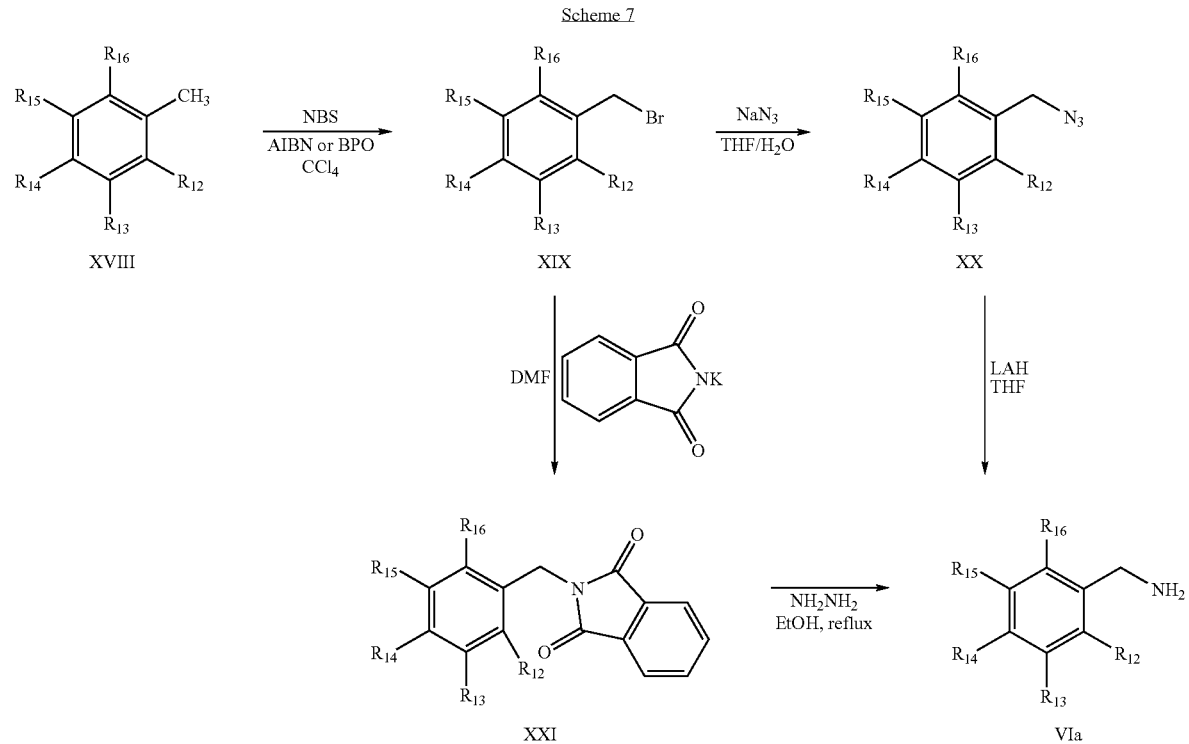

Compounds of formula VIa are prepared from intermediates of formula XVIII as outlined in Scheme 7. Treatment of intermediates of formula XVIII with N-bromosuccinimide in the presence of a radical initiator (AIBN or benzoylperoxide) provides intermediates of formula XIX. Intermediates of formula XVIII can be obtained commercially, can be prepared by methods known in the literature, or can be readily prepared by one skilled in the art. Intermediates of formula XIX are converted to compounds of formula VIa via two routes. In the first route, intermediates of formula XIX are treated with sodium azide to provide intermediates of formula XX, which upon treatment with lithium aluminum hydride affords compounds of formula VIa. Alternatively, intermediates of formula XIX are treated with the potassium salt of phthalimide to provide intermediates of formula XXI, which upon treatment with hydrazine affords compounds of formula VIa.

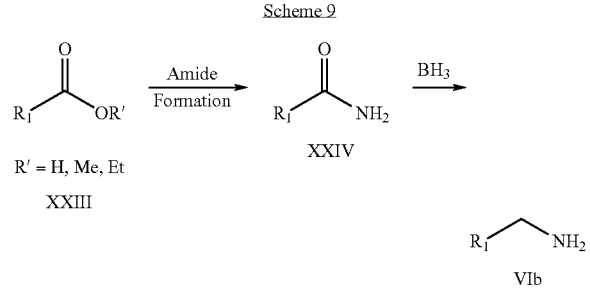

Compounds of formula VIb are also prepared from carboxylic acid derivatives of formula XXIII as outlined in Scheme 9. Treatment of intermediates of formula XXIII with ammonia under typical amide bond formation conditions affords intermediates of formula XXIV, which upon treatment with strong hydride-based reducing agents such as borane provides compounds of formula VIb.

Scheme 10

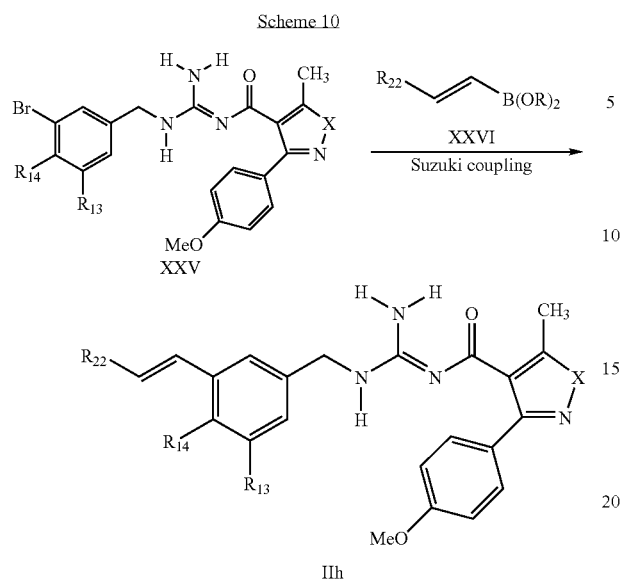

Bromo-substituted compounds of formula XXV are transformed into compounds of formula IIh as described in Scheme 10. Intermediates of formula XXV are treated with boronic acid intermediates of formula XXVI and a palladium-based reagent to afford compounds of formula IIh. Intermediates of formula XXV are prepared via either of the synthetic routes outlined in Schemes 1 and 2. Intermediates of formula XXVI can be obtained commercially, can be prepared by methods known in the literature, or can be readily prepared by one skilled in the art.

Scheme 11

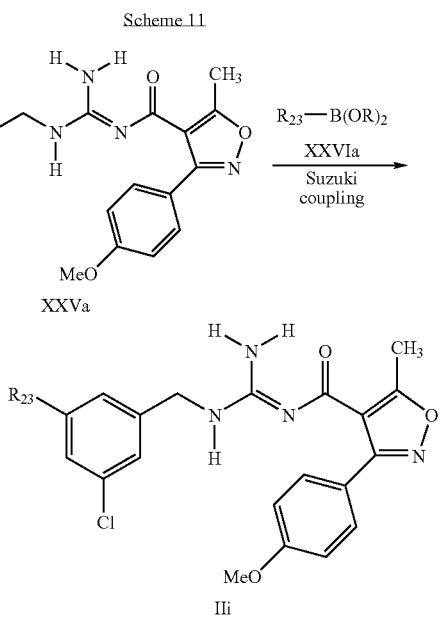

Bromo-substituted compounds of formula XXVa are transformed into compounds of formula IIi as described in Scheme 11. Intermediates of formula XXVa are treated with boronic acid intermediates of formula XXVIa and a palladium-based reagent to afford compounds of formula IIi. Intermediates of formula XXVa are prepared via either of the synthetic routes outlined in Schemes 1 and 2. Intermediates of formula XXVIa can be obtained commercially, can be prepared by methods known in the literature, or can be readily prepared by one skilled in the art.

Scheme 12

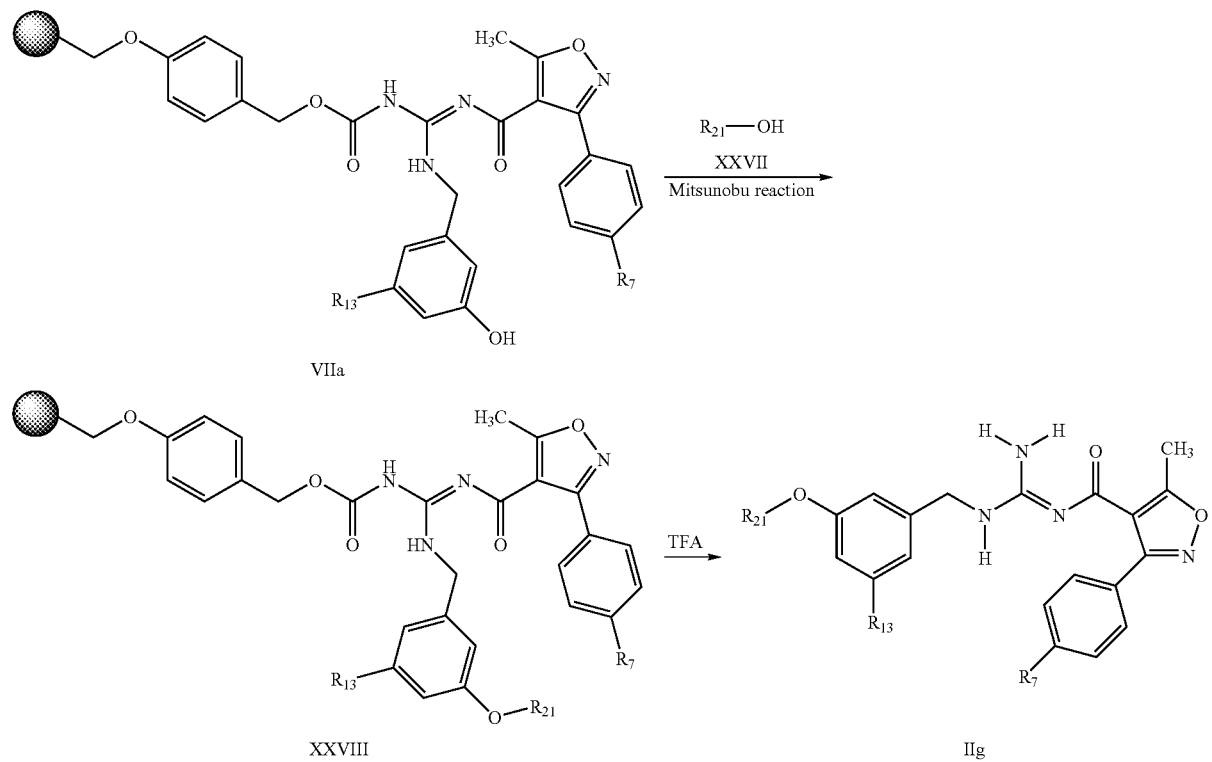

Compounds of formula IIg can be prepared as described in Scheme 12. Solid-supported intermediates of formula VIIa are treated with alcohols of formula XXVII and the appropriate reagents for a Mitsunobu reaction to afford solid supported intermediates of formula XXVIII. Intermediates of formula VIIa can be prepared via the synthetic route outlined in Scheme 1. Alcohols of formula XXVII can be obtained commercially, can be prepared by methods known in the literature, or can be readily prepared by one skilled in the art. Treatment of solid supported intermediates of formula XXVIII with TFA provides compounds of formula IIg.

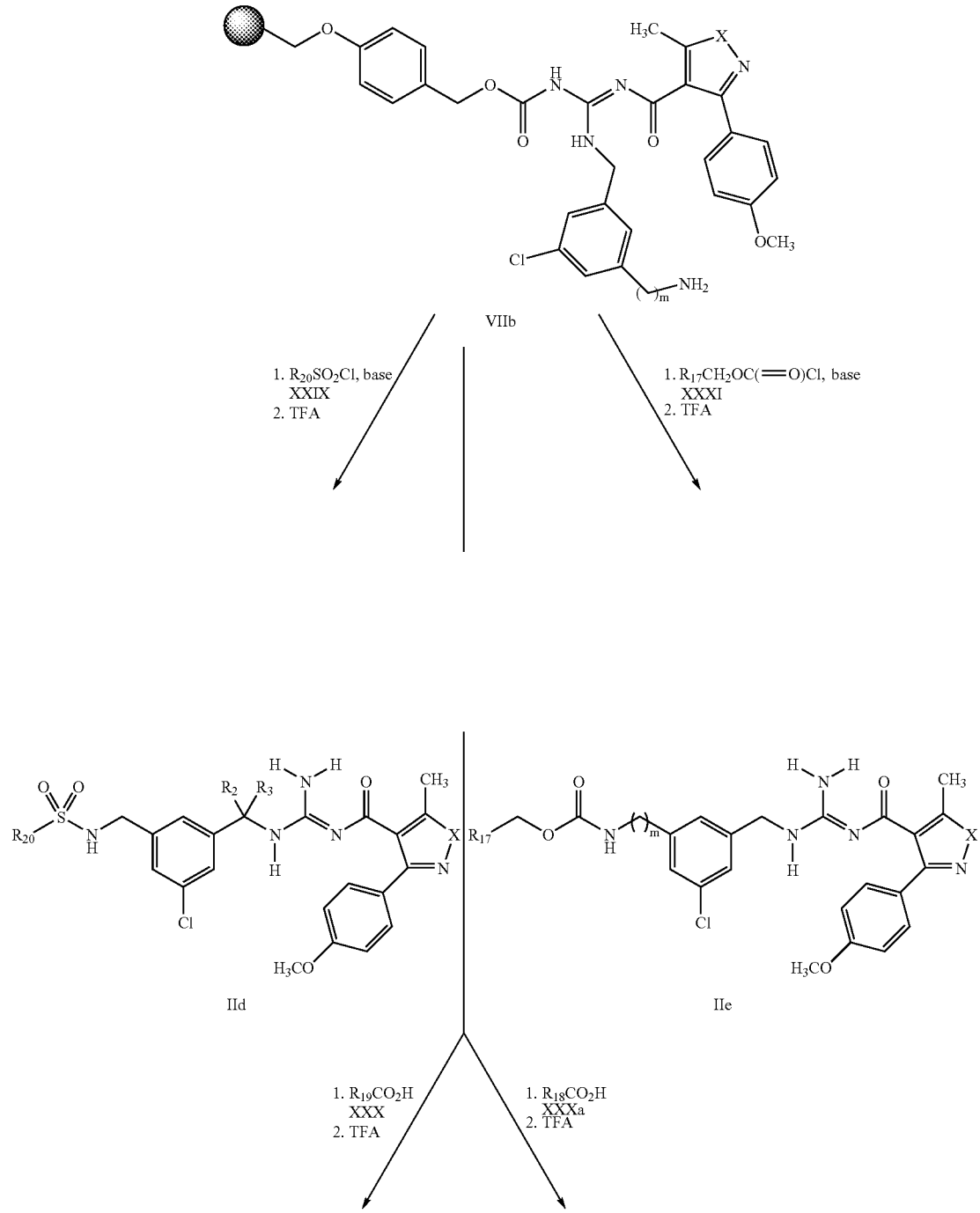

-continued

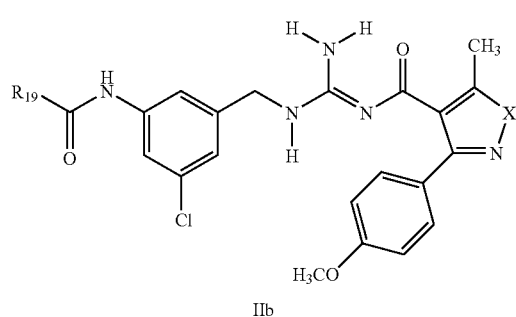

IIb

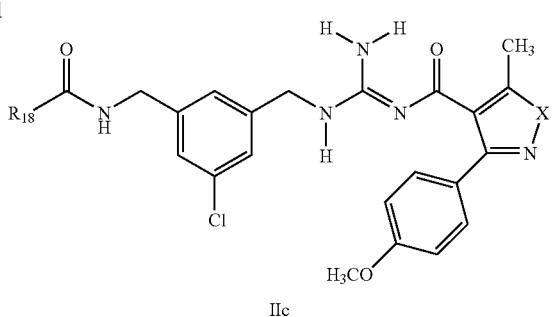

IIc

Compounds of formula IIb, IIc, IId, and IIe can be prepared from a common solid supported intermediate as described in Scheme 13. Compounds of formula IId are prepared by sequential treatment of solid supported intermediates of formula VIIb with sulfonyl chloride intermediates of formula XXIX and a base, then TFA. Intermediates of formula VIIb can be prepared via the synthetic route outlined in Scheme 1. Sulfonyl chlorides of formula XXIX can be obtained commercially, can be prepared by methods known in the literature, or can be readily prepared by one skilled in the art. Compounds of formula IIb and formula IIc are prepared by sequential treatment of solid supported intermediates of formula VIIb with carboxylic acid intermediates of formula XXX and formula XXXa, respectively, an amide bond forming reagent, then TFA. Intermediates of formula VIIa can be prepared via the synthetic route outlined in Scheme 1. Carboxylic acids of formula XXX can be obtained commercially, can be prepared by methods known in the literature, or can be readily prepared by one skilled in the art. Compounds of formula IIe are prepared by sequential treatment of solid supported intermediates of formula VIIb with chloroformate intermediates of formula XXXI and a base, then TFA. Intermediates of formula VIIa can be prepared via the synthetic route outlined in Scheme 1. Chloroformates of formula XXXI can be obtained commercially, can be prepared by methods known in the literature, or can be readily prepared by one skilled in the art.

Scheme 14

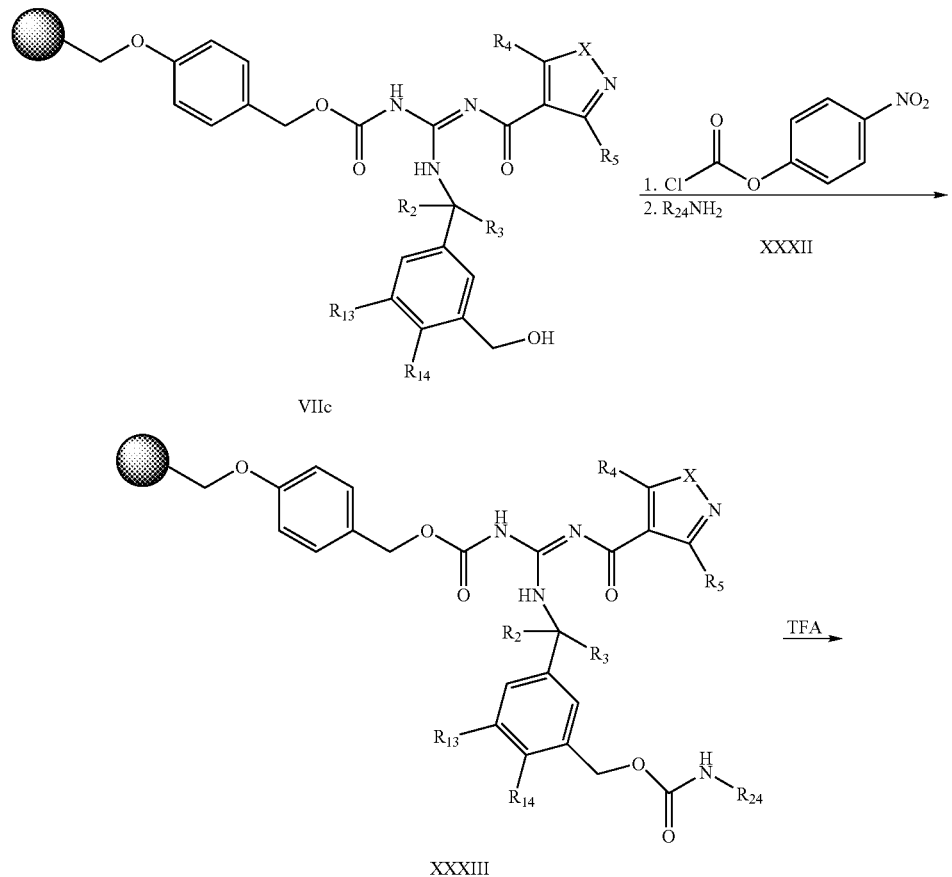

-continued

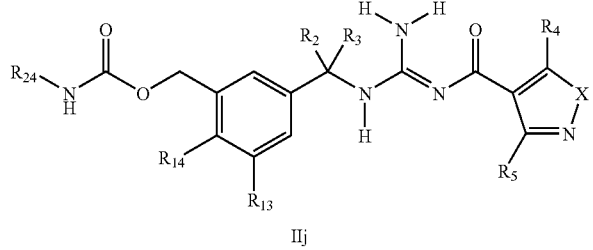

IIj

Compounds of formula IIj can be prepared as described in Scheme 14. Solid-supported intermediates of formula VIIc are treated sequentially with p-nitrophenol chloroformate then amines of formula XXXII to afford solid-supported intermediates of formula XXXIII. Intermediates of formula VIIc can be prepared via the synthetic route outlined in Scheme 1. Amines of formula XXXII can be obtained commercially, can be prepared by methods known in the literature, or can be readily prepared by one skilled in the art. Treatment of solid supported intermediates of formula XXXIII with TFA provides compounds of formula IIj.

In a preferred embodiment, the present invention includes compounds of Formula I or a stereoisomer thereof or a pharmaceutically acceptable salt thereof

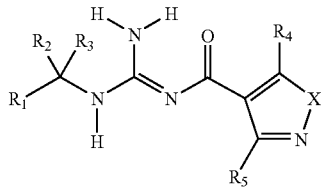

I wherein $R_1$ is naphthyl optionally substituted with halogen, quinolyl, thienyl, 2,3-dimethyl-1H-indol-5-yl, or phenyl in which said phenyl is optionally substituted with one or more groups selected from halogen, CN, $CF_3$, OH, —$NH_2$, $C_{3-6}$cycloalkyl, $C_{1-6}$alkoxy, $OR_{21}$, $C_{1-6}$alkyl optionally substituted with OH or —$NH_2$, —$(CH_2)_m$—$NHC(=O)OR_{17}$, —$(CH_2)_m$—$NHC(=O)O$phenyl optionally substituted with halogen, —$(CH_2)_m$—$NHC(=O)R_{18}$, —$NH(C=O)R_{19}$, —$CH_2NH(SO_2)R_{20}$, $R_{22}$, $R_{23}$, and —$CH_2$morpholino; $R_2$ and $R_3$ are each hydrogen; $R_4$ is $C_{1-6}$alkyl optionally substituted with $C_{1-4}$alkoxy or thiomethyl; $R_5$ is phenyl optionally substituted with one or more groups selected from halogen, $C_{1-4}$alkyl, —$S(O)_2$methyl and $C_{1-4}$alkoxy; X is O, S, or NH; m is 0 or 1; $R_{17}$ is $C_{1-4}$alkoxy, halogen, $C_{2-3}$alkynyl, 4-nitrophenyl, benzyloxy or benzothiophene 1,1-dioxide; $R_{18}$ is $C_{1-6}$alkyl or $C_{3-6}$cycloalkyl in which each is optionally substituted with a group selected from halogen, CN, $CF_3$, —$N(CH_3)_2$, $C_{1-4}$alkoxy, $C_{3-6}$cycloalkyl, morpholino, thienyl, imidazolyl, pyridyl, azepinyl, benzothienyl, benzofuranyl, phenyl and methoxyphenyl; $R_{19}$ is $C_{1-6}$alkyl optionally substituted with methoxyethyloxy or methylthio; $C_{1-4}$alkoxy optionally substituted with halogen; $C_{3-6}$cycloalkyl, phenyl, pyridyl optionally substituted with one or two halogen and $C_{1-4}$alkyl; benzothienyl, 1-methyl-2-pyrrolyl or furanyl; $R_{20}$ is $C_{1-6}$alkyl, 1,2-dimethyl-1H-imidazolyl, thienyl or phenyl in which said phenyl is optionally substituted with a group selected from acetyl, $C_{1-4}$alkoxy, benzyloxy, halogen, NH(C=O)$CH_3$ and nitro; $R_2$, is $C_{1-6}$alkyl optionally substituted with a group selected from $C_{1-4}$alkoxy, halogen, phenyl, furanyl and methylamino; $R_{22}$ is —CH=CH-phenyl or —CH=CH—$C_{1-4}$alkyl optionally substituted with $C_{1-4}$alkoxy or OH; and $R_{23}$ is pyridyl, thienyl, $C_{2-6}$alkenyl, or phenyl optionally substituted with halogen.

In another preferred embodiment, the present invention includes compounds of Formula I or a stereoisomer thereof or a pharmaceutically acceptable salt thereof wherein $R_1$ is phenyl optionally substituted with one or more groups selected from halogen, CN, $CF_3$, OH, —$NH_2$, $C_{3-6}$cycloalkyl, $C_{1-6}$alkoxy, $OR_{21}$, $C_{1-6}$alkyl optionally substituted with OH or —$NH_2$, —$(CH_2)_m$—$NHC(=O)OR_{17}$, —$(CH_2)_m$—$NHC(=O)O$phenyl optionally substituted with halogen, —$(CH_2)_m$—$NHC(=O)R_{18}$, —$NH(C=O)R_{19}$, —$CH_2NH(SO_2)R_{20}$, $R_{22}$, $R_{23}$, and —$CH_2$morpholino; $R_2$ and $R_3$ are hydrogen; $R_4$ is $C_{1-3}$alkyl; $R_5$ is phenyl optionally substituted with one or more groups selected from halogen, $C_{1-4}$alkyl, —$S(O)_2$methyl and $C_{1-4}$alkoxy; X is O or S; m is 0 or 1; $R_{17}$ is $C_{1-4}$alkoxy, halogen, $C_{2-3}$alkynyl, 4-nitrophenyl, benzyloxy or benzothiophene 1,1-dioxide; $R_{18}$ is $C_{1-6}$alkyl or $C_{3-6}$cycloalkyl in which each is optionally substituted with a group selected from halogen, CN, $CF_3$, —$N(CH_3)_2$, $C_{1-4}$alkoxy, $C_{3-6}$cycloalkyl, morpholino, thienyl, imidazolyl, pyridyl, azepinyl, benzothienyl, benzofuranyl, phenyl and methoxyphenyl; $R_{19}$ is $C_{1-6}$alkyl optionally substituted with methoxyethyloxy or methylthio; $C_{1-4}$alkoxy optionally substituted with halogen; $C_{3-6}$cycloalkyl, phenyl, pyridyl optionally substituted with one or two halogen and $C_{1-4}$alkyl; benzothienyl, 1-methyl-2-pyrrolyl or furanyl; $R_{20}$ is $C_{1-6}$alkyl, 1,2-dimethyl-1H-imidazolyl, thienyl or phenyl in which said phenyl is optionally substituted with a group selected from acetyl, $C_{1-4}$alkoxy, benzyloxy, halogen, NH(C=O)$CH_3$ and nitro; $R_{21}$ is $C_{1-6}$alkyl optionally substituted with a group selected from $C_{1-4}$alkoxy, halogen, phenyl, furanyl and methylamino; $R_{22}$ is —CH=CH-phenyl or —CH=CH—$C_{1-4}$alkyl optionally substituted with $C_{1-4}$alkoxy or OH; and $R_{23}$ is pyridyl, thienyl, $C_{2-6}$alkenyl, or phenyl optionally substituted with halogen.

In still another preferred embodiment, the present invention includes compounds of Formula Ib or a stereoisomer thereof or a pharmaceutically acceptable salt thereof

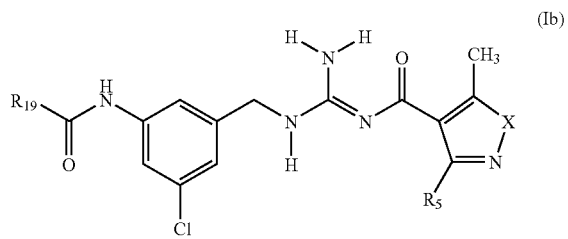

(Ib)

wherein $R_5$ is phenyl optionally substituted with one or more groups selected from halogen, $C_{1-4}$alkyl, and $C_{1-4}$alkoxy; X is O or S; and $R_{19}$ is $C_{1-6}$alkyl optionally substituted with methoxyethyloxy or methylthio; $C_{1-4}$alkoxy optionally substituted with halogen; $C_{3-6}$cycloalkyl, phenyl, pyridyl optionally substituted with one or two halogen and $C_{1-4}$alkyl; benzothienyl, 1-methyl-2-pyrrolyl or furanyl.

In yet another preferred embodiment, the present invention includes compounds of Formula Ic or a stereoisomer thereof or a pharmaceutically acceptable salt thereof

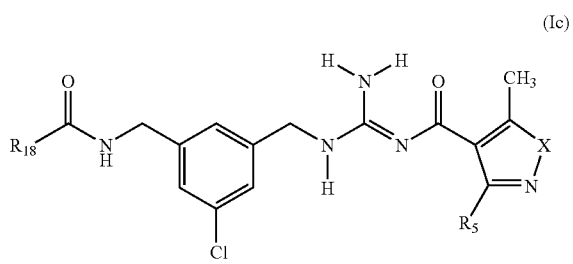

(Ic)

wherein $R_5$ is phenyl optionally substituted with one or more groups selected from halogen, $C_{1-4}$alkyl and $C_{1-4}$alkoxy; X is O or S; and $R_{18}$ is $C_{1-6}$alkyl or $C_{3-6}$cycloalkyl in which each is optionally substituted with a group selected from halogen, CN, $CF_3$, —N(CH$_3$)$_2$, $C_{1-4}$alkoxy, $C_{3-6}$cycloalkyl, morpholino, thienyl, imidazolyl, pyridyl, azepinyl, benzothienyl, benzofuranyl, phenyl and methoxyphenyl.

In still another preferred embodiment, the present invention includes compounds of Formula Id or a stereoisomer thereof or a pharmaceutically acceptable salt thereof

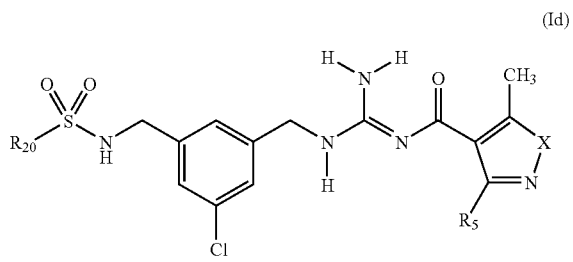

(Id)

wherein $R_5$ is optionally substituted with one or more groups selected from halogen, $C_{1-4}$alkyl and $C_{1-4}$alkoxy; X is O or S; and $R_{20}$ is $C_{1-6}$alkyl, 1,2-dimethyl-1H-imidazolyl, thienyl or phenyl in which said phenyl is optionally substituted with a group selected from acetyl, $C_{1-4}$alkoxy, benzyloxy, halogen, NH(C=O)CH$_3$ and nitro.

In yet another preferred embodiment, the present invention includes compounds of Formula Ie or a stereoisomer thereof or a pharmaceutically acceptable salt thereof

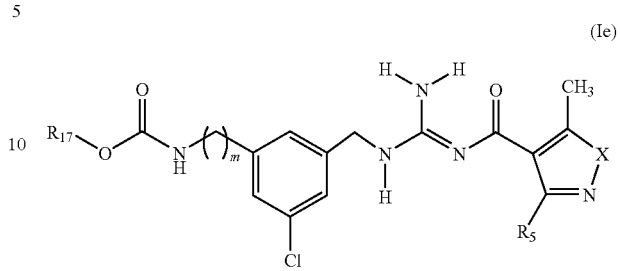

(Ie)

wherein $R_5$ is phenyl optionally substituted with one or more groups selected from halogen, $C_{1-4}$alkyl and $C_{1-4}$alkoxy; X is O or S; m is 0 or 1; and $R_{17}$ is $C_{1-4}$alkyl optionally substituted with $C_{1-4}$alkoxy, halogen, $C_{2-3}$alkynyl, 4-nitrophenyl, benzyloxy or benzothiophene 1,1-dioxide.

In yet another preferred embodiment, the present invention includes compounds of Formula Ih or a stereoisomer thereof or a pharmaceutically acceptable salt thereof

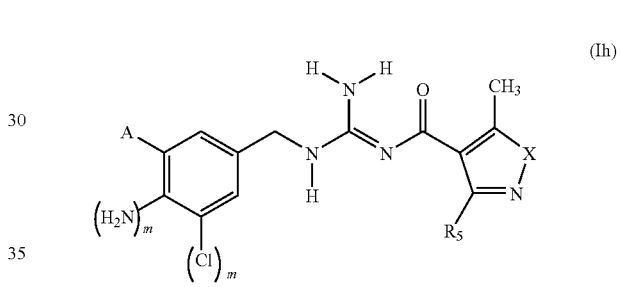

(Ih)

wherein $R_5$ is phenyl optionally substituted with one or more groups selected from halogen, $C_{1-4}$alkyl and $C_{1-4}$alkoxy; A is $R_{22}$ or $R_{23}$; m is 0 or 1; X is O or S; $R_{22}$ is —CH=CH-phenyl, —CH=CH—$C_{1-4}$alkyl optionally substituted with $C_{1-4}$alkoxy or OH; and $R_{23}$ is pyridyl, thienyl, $C_{2-6}$alkenyl, or phenyl optionally substituted with halogen.

In a further embodiment, this invention includes pharmaceutical compositions comprising at least one compound of Formula I in combination with a pharmaceutical adjuvant, carrier or diluent.

In another further embodiment, this invention relates to a method of treatment or prevention of disorders responsive to the inhibition of β-amyloid peptide in a mammal in need thereof, which comprises administering to said mammal a therapeutically effective amount of a compound of Formula I or a nontoxic pharmaceutically acceptable salt.

In yet another further embodiment, this invention relates to a method for treating Alzheimer's Disease, cerebral amyloid angiopathy and Down's Syndrome in a mammal in need thereof, which comprises administering to said mammal a therapeutically effective amount of a compound of Formula I or a nontoxic pharmaceutically acceptable salt.

DESCRIPTION OF THE SPECIFIC EMBODIMENTS

The compounds of this application and their preparation can be understood further by the following working examples. These examples are meant to be illustrative of the present application, and are not to be taken as limiting thereof.

Chemical abbreviations used in the specification and Examples are defined as follows:
"Ac" for acetate,
"APCI" for atmospheric pressure chemical ionization,
"Boc" or "BOC" for t-butyloxycarbonyl,
"BOP" for benzotriazol-1-yloxytris-(dimethylamino)-phosphonium hexafluorophosphate,
"Cbz" for benzyloxycarbonyl,
"CDI" for 1,1'-carbonyldiimidazole,
"$CD_3OD$" for deuteromethanol,
"$CDCl_3$" for deuterochloroform,
"DCC" for 1,3-dicyclohexylcarbodiimide,
"DCM" for dichloromethane
"DEAD" for diethyl azodicarboxylate,
"DIEA", "Hunig's base", or "DIPEA" for N,N-diisopropylethylamine,
"DMF" for N,N-dimethylformamide,
"DMAP" for 4-dimethylaminopyridine,
"DMPU" for 1,3-dimethyl-3,4,5,6-tetrahydro-2(1H)-pyrimidone,
"DMSO" for dimethylsulfoxide,
"DPPA" for diphenylphosphorylazide
"EDC" or "EDCI" for 1-(3-dimethylaminopropyl)-3-ethyl-carbodiimide hydrochloride,
"Et" for ethyl,
"EtOAc" for ethyl acetate,
"HOAc" for acetic acid,
"HOBt" for 1-hydroxybenzotriazole hydrate,
"HATU" for O-(7-azabenzotriazol-1-yl)-N,N,N',N'-tetramethyluronium hexafluorophosphate,
"HMPA" for hexamethylphosphoramide,
"LDA" for lithium diisopropylamide,
"LiHMDS" for lithium bis(trimethylsilyl)amide,
"NaHMDS" for sodium bis(trimethylsilyl)amide,
"NMM" for 4-methylmorpholine,
"PyBOP" for benzotriazole-1-yl-oxy-tris-pyrrolidino-phosphonium hexafluorophosphate,
"$TMSCH_2N_2$" for (trimethylsilyl)diazomethane,
"$TMSN_3$" for Azidotrimethylsilane,
"TBTU" for O-(1H-benzotriazol-1-yl)-N,N,N',N'-tetramethyluronium tetrafluoroborate,
"TEA" for triethylamine,
"TFA" for trifluoroacetic acid, and
"THF" for tetrahydrofuran.

Abbreviations used in the Examples are defined as follows:
"° C" for degrees Celsius, "MS" for mass spectrometry, "ESI" for electrospray ionization mass spectroscopy, "HR" for high resolution, "LC-MS" for liquid chromatography mass spectrometry, "eq" for equivalent or equivalents, "g" for gram or grams, "h" for hour or hours, "mg" for milligram or milligrams, "mL" for milliliter or milliliters, "mmol" for millimolar, "M" for molar, "min" for minute or minutes, "rt" for room temperature, "NMR" for nuclear magnetic resonance spectroscopy, "tlc" for thin layer chromatography, "atm" for atmosphere, and "α", "β", "R", "S", "E", and "Z" are stereochemical designations familiar to one skilled in the art.

"HPLC" is an abbreviation used herein for high pressure liquid chromatography. Reverse-phase HPLC can be carried out using a Vydac C-18 column with gradient elution from 10% to 100% buffer B in buffer A (buffer A: water containing 0.1% trifluoroacetic acid, buffer B: 10% water, 90% acetonitrile containing 0.1% trifluoroacetic acid). If necessary, organic layers can be dried over sodium sulfate unless otherwise indicated. However, unless otherwise indicated, the following conditions are generally applicable. "LC-MS" refers to high pressure liquid chromatography carried out according to the definition for HPLC with a mass spectrometry detector.

Melting points were determined on a Mel-Temp II apparatus and are uncorrected. IR spectra were obtained on a single-beam Nicolet Nexus FT-IR spectrometer using 16 accumulations at a resolution of 4.00 cm-1 on samples prepared in a pressed disc of KBr or as a film on KBr plates. Proton NMR spectra (300 MHz, referenced to tetramethylsilane) were obtained on a Varian INOUA 300, Bruker Avance 300, Avance 400, or Avance 500 spectrometer. Data were referred to the lock solvent. Electrospray Ionization (ESI) experiments were performed on a Micromass II Platform single-quadrupole mass spectrometer, or on a Finnigan SSQ7000 mass spectrometer. HPLC analyses were obtained using a Rainin Dynamax C18 column with UV detection at 223 nm using a standard solvent gradient program as follows:

HPLC solvent conditions: When described as performed under "standard conditions", Samples were dissolved in methanol (1 mg/mL) and run using the following gradient program with a solvent flow rate of 1.0 mL/min.

| Time (min) | Acetonitrile (0.05% TFA) | $H_2O$ (0.05% TFA) |
| --- | --- | --- |
| Initial | 10 | 90 |
| 20.0 | 90 | 10 |
| 20-30 | 90 | 10 |

Preparatory HPLC: When described as performed under "standard conditions", Samples (approx. 20 mg) were dissolved in methanol (10 mg/mL) and purified on a 25 mm×50 mm Vydac C18 column with a 5 minute gradient elution from 10% to 100% buffer B in buffer A (buffer A: water containing 0.1% trifluoroacetic acid, buffer B: 10% water, 90% acetonitrile containing 0.1% trifluoroacetic acid) at 10 mL/minute.

| LC/MS Method A | |
| --- | --- |
| Column | XTERRA 4.6 × 30 mm S5 |
| Flow Rate | 5 mL/min |
| Solvent A | 10% MeOH - 90% water - 0.1% TFA |
| Solvent B | 90% MeOH - 10% water - 0.1% TFA |
| Gradient | % B 0-100 |
| Gradient Time | 3 min. |

| LC/MS Method B | |
| --- | --- |
| Column | XTERRA 4.6 × 30 mm S5 |
| Flow Rate | 4 mL/min |
| Solvent A | 10% MeOH - 90% water - 0.1% TFA |
| Solvent B | 90% MeOH - 10% water - 0.1% TFA |
| Gradient | % B 0-100 |
| Gradient Time | 3 min. |

| LC/MS Method C | |
| --- | --- |
| Column | PHENOMENEX 4.6 × 30 mm S5 |
| Flow Rate | 4 mL/min |
| Solvent A | 10% MeOH - 90% water - 0.1% TFA |
| Solvent B | 90% MeOH - 10% water - 0.1% TFA |
| Gradient | % B 0-100 |
| Gradient Time | 3 min. |

| LC/MS Method D | |
| --- | --- |
| Column | Kromasil C-18 4.6 mm × 50 mm, 5 um |
| Flow Rate | 2.5 mL/min |
| Solvent A | 100% water - 0.1% TFA |
| Solvent B | 100% acetonitrile - 0.1% TFA |
| Gradient | % B 10-100 |
| Gradient Time | 4 min. |

-continued

LC/MS Method E

| | |
|---|---|
| Column | XTERRA MS C-18 4.6 × 50 mm |
| Flow Rate | 2.0 mL/min |
| Solvent A | 100% water - 10 mM NH4OAc |
| Solvent B | 100% acetonitrile |
| Gradient | % B 10-95 |
| Gradient Time | 3.5 min. |

LC/MS Method F

| | |
|---|---|
| Column | XTerra MS C18, 2.1 × 50 mm |
| Flow Rate | 1 mL/min |
| Solvent A | 100% water - 10 mM NH4OAc |
| Solvent B | 100% acetonitrile - 10 mM NH4OAc |
| Gradient | % B 10-60 over 0.8 mm, then % B 60-100 over 1.2 min |

LC/MS Method G

| | |
|---|---|
| Column | XTerra MS C18, 2.1 × 50 mm |
| Flow Rate | 4 mL/min |
| Solvent A | 100% water - 10 nM NH4OAc |
| Solvent B | 100% acetonitrile - 10 nM NH4OAc |
| Gradient | % B 0-100 |
| Gradient Time | 2 min. |

LC/MS Method H

| | |
|---|---|
| Column | PHENOMENEX C18, 3.0 × 50 mm, 10 microns |
| Flow Rate | 5 mL/min |
| Solvent A | 10% MeOH - 90% water - 0.1% TFA |
| Solvent B | 90% MeOH - 10% water - 0.1% TFA |
| Gradient | % B 0-100 |
| Gradient Time | 2 min. |

LC/MS Method I

| | |
|---|---|
| Column | Waters Sunfire, 4.6 × 50 mm |
| Flow Rate | 4 mL/min |
| Solvent A | 10% MeOH - 90% water - 0.1% TFA |
| Solvent B | 90% MeOH - 10% water - 0.1% TFA |
| Gradient | % B 0-100 |
| Gradient Time | 2 min. |

LC/MS Method J

| | |
|---|---|
| Column | XTerra MS C18, 4.6 × 50 mm |
| Flow Rate | 4 mL/min |
| Solvent A | 10% MeOH - 90% water - 0.1% TFA |
| Solvent B | 90% MeOH - 10% water - 0.1% TFA |
| Gradient | % B 0-100 |
| Gradient Time | 2 min. |

LC/MS Method K

| | |
|---|---|
| Column | Xterra, 3.0 × 50 mm, S7 |
| Flow Rate | 5 mL/min |
| Solvent A | 10% MeOH - 90% water - 0.1% TFA |
| Solvent B | 90% MeOH - 10% water - 0.1% TFA |
| Gradient | % B 0-100 |
| Gradient Time | 2 min. |

LC/MS Method L

| | |
|---|---|
| Column | Waters Sunfire, 4.6 × 50 mm, 5 μm |
| Flow Rate | 2.0 mL/min |
| Solvent A | Water - 0.1% TFA |
| Solvent B | Acetonitrile - 0.1% TFA |
| Gradient | % B 10-95 |
| Gradient Time | 3.5 min. |

LC/MS Method M

| | |
|---|---|
| Column | Xterra MS, 2.0 × 50 mm, 5 μm |
| Flow Rate | 1.0 mL/min |
| Solvent A | 5% Acetonitrile - 95% water - 10 nM NH4OAc |
| Solvent B | 95% Acetonitrile - 5% water - 10 nM NH4OAc |
| Gradient | % B 10-60 over 0.80 min, 60-95 over 1.19 min, 95-100 over 0.01 min. |
| Gradient Time | 2 min. |

SYNTHESIS OF INTERMEDIATES

Preparation A.
(3-chloronaphthalen-1-yl)methanamine

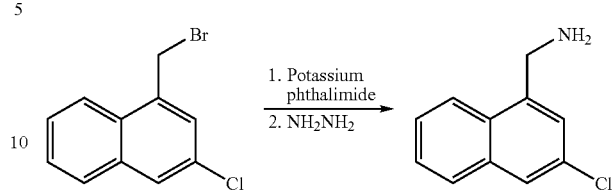

Step A1. 1-(bromomethyl)-3-chloronaphthalene, prepared by procedures described in Koh, Jong-Sung et al., PCT Int. Appl. (2000), 161 pp. (WO 2000064891), was converted to (3-chloronaphthalen-1-yl)methanamine with potassium phthalimide followed by hydrazine hydrate. LC/MS (Method A) RT 1.73 min., MH$^+$ 192. $^1$H NMR (500 MHz, CDCl$_3$) δ 8.05-7.99 (m, 1 H), 7.81-7.76 (m, 1 H), 7.74 (s, 1 H), 7.56-7.49 (m, 2 H), 7.47 (s, 1 H), 4.32 (s, 2 H).

Preparation B.
3-(aminomethyl)-5-chlorobenzylamine

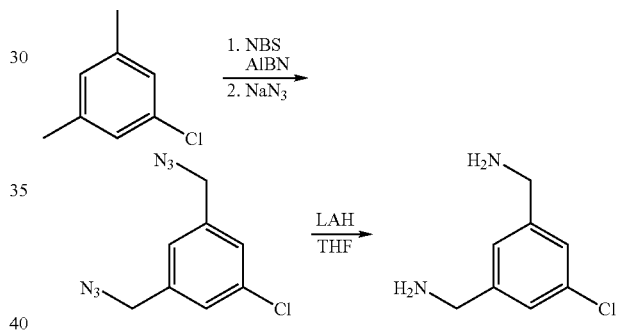

Step B1. 1-Chloro-3,5-dimethylbenzene was brominated with 2 eq. of NBS in CCl$_4$ (catalytic amount of AIBN, 85° C., overnight). The major product 1,3-bis(bromomethyl)-5-chlorobenzene was isolated by flash chromatography over silica gel (DCM/hexanes, 5:95). $^1$H NMR (500 MHz, CDCl$_3$) δ 7.31 (2 H), 7.29 (1 H), 4.41 (s, 4 H).

Step B2. The mixture of 1,3-bis(bromomethyl)-5-chlorobenzene (4.69 g, 15.7 mmol) and sodium azide (2.55 g, 39.2 mmol) in THF/water (4:1, 100 mL) was stirred at reflux for 4 hrs. The reaction mixture was cooled and DCM (200 mL) and water (200 mL) were added. Layers were separated and the aqueous layer was extracted with DCM (200 mL). The combined DCM extract was dried over anhydrous sodium sulfate. The solvents were evaporated in vacuo to give the 3.50 g of 1,3-bis(azidomethyl)-5-chlorobenzene. $^1$H NMR (500 MHz, CDCl$_3$) δ 7.29 (s, 2 H), 7.15 (s, 1 H), 4.36 (s, 4 H).

Step B3. The solution of 3.50 g of 1,3-bis(azidomethyl)-5-chlorobenzene in THF (20 mL) was added slowly to the LAH (1.33 g, 35.0 mmol) suspension in THF at 0° C. The resulting reaction mixture was stirred at RT for 1 hr. and then at reflux for another hour. Slow addition of 2 mL of 5% NaOH solution resulted a precipitate, which was removed by filtration. The product on solid was rinsed off with THF. The solvent was evaporated in vacuo to yield 2.60 g of 3-(aminomethyl)-5-chlorobenzylamine. $^1$H NMR (500 MHz, CD$_3$OD) δ 7.25 (s, 2 H), 7.21 (s, 1 H), 3.76 (s, 4 H).

Preparation C.
4-amino-3-chloro-5-methylbenzylamine

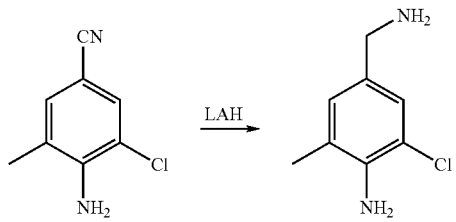

Step C1. 4-Amino-3-chloro-5-methylbenzonitrile was reduced to 4-amino-3-chloro-5-methylbenzylamine by heating it at reflux with 2.2 eq. of LAH in THF for 2 hrs. LCMS (Method A) RT 0.32 min., (2M+H)$^+$ (341, base MS peak 154). $^1$H NMR (500 MHz, CD$_3$OD) δ 7.07 (s, 1 H), 6.92 (s, 1 H), 3.59 (s, 2 H), 2.18 (s, 3 H).

Preparation D.
4-acetamido-3-chloro-5-methylbenzylamine

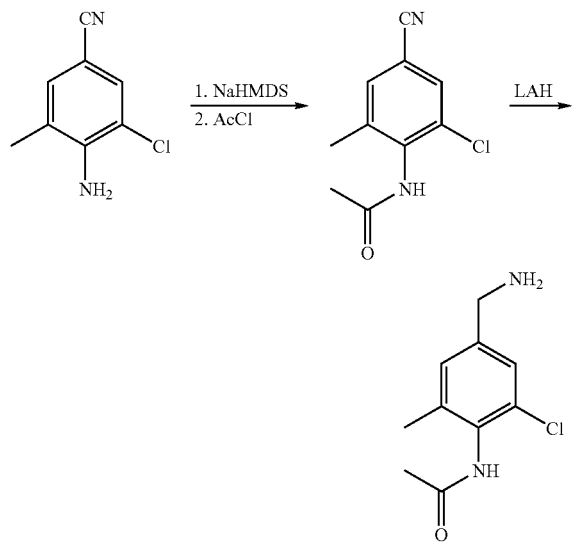

Step D1. To a stirred solution of 4-amino-3-chloro-5-methylbenzonitrile (0.516 g, 3.1 mmol) in 10 mL of THF at room temperature was added 6.6 mL of 1.0 M NaHMDS in THF. The resulting reaction mixture was stirred at room temperature for 30 min., at which time acetyl chloride (3.1 mmol) was added. DCM (100 mL) and water (100 mL) were added to the reaction mixture after being stirred overnight, followed by the addition of 5 mL of 1.4 N HCl aqueous solution. Layers were separated and the aqueous layer was extracted with DCM (2×100 mL). The extracts were combined and solvents were evaporated in vacuo. The residue was purified by flash chromatography (5-20% EtOAc/DCM) to give 0.220 g of 4-acetamido-3-chloro-5-methylbenzonitrile. $^1$H NMR (500 MHz, CDCl$_3$) δ 7.57 (s, 1 H), 7.46 (s, 1 H), 7.02 (s, 1 H), 2.31 (s, 3 H), 2.26 (s, 3 H).

Step D2. The nitrile was reduced by analogy to Step C1. $^1$H NMR (500 MHz, CD$_3$OD) δ 7.31 (s, 1 H), 7.17 (s, 1 H), 3.73 (s, 2 H), 2.23 (s, 3 H), 2.15 (s, 3 H).

Preparation E. 3-amino-5-chlorobenzylamine

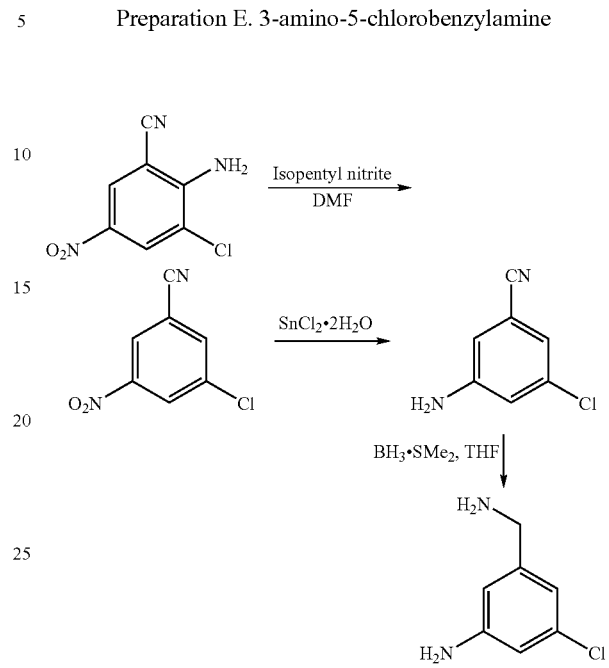

Step E1. To prepare 3-chloro-5-nitrobenzonitrile from 2-amino-3-chloro-5-nitrobenzonitrile, a literature procedure (Doyle, M. P. et al. *J. Org. Chem.* 1977, 42, 3494-3498.) was followed except that the reaction temperature was 65-75° C. and the reaction time was 2 days. The product was purified by chromatography over silica gel (84% yield). $^1$H NMR (500 MHz, CDCl$_3$) δ 8.45 (t, J=1.7 Hz, 1 H), 8.42 (s, 1 H), 7.97 (s, 1 H).

Step E2. 3-Chloro-5-nitrobenzonitrile was reduced to 3-amino-5-chlorobenzonitrile by treating with 6 equivalents of SnCl$_2$ dihydrate in DMF at RT overnight. The product was purified by chromatography over silica gel (40% yield). LCMS (Cond. A) RT 1.61 min., MH$^+$ 153. $^1$H NMR (500 MHz, CDCl$_3$) δ 6.97 (s, 1 H), 6.84 (t, J=2.0 Hz, 1 H), 6.77 (s, 1 H).

Step E3. To the solution of 3-amino-5-chlorobenzonitrile in THF at RT was added slowly borane methyl sulfide complex (2.5 eq.). The resulting reaction mixture was stirred at RT for 1 h and heated at reflux for 2 hrs. The reaction mixture was cooled to −30° C. and MeOH was added slowly to quench the reaction. Solvent was evaporated in vacuo after the reaction mixture was stirred at RT for 30 min. to give 3-amino-5-chlorobenzylamine, which was used without purification. LCMS (Method A) RT 0.16 min., MH$^{30}$ 157.

Preparation F. 3-chloro-5-hydroxybenzylamine

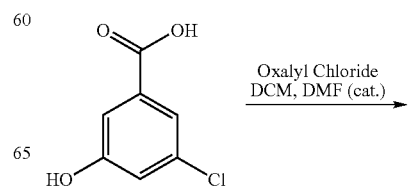

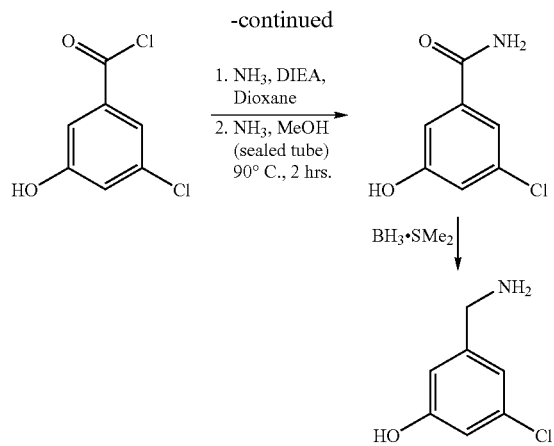

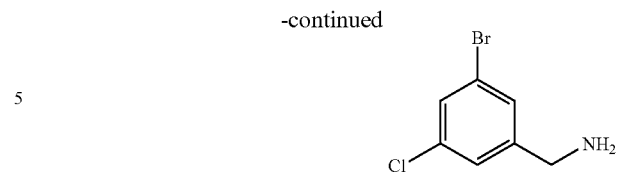

Step F1. A mixture of 3-chloro-5-hydroxybenzoic acid (3.22 mmol), oxalyl chloride (6.5 mmol) and catalytic amount of DMF in DCM was heated at reflux for 2 hrs. (bath temperature at 60° C.). Solvent was evaporated in vacuo and the residue was dissolved in 1,4-dioxane. NH$_3$ (0.5 M in 1,4-dioxane, 1.5 eq.) and DIEA (1.5 eq.) were added and the reaction mixture was stirred at RT overnight. The reaction mixture was transferred to a pressure vessel, followed by the addition of 1 mL of 6 M NH$_3$ in MeOH. The pressure vessel was sealed and heated at 90° C. for 2 hrs. The solvents were evaporated to give a crude product, which was purified by chromatography over silica gel (EtOAc) to yield 0.51 g (57%, theoretical yield 0.896 g) of 3-chloro-5-hydroxybenzamide. LCMS (Cond. A) RT 1.05 min., MH$^{30}$ 172. $^1$H NMR (500 MHz, CD$_3$OD) δ 7.31 (t, J=1.7 Hz, 1 H), 7.19 (t, J=1.8 Hz, 1 H), 6.94 (t, J=2.1 Hz, 1 H).

Step F2. 3-Chloro-5-hydroxybenzamide was reduced to 3-chloro-5-hydroxybenzylamine with borane methyl sulfide complex in THF (2.5 eq., heated at reflux, overnight). LCMS (Cond. A) RT 0.40 min., MH$^{30}$ 158.

Preparation G. 3-Bromo-5-chlorobenzylamine

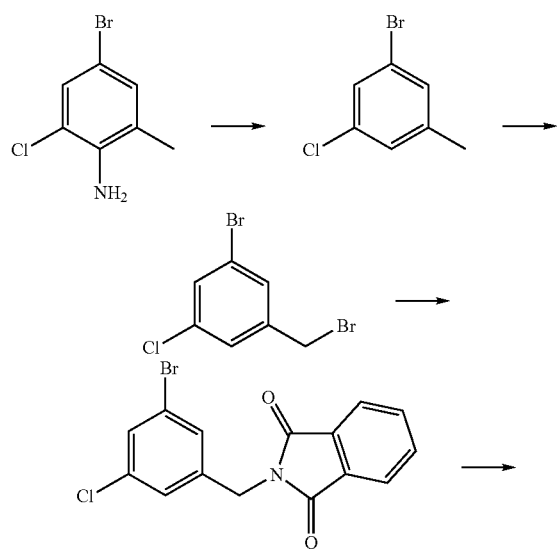

Step G1. To an ice-water-cooled and stirred solution of 2-amino-5-bromo-3-chlorotoluene (12 g, 54 mmol) in a mixture of 100 mL of acetic acid, 43 mL of H$_2$O and 11.5 mL of concentrated HCl was added dropwise a solution of NaNO$_2$ (4.48 g, 65 mmol) in 15 mL of H$_2$O. The reaction mixture was stirred for 30 min and was then added to an 112 mL solution of 50% H$_3$PO$_2$ cooled at 0° C. After being stirred for 6 h at 0° C., the reaction mixture was allowed to stand at room temperature overnight. The solid was filtered and washed with water, then dried in vacuum. 3-Chloro-5-bromo-toluene (9 g, 81%) was obtained as brown solid. Crystals. $^1$H NMR (CDCl$_3$): δ 2.31 (s, 3H), 7.10 (s, 1H), 7.21 (s, 1H), 7.31 (s, 1H).

Step G2. The mixture of 3-bromo-5-chlorotoluene (9 g, 43.8 mmol), NBS (8.19 g, 46 mmol), and AIBN (200 mg) in carbon tetrachloride (50 mL) was heated at 80° C. for 3 hours. The resulting mixture was run through a silicon gel column with dichloromethane as the eluant. The fraction was collected and solvent was removed by rotovap, crude 1-bromo-3-(bromomethyl)-5-chlorobenzene (3) was obtained as a brown residue and used in the next step without further purification.

Step G3. A mixture of 1-bromo-3-(bromomethyl)-5-chlorobenzene (6 g, ~21 mmol) and potassium phthalimide (3.15 g, 17 mmol) in DMF (50 ml) was heated at 120° C. for 2 hours. After cooled down, a white solid precipitated. The solid was filtered and washed with ethanol, then dried in vacuum. 2-(3-Bromo-5-chlorobenzyl)isoindoline-1,3-dione (5.1 g, 85%) was obtained as white solid. $^1$H NMR (DMSO-d$_6$): δ3.72 (s, 2H), 7.43 (s, 1H), 7.51 (s, 1H), 7.52 (s, 1H), 7.84,7.86 (d,2H), 8.05,8.07 (d,2H).

Step G4. A mixture of 2-(3-Bromo-5-chlorobenzyl)isoindoline-1,3-dione (5.1 g, 14.6 mmol) and hydrazine monohydrate (0.8 g, 16 mmol) in ethanol (150 mL) was refluxed for 4 hours. Upon cooling to room temperature, a white solid precipitated. The solid was filtered and washed with ethanol, then dried in vacuum. $^1$H NMR (DMSO-d$_6$) showed that the white solid is a mixture of 3-bromo-5-chlorobenzylamine and 2,3-dihydrophthalazine-1,4-dione. This material was used in subsequent steps without further purification.

Preparation H. 3,5-Dibromobenzylamine

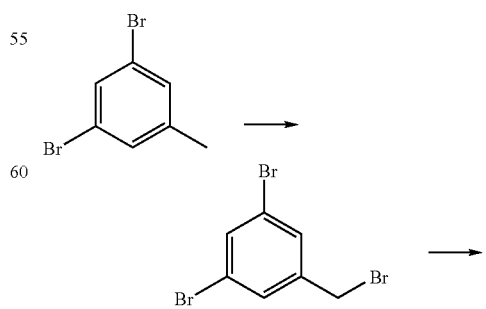

-continued

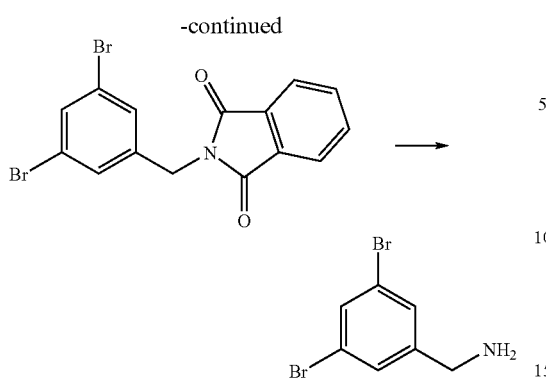

Step H1. A mixture of 3,5-dibromo-toluene (4.25 g, 17 mmol), NBS (3 g, 17 mmol), and AIBN (150 mg) in carbon tetrachloride (50 mL) was heated at 80° C. for 3 hours. The resulting mixture was run through a silicon gel column with dichloromethane as the eluant. The fraction was collected and solvent was removed by rotovap, crude 1,3-dibromo-5-(bromomethyl)benzene was obtained as a white residue.

Step H2. A mixture of 1,3-dibromo-5-(bromomethyl)benzene (1.1 g, ~3.3 mmol) and potassium phthalimide (0.62 g, 3.3 mmol) in DMF (10 ml) was heated at 120° C. for 2 hours. After cooled down, a white solid precipitated. The solid was filtered and washed with ethanol, then dried in vacuum. 2-(3,5-dibromobenzyl)isoindoline-1,3-dione (1.1 g, 83%) was obtained as white solid.

Step H3. The mixture of 22-(3,5-dibromobenzyl)isoindoline-1,3-dione (1.1 g, 2.78 mmol) and hydrazine monohydrate (0.15 g, 3.0 mmol) in ethanol (30 mL) was refluxed for 4 hours. After cooled down, a white solid precipitated. The solid was filtered and washed with ethanol, then dried in vacuum. $^1$H NMR (400 MHz, DMSO-$d_6$) showed that the white solid is a mixture of 3,5-dibromobenzylamine and 2,3-dihydrophthalazine-1,4-dione. This material was used in subsequent steps without further purification.

Preparation I.
4-Amino-3-bromo-5-chlorobenzonitrile

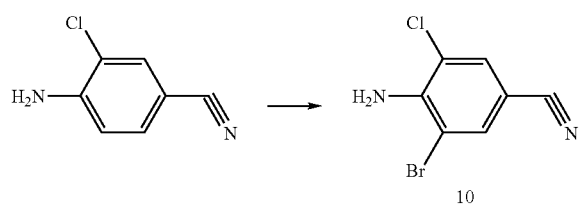

To 3-chloro-4-amino-benzonitrile (5 g, 32.9 mmol) in Methanol (80 mL) was added dropwise bromine (5.3 g, 33.1 mmol) in Methanol (20 mL). The mixture was stirred for 1.5 hours. Solvent was removed by rotovap and resulting solid was dried in vacuum.

3-Chloro-4-amino-5-bromobenzonitrile was obtained as a white solid. $^1$H NMR (300 MHz, CD$_3$OD): δ 7.63 (s, 1H), 7.75 (s, 1H). MH$^+$=230.97, 232.97.

Preparation J. 3,5-Dichloro-4-aminobenzylamine

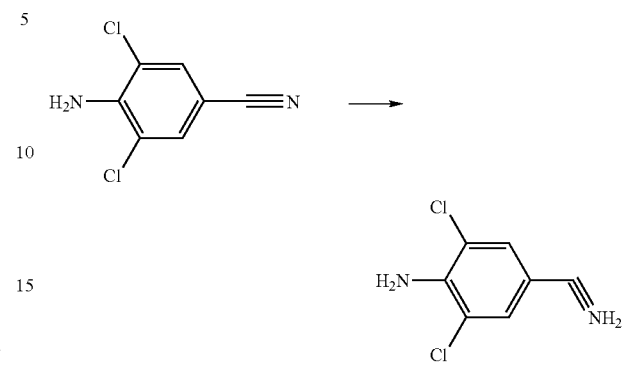

To lithium aluminum hydride (0.57 g, 15 mmol) in dry THF (20 mL) was added dropwise 3,5-dichloro-4-aminobenzonitrile (1.87 g, 10 mmol) in THF (30 mL). The mixture was stirred at RT for 2 hours. Then, sodium sulfate decahydrate (4.83 g, 15 mmol) was added and stirred for 30 min. The solid was filtered off and washed with THF for three times. The solvent was removed by rotovap and residue was purified by column with Methanol/DCM (3:7) as the eluant. 3,5-Dichloro-4-aminobenzylamine was obtained as an off-white solid (1.5 g, 80%). $^1$H NMR (300 MHz, CD$_3$OD): δ 3.65 (s, 2H), 7.2 (s, 2H).

Preparation K. 3-Chloro-4-aminobenzylamine

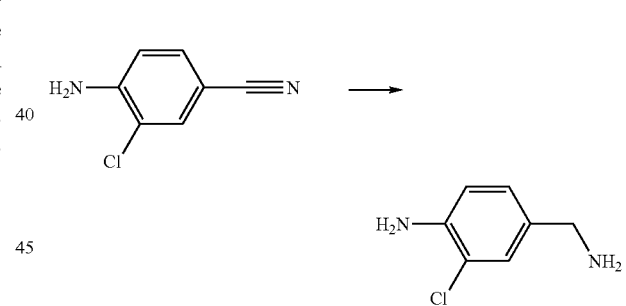

Prepared by analogy to Preparation J. $^1$H NMR (CD$_3$OD): δ 3.65 (s, 2H), 6.80, 6.82 (d, 1H), 7.02,7.04(d, 1H), 7.21 (s, 1H).

Preparation L.
3-Chloro-4-amino-5-bromobenzylamine

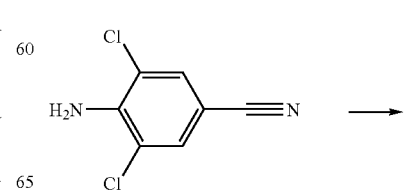

-continued

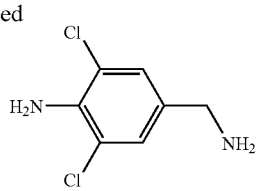

Prepared by analogy to Preparation J. $^1$H NMR (300 Hz, CD$_3$OD): δ 3.73 (s, 2H), 7.29 (s, 1H), 7.41(s, 1H).

Preparation M.
3-Chloro-4-amino-5-iodobenzylamine

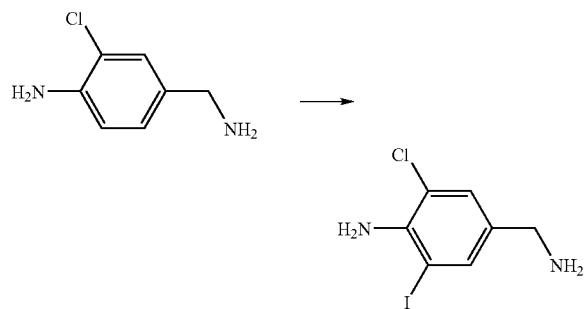

To 3-Chloro-4-aminobenzylamine (200 mg, 1.28 mmol) in methanol (5 mL) was added iodine monochloride (230 mg, 1.42 mmol). The mixture was stirred for 1 hour, then purified by HPLC to give 3-chloro-4-amino-5-iodobenzylamine (150 mg, 42%).

Preparation N.
3-chloro-5-(hydroxymethyl)benzylamine

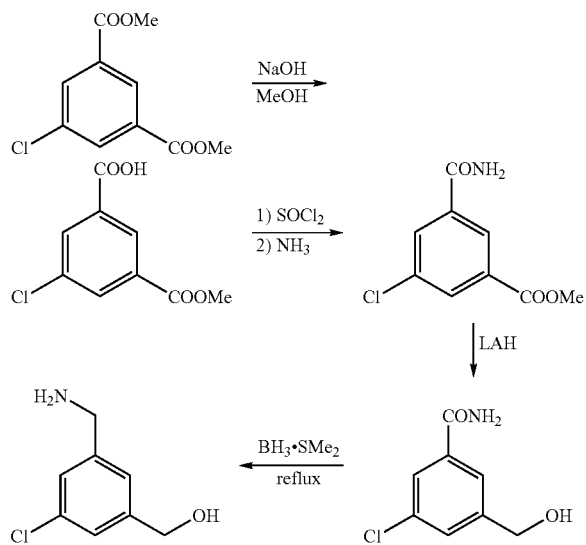

Step N1. A mixture of dimethyl 5-chloroisophthalate (6.84 g, 30 mmol), in methanol (150 mL) was treated with 1M sodium hydroxide (27 mL, 27 mmol) and the reaction stirred at room temperature for 16 hours. The mixture was concentrated under vacuum and the resulting residue was dissolved in water. The mixture was extracted with ethyl acetate three times. The organic extract was dried over anhydrous sodium sulfate, filtered and concentrated to afford 3-chloro-5-(methoxycarbonyl)benzoic acid (4.8 g, 75%).

Steps N2 and N3. A mixture of 3-chloro-5-(methoxycarbonyl)benzoic acid (2 g, 9.3 mmol) and thionyl chloride (8 mL) was refluxed for 2 hours. After the excess thionyl chloride was removed under vacuum, the residue was treated with a 0.5M solution of ammonia in 1,4-dioxane (40 mL, 20 mmol) overnight. The solvent was removed under vacuum and methyl 3-carbamoyl-5-chlorobenzoate was obtained as a white solid.

Step N4. To above methyl 3-carbamoyl-5-chlorobenzoate (~9.3 mmol) in dry THF (100 mL) was added lithium aluminum hydride (1 g, 26.3 mmol) in portions. The mixture was stirred for 4 hours, then treated with sodium sulfate decahydrate (8.5 g, 26.3 mmol) for 30 min. The solid was filtered off and washed with THF for three times. The solvent was removed under vacuum and resulting residue was purified by column with DCM, then MeOH/DCM (5/95) to give 3-chloro-5-(hydroxymethyl)benzamide (13, 0.7 g, 40%).

Step N5. To 3-chloro-5-(hydroxymethyl)benzamide (0.7 g, 3.77 mmol) in THF (20 mL) was added borane-dimethylsulfide complex (0.9 g, 11.8 mmol) slowly. The mixture was refluxed for 20 hours. Excess borane reagent was quenched with methanol and solvent was removed by rotovap. The resulting residue was purified by column with dichloromethane/methanol (1:1) as the eluant. 3-chloro-5-(hydroxymethyl)benzylamine was obtained in white solid (240 mg, 37%). $^1$H NMR (300 MHz, CD$_3$OD): δ 3.81 (s, 2H), 4.61 (s, 2H), 7.25 (s, 1H), 7.28(s, 1H), 7.59, 7.30(s, 1H). MH$^+$=172.08.

Preparations O to R

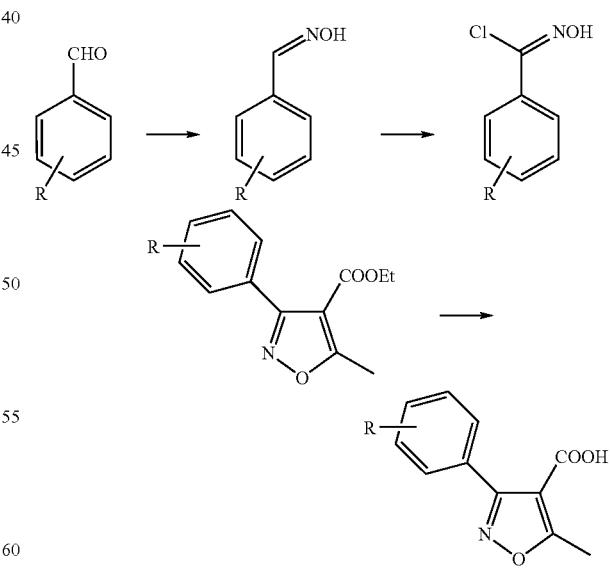

All 5-methyl-3-aryl-isoxazole-4-carboxylic acids were prepared according to the reference: Gerald W. Zamponi, Stephanie C. Stotz, Richard J. Staples, Tina M. Andro, Jared K. Nelson, Victoria Hulubei, Alex Blumenfeld, and Nicholas R. Natale, J. Med. Chem., 2003, 46, 87-96

Preparation O. 3-(3,5-difluorophenyl)-5-methylisoxazole-4-carboxylic acid

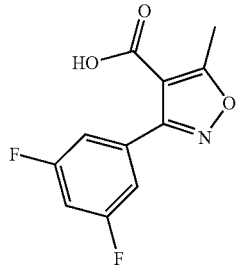

From 4.24 g of 3,5-difluorobenzaldehyde, 4.74 g (66.7%) of the title compound was prepared. H¹-NMR(CD₃OD, 300 MHz): δ 7.32~7.26(2H,m), 7.12~7.06(1H,m), 2.73(3H,s).

Preparation P. 3-(3,5-Dimethylphenyl)-5-methylisoxazole-4-carboxylic acid

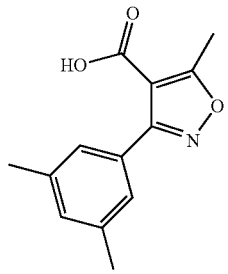

From 4.0 g of 3,5-dimethylbenzaldehyde, 4.90 g (97%) of the title compound was prepared. H¹-NMR(CD₃OD, 300 MHz): δ 7.20(2H,s), 7.11(1H,s), 2.71(3H,s), 2.34(6H,s).

Preparation Q. 3-(Benzo[d][1,3]dioxol-5-yl)-5-methylisoxazole-4-carboxylic acid

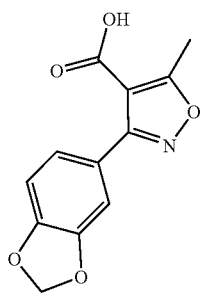

From 3.0 g of benzo[d][1,3]dioxole-5-carbaldehyde, 1.56 g (36%) of the title compound was prepared. H¹-NMR (CD₃OD, 300 MHz): δ 7.18~7.14(2H, m)), 6.92~6.90(1H, m), 6.06(2H, s), 2.72(3H, s).

Preparation R. 3-(2,3-dihydrobenzo[b][1,4]dioxin-6-yl)-5-methylisoxazole-4-carboxylic acid

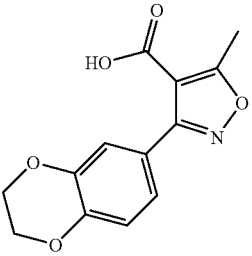

From 5.0 g of benzo[d][1,3]dioxole-5-carbaldehyde, 2.70 g (34%) of the title compound was prepared. H¹-NMR (CD₃OD, 300 MHz): δ 7.16~7.11 (2H, m), 6.99~6.89(1H, m), 3.38~3.33(4H,m), 2.74(3H, s).

Preparation S. 3-(3-chlorophenyl)-5-methylisoxazole-4-carboxylic acid

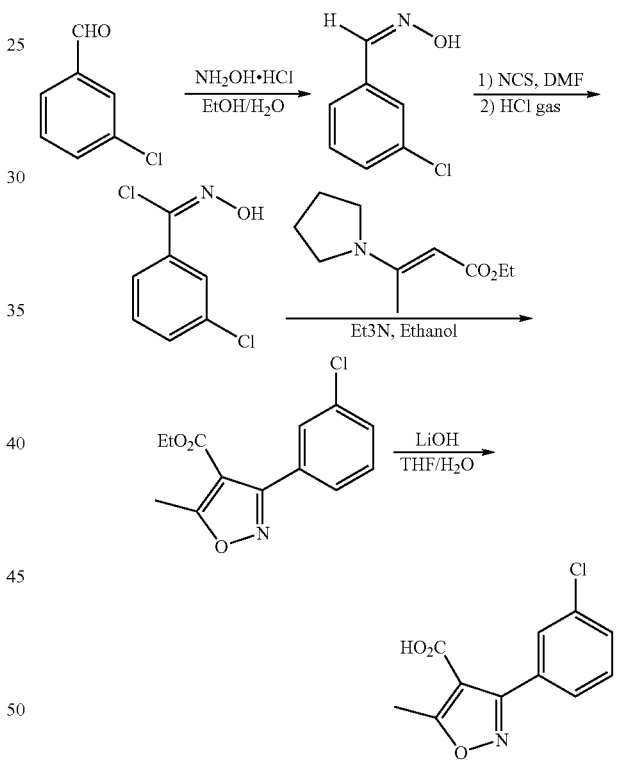

Step S1. To a stirred solution of 3-chlorobenzaldehyde (7.29 g, 0.051M) in water (13 ml), 95% absolute alcohol (13 ml) and 25 g of ice, hydroxylamine hydrochloride (3.9 g, 0.056M) was added, followed by 50% sodium hydroxide (5 ml). The reaction mixture was stirred for an hour, acidified with conc. HCl to strongly acidic, and extracted with dichloromethane (3×50 ml). The combined organic layer was dried over anhydrous sodium sulphate and concentrated under vacuum to give pure product, 7.2 g (89%) as white solid.

Step S2. To a stirred solution of the oxime (5.3 g, 0.034M) in DMF (30 ml) was added one fifth of N-chlorosuccinimide (4.5 g, 0.034M). After 10 min HCl gas was bubbled and the temperature was maintained below 35° C. by periodic ice cooling. The rest of NCS was added in portions and the reaction mixture was stirred over night. The reaction mixture was poured into (250 ml) and extracted with diethyl ether (3×100 ml). The combined organic layer was washed with water (2×100 ml), dried over anhydrous sodium sulphate and concentrated under vacuum to give pure product, 6.1 g (93%).

Step S3. To a solution of the enamine of ethylacetoacetate (5.7 g, 0.0311M) and triethylamine (2.5 ml) in absolute alcohol (90 ml) at 0° C. under $N_2$ was added a solution of 3-chlorobenzohydroxyiminoyl chloride (6 g, 0.0311M) in absolute alcohol (30 ml), drop wise via an addition funnel. The resulting yellow solution was warmed to room temperature and allowed to stir overnight. The ethanol was removed under vacuum and the residue was taken up in diethylether (150 ml) and washed with 1M HCl (75 ml),water (3×50 ml), dried over anhydrous sodium sulphate. The organic layer concentrated under vacuum to give the crude product, 7 g (84%), which was taken into the next step without further purification.

Step S4. To a stirred solution of ethyl ester (8.67 g, 0.0311M) in $THF/H_2O$ (170/42.5 ml) was added lithium hydroxide (1.7 g, 0.071M). The reaction mixture was stirred at RT over night and the solvent, THF was removed from the reaction mixture under vacuum. The resulting mass was diluted with water and washed with diethylether (2×50 ml). Then the aqueous solution was acidified with conc.HCl (pH~2) and was extracted with ethyl acetate (2×50 ml). The combined organic layer was dried over anhydrous sodium sulphate, concentrated under vacuum to give the final product, 5 g (65%) as white solid. $^1$H NMR (DMSO-$d_6$): δ 2.7 (3H, s), 7.49-7.56(1H, m), 7.60 (2H, d), 7.68 (1H, s), 12.6 (1H, br s). $^{13}$C NMR (DMSO-$d_6$) δ 13.1, 108.6, 127.9, 128.9, 129.5, 129.9, 130.4, 132.6, 161.0, 162.4, 175.8. MH$^+$=238.

Preparation T.
3-(3-methoxyphenyl)-5-methylisoxazole-4-carboxylic acid

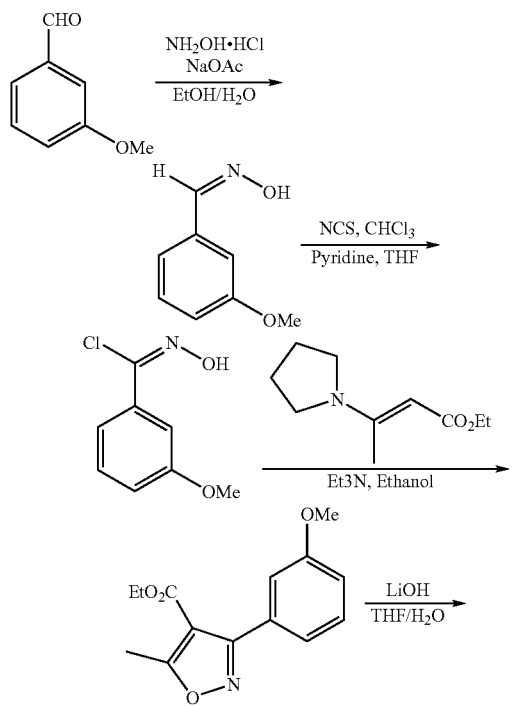

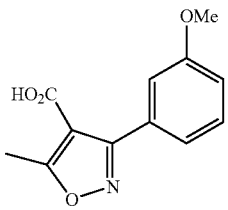

Step T1. To a stirred solution of 3-methoxybenzaldehyde (10 g, 0.073M) in ethanol (100 ml) was added the solution of hydroxylamine hydrochloride (6.1 g, 0.008M) in water (20 ml), followed by sodium acetate (6.4 g, 0.008M) in water (30 ml). Then the reaction mixture was heated to 60° C. for 2 hours. The solvent was removed under vacuum and the product was extracted from the aqueous solution with DCM (2×75 ml). The combined organic layer was washed with water (2×50 ml), dried over anhydrous sodium sulphate and concentrated under vacuum to give the pure product, 10.2 g (92%).

Step T2. To a stirred solution of 3-methoxybenzaldehyde oxime (10.2 g, 0.067M) in dry $CHCl_3$/THF (100/50 ml) under $N_2$, N-chlorosuccinimide (10.2 g, 0.077M) was added, followed by pyridine (0.5 ml). The reaction mixture was stirred at RT for 2 hours and was concentrated under vacuum. The resulting mass was poured into ice water (250 ml) and extracted with diethyl ether (3×100 ml). The combined organic layer was washed with water (2×100 ml), dried over anhydrous sodium sulphate and concentrated under vacuum to give the product, 10 g (80%).

Step T3. To a solution of the enamine of ethylacetoacetate (9.9 g, 0.054M) and triethylamine (7.4 ml, 0.054M) in absolute alcohol (100 ml) at 0° C. under $N_2$ was added a solution of chloro oxime (10 g, 0.054M) in absolute alcohol (70 ml), drop wise via an addition funnel. The reaction mixture was warmed to RT and stirred overnight. The ethanol was removed under vacuum and the residue was taken up in diethyl ether (250 ml) and washed with 1M HCl (100 ml), water (3×75 ml), dried over anhydrous sodium sulphate. The organic layer concentrated under vacuum to give the crude product, 5 g (35%), which was used in the next step without further purification.

Step T4. To a stirred solution of product of T3 (5 g, 0.020M) in $THF/H_2O$ (75/18.75 ml) was added lithium hydroxide (4.7 g, 0.2M). The reaction mixture was stirred at RT for over night and the solvent, THF was removed from the reaction mixture under vacuum. The resulting mass was diluted with water and washed with diethyl ether (2×50 ml). Then the aqueous solution was acidified with sat. Oxalic acid (PH~4) and was extracted with ethyl acetate (2×75 ml). The combined organic layer was dried over anhydrous sodium sulphate, concentrated under vacuum to give the crude product which was purified by column chromatography over silica gel (60-120) using 9.5/0.5 DCM/MeOH as eluent (1.5 g, 32%). $^1$H NMR (DMSO-$d_6$): δ 2.69 (3H, s), 3.78 (3H, s), 7.17 (2H, dd), 7.36 (2H, dd), 13.08 (1H, br s). $^{13}$C NMR (DMSO-$d_6$) δ 13.5, 55.6, 109.1, 115.2, 115.7, 121.8, 129.6, 130.0, 159.2, 162.3, 163.1, 176.0. MH$^+$=234.

Preparation U.
5-methyl-3-m-tolylisoxazole-4-carboxylic acid

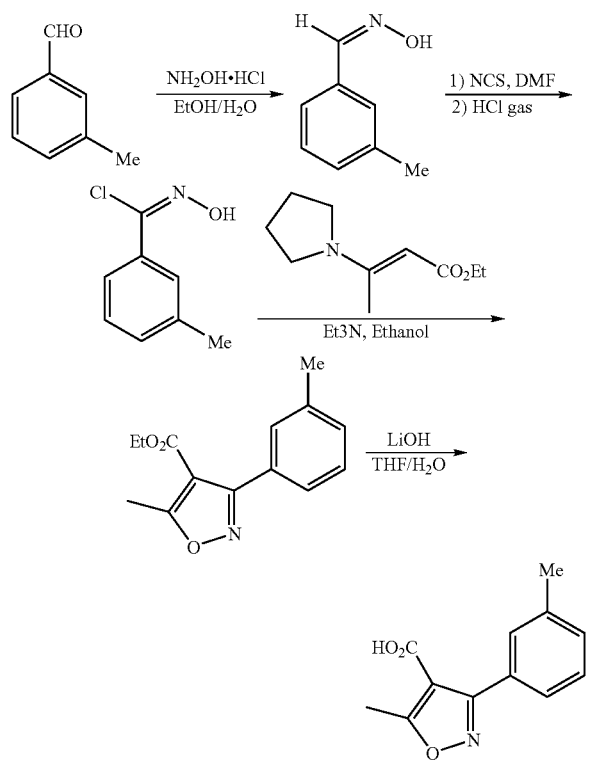

Step U1. To a stirred solution of m-tolualdehyde (8 g, 0.066M) in water (13 ml), 95% absolute alcohol (13 ml) and 25 g of ice, hydroxylamine hydrochloride (4.6 g, 0.066M) was added, followed by 50% sodium hydroxide (5 ml). The reaction mixture was stirred for an hour, acidified with conc. HCl to strongly acidic, and extracted with dichloromethane (3×50 ml). The combined organic layer was dried over anhydrous sodium sulphate and concentrated under vacuum to give pure product, 7.4 g (82%) as yellow liquid.

Step U2. To a stirred solution of the oxime (7.9 g, 0.0585M) in DMF (30 ml) was added one fifth of N-chlorosuccinimide (7.8 g, 0.0585M). After 10 min HCl gas was bubbled and the temperature was maintained below 35° C. by periodic ice cooling. The rest of NCS was added in portions and the reaction mixture was stirred over night. The reaction mixture was poured into (250 ml) and extract with diethyl ether (3×100 ml). The combined organic layer was washed with water (2×100 ml), dried over anhydrous sodium sulphate and concentrated under vacuum to give pure product, 6 g (60%).

Step U3. To a solution of the enamine of ethyl acetate (7.0 g, 0.038M) and triethylamine (2.5 ml) in absolute alcohol (65 ml) at 0° C. under $N_2$ was added a solution of product of Step U2 (6.5 g, 0.038M) in absolute alcohol (50 ml), drop wise via an addition funnel. The reaction mixture was warmed to RT and stirred overnight. The ethanol was removed under vacuum and the residue was taken up in diethyl ether (150 ml) and washed with 1M HCl (75 ml), water (3×50 ml), dried over anhydrous sodium sulphate. The organic layer concentrated under vacuum to give the crude product, 7.1 g (75%), as yellow oil which was used in the next step without further purification.

Step U4. To a stirred solution of product of Step U3 (7.1 g, 0.028M) in THF/$H_2O$ (100/25 ml) was added lithium hydroxide (2.9 g, 0.121M). The reaction mixture was stirred at RT for over night and the solvent, THF was removed from the reaction mixture under vacuum. The resulting mass was diluted with water and washed with diethyl ether (2×50 ml). Then the aqueous solution was acidified with sat. oxalic acid (pH~4) and was extracted with ethyl acetate (2×50 ml). The combined organic layer was dried over anhydrous sodium sulphate, concentrated under vacuum to give the final product, 5.7 g (90%) as yellow solid. $^1$H NMR (DMSO-$d_6$): δ 2.38 (3H, s), 2.68 (3H, s), 7.31 (1H, t), 7.35 (1H, s), 7.37(2H, d), 12.80 (1H, br s). $^{13}$C NMR (DMSO-$d_6$) δ 13.5, 21.3 109.2, 126.8, 128.3, 128.8, 129.9, 130.6, 137.6, 162.6, 163.2, 175.8. $MH^+$=218.

Preparation V.
5-methyl-3-p-tolylisoxazole-4-carboxylic acid

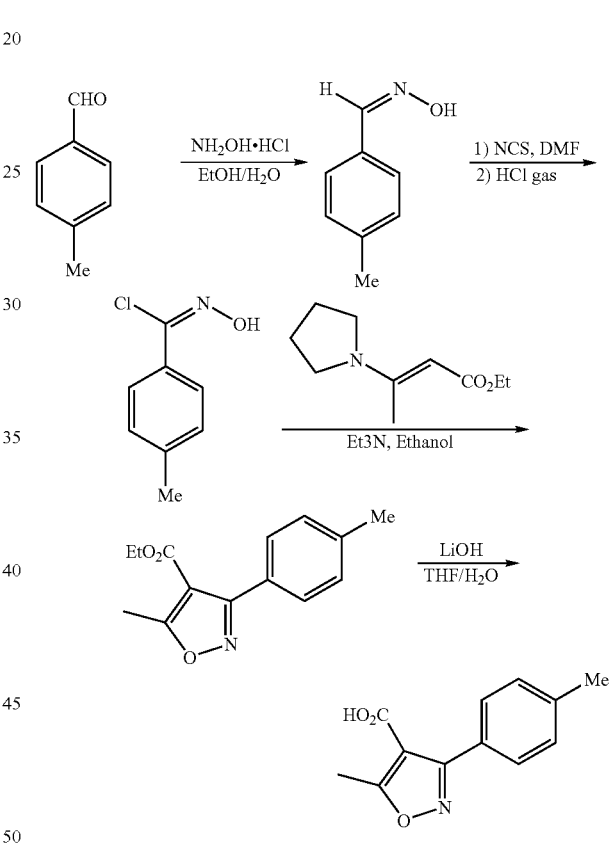

Step V1. To a stirred solution of p-tolualdehyde (8 g, 0.066M) in water (13 ml), 95% absolute alcohol (13 ml) and 25 g of ice, hydroxylamine hydrochloride (4.6 g, 0.066M) was added, followed by 50% sodium hydroxide (5 ml). The reaction mixture was stirred for an hour, acidified with conc.HCl to strongly acidic, and extracted with dichloromethane (3×50 ml). The combined organic layer was dried over anhydrous sodium sulphate and concentrated under vacuum to give pure product, 7.9 g (88%) as yellow liquid.

Step V2. To a stirred solution of the oxime (8 g, 0.0585M) in DMF (30 ml) was added one fifth of N-chlorosuccinimide (7.9 g, 0.0585M). After 10 min HCl gas was bubbled and the temperature was maintained below 35° C. by periodic ice cooling. The rest of NCS was added in portions and the reaction mixture was stirred over night. The reaction mixture was poured into (250 ml) and extract with diethyl ether (3×100 ml). The combined organic layer was washed with water (2×100 ml), dried over anhydrous sodium sulphate and concentrated under vacuum to give pure product, 9.6 g (95%) as yellow solid.

Step V3. To a solution of the enamine of ethyl acetate (9.7 g, 0.053M) and triethylamine (4.8 ml) in absolute alcohol (70 ml) at 0° C. under $N_2$ was added a solution of oxime (9 g, 0.038M) in absolute alcohol (50 ml), drop wise via an addition funnel. The reaction mixture was warmed to room temperature and allowed to stir overnight. The ethanol was removed under vacuum and the residue was taken up in diethyl ether (150 ml) and washed with 1M HCl (75 ml), water (3×50 ml), dried over anhydrous sodium sulphate. The organic layer concentrated under vacuum to give the crude product, 11.4 g (87%), as which was used in the next step without further purification.

Step V4. To a stirred solution of product of V3 (11.4 g, 0.028M) in THF/$H_2O$ (200/50 ml) was added lithium hydroxide (4.6 g, 0.194M). The reaction mixture was stirred at RT for over night and the solvent, THF was removed from the reaction mixture under vacuum. The resulting mass was diluted with water and washed with diethyl ether (2×50 ml). Then the aqueous solution was acidified with sat. Oxalic acid (PH~4) and was extracted with ethyl acetate (2×100 ml). The combined organic layer was dried over anhydrous sodium sulphate, concentrated under vacuum to give the final product, 7 g (69%) as white solid. $^1$H NMR (DMSO-$d_6$): δ 2.42 (3H, s), 2.77 (3H, s), 7.27 (2H, dd), 7.53 (2H, dd), 12.80 (1H, br s). $^{13}$C NMR (DMSO-$d_6$) δ 13.8, 21.3, 107.4, 124.9, 128.8, 129.1, 139.9, 162.5, 167.2, 177.5. MH$^+$=218.

Preparation W. 3-(3,4-difluorophenyl)-5-methylisoxazole-4-carboxylic acid

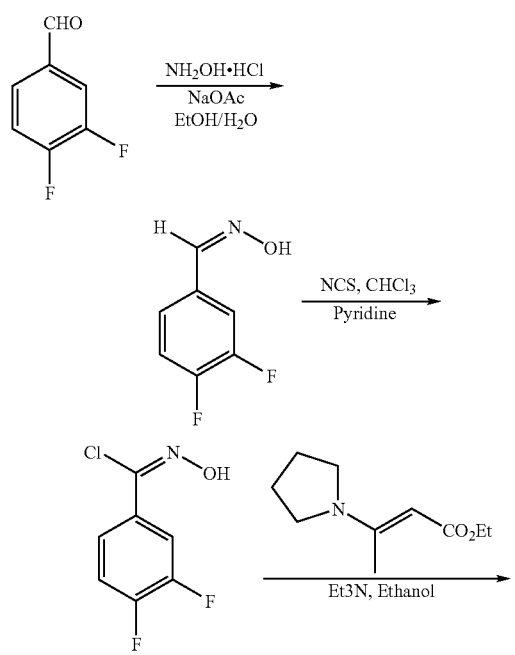

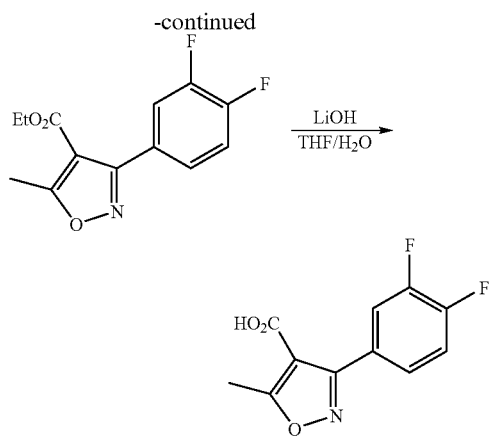

Step W1. To a stirred solution of 3,4-difluorobenzaldehyde (8 g, 0.057M) in ethanol (80 ml) was added the solution of hydroxylamine hydrochloride (4.76 g, 0.068M) in water (20 ml), followed by sodium acetate (4.6 g, 0.057M) in water (30 ml). Then the reaction mixture was heated to 60° C. for 2 hours. The solvent was removed under vacuum and the product was extracted from the aqueous solution with DCM (2×75 ml). The combined organic layer was washed with water (2×50 ml), dried over anhydrous sodium sulphate and concentrated under vacuum to give the pure product, 8.6 g (97%).

Step W2. To a stirred solution of 3,4-difluorobenzaldehyde oxime (8.6 g, 0.055M) in dry CHCl$_3$/THF (100/50 ml) under $N_2$, N-chlorosuccinimide (8.8 g, 0.066M) was added, followed by pyridine (0.5 ml). The reaction mixture was stirred at RT for 2 hours and was concentrated under vacuum. The resulting mass was poured into ice water (250 ml) and extracted with diethylether (3×100 ml). The combined organic layer was washed with water (2×100 ml), dried over anhydrous sodium sulphate and concentrated under vacuum to give the product, 4.8 g (45%).

Step W3. To a solution of the enamine of ethylacetate (5.1 g, 0.027M) and triethylamine (1.9 ml) in absolute alcohol (50 ml) at 0° C. under $N_2$ was added a solution of product of Step W2 (4.8 g, 0.025M) in absolute alcohol (50 ml), dropwise via an addition funnel. The reaction mixture was warmed to RT and stirred overnight. The ethanol was removed under vacuum and the residue was taken up in diethylether (250 ml) and washed with 1M HCl (100 ml), water (3×75 ml), dried over anhydrous sodium sulphate. The organic layer concentrated under vacuum to give the crude product, 5.9 g (87%), which was used in the next step without further purification.

Step W4. To a stirred solution of ester (5.9 g, 0.020M) in THF/$H_2O$ (75/18.75 ml) was added lithium hydroxide (5.2 g, 0.2M). The reaction mixture was stirred at RT for over night and the solvent, THF was removed from the reaction mixture under vacuum. The resulting mass was diluted with water and washed with diethyl ether (2×50 ml). Then the aqueous solution was acidified with sat. Oxalic acid (PH~4) and was extracted with ethyl acetate (2×75 ml). The combined organic layer was dried over anhydrous sodium sulphate, concentrated under vacuum to give the acid, 3.5 g (66%). $^1$H NMR (DMSO-$d_6$): δ 2.80 (3H, s), 7.30 (1H, d), 7.46 (1H, d), 7.55 (1H, d), 12.80 (1H, br s). $^{13}$C NMR (DMSO-$d_6$) δ 13.3, 109.5, 109.5, 118.0, 119.9, 127.2, 127.3, 149.3, 150.8, 152.6, 154.2, 164.2, 177.7. MH$^+$=240.

Preparation X. 3-(3,4-dimethoxyphenyl)-5-methyl-isoxazole-4-carboxylic acid

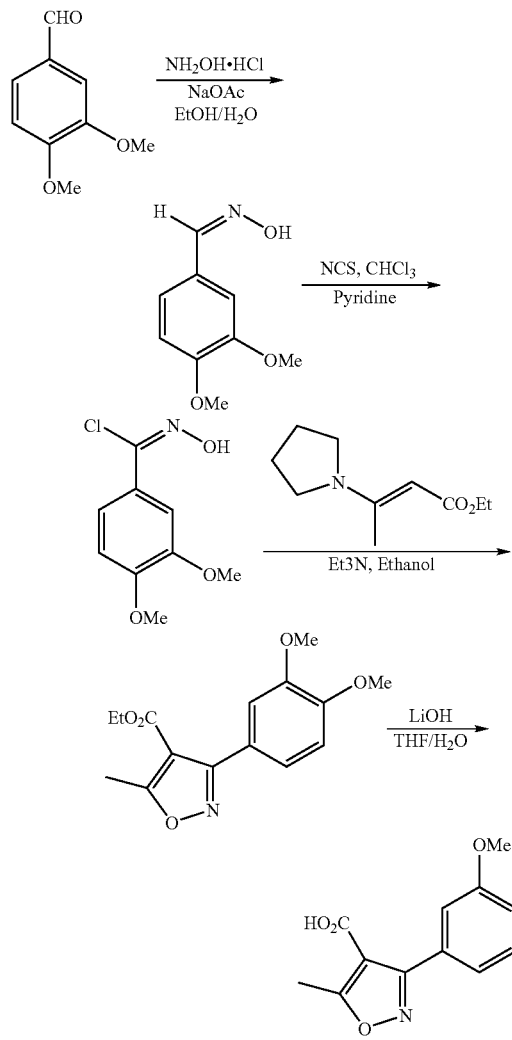

Step X1. To a stirred solution of 3,4-dimethoxybenzaldehyde (8 g, 0.048M) in ethanol (80 ml) was added the solution of hydroxylamine hydrochloride (4 g, 0.057M) in water (16 ml), followed by sodium acetate (4.7 g, 0.057M) in water (30 ml). Then the reaction mixture was heated to 60° C. for 2 hours. The solvent was removed under vacuum and the product was extracted from the aqueous solution with DCM (2×75 ml). The combined organic layer was washed with water (2×50 ml), dried over anhydrous sodium sulphate and concentrated under vacuum to give the pure product, 7.5 g (86%).

Step X2. To a stirred solution of 3,4-dimethoxybenzaldehyde oxime (7.5 g, 0.041M) in dry CHCl$_3$/THF (80/20 ml) under N$_2$, N-chlorosuccinimide (6 g, 0.045M) was added, followed by pyridine (0.5 ml). The reaction mixture was stirred at room temperature for 2 hours and was concentrated under vacuum. The resulting mass was poured into ice water (250 ml) and extracted with diethyl ether (3×100 ml). The combined organic layer was washed with water (2×100 ml), dried over anhydrous sodium sulphate and concentrated under vacuum to give the product, 8.4 g (94%).

Step X3. To a solution of the enamine of ethylacetoacetate (7.1 g, 0.038M) and triethylamine (4.8 ml, 0.034M) in absolute alcohol (80 ml) at 0° C. under N$_2$ was added a solution of product of X3 (8.4 g, 0.038M) in absolute alcohol (50 ml), drop wise via an addition funnel. The reaction mixture was warmed to room temperature and stirred overnight. The ethanol was removed under vacuum and the residue was taken up in diethyl ether (250 ml) and washed with 1M HCl (75 ml), water (3×75 ml), dried over anhydrous sodium sulphate. The organic layer concentrated under vacuum to give the crude product, 8.5 g (75%), which was used in the next step without further purification.

Step X4. To a stirred solution of product of Step X3 (8.5 g, 0.020M) in THF/H$_2$O (80/20 ml) was added lithium hydroxide (6.9 g, 0.2M). The reaction mixture was stirred at RT for over night and the solvent, THF was removed from the reaction mixture under vacuum. The resulting mass was diluted with water and washed with diethyl ether (2×50 ml). Then the aqueous solution was acidified with sat. Oxalic acid (PH~4) and was extracted with ethyl acetate (2×75 ml). The combined organic layer was dried over anhydrous sodium sulphate, concentrated under vacuum to give the final product, 2.9 g (38%). $^1$H NMR (DMSO-d$_6$): δ 2.80 (3H, s), 3.95 (3H, s), 6.95 (1H, d), 7.25 (1H, s), 7.29 (1H, d), 12.80 (1H, br s). $^{13}$C NMR (DMSO-d$_6$) δ 13.1, 55.5, 108.5, 111.2, 112.9, 120.4, 121.9, 148.0, 150.0, 161.7, 162.9, 175.4. MH$^+$=264.

Preparation Y. 3-(4-methoxyphenyl)-5-methylisoxazole-4-carboxylic acid

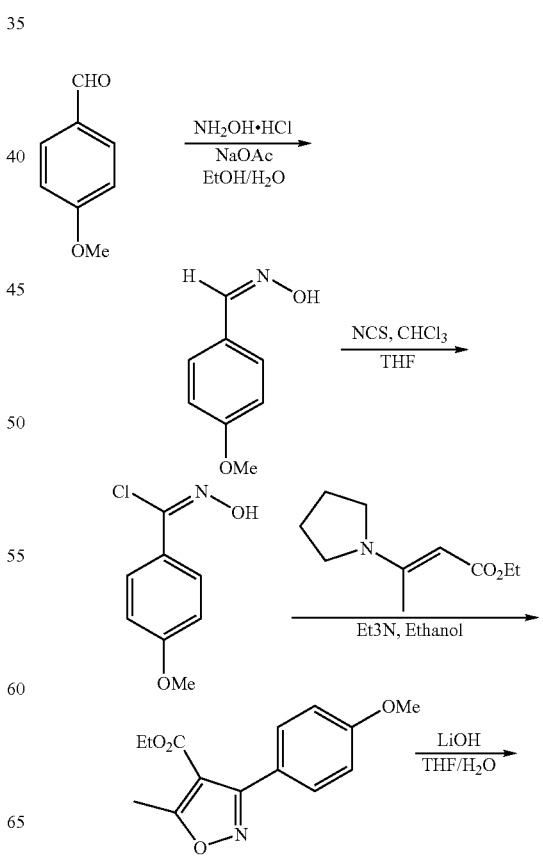

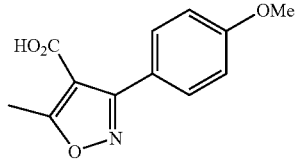

Step Y1. To a stirred solution of 4-methoxybenzaldehyde (10 g, 0.054M) in ethanol (100 ml) was added the solution of hydroxylamine hydrochloride (4.5 g, 0.064M) in water (20 ml), followed by sodium acetate (4.7 g, 0.054M) in water (30 ml). Then the reaction mixture was heated to 60° C. for 2 hours. The solvent was removed under vacuum and the product was extracted from the aqueous solution with DCM (2×75 ml). The combined organic layer was washed with water (2×50 ml), dried over anhydrous sodium sulphate and concentrated under vacuum to give the pure product, 9.8 g (90%).

Step Y2. To a stirred solution of 4-methoxybenzaldehyde oxime (12.9 g, 0.067M) in dry CHCl$_3$/THF (100/50 ml) under N$_2$, N-chlorosuccinimide (12.6 g, 0.077M) was added, followed by pyridine (0.5 ml). The reaction mixture was stirred at RT for 2 hours and was concentrated under vacuum. The resulting mass was poured into ice water (250 ml) and extracted with diethyl ether (3×100 ml). The combined organic layer was washed with water (2×100 ml), dried over anhydrous sodium sulphate and concentrated under vacuum to give the product, 13 g (86%).

Step Y3. To a solution of the enamine of ethylacetoacetate (11.1 g, 0.060M) and triethylamine (7.7 ml, 0.054M) in absolute alcohol (100 ml) at 0° C. under N$_2$ was added a solution of the product of Step Y2 (13 g, 0.054M) in absolute alcohol (100 ml), drop wise via an addition funnel. The reaction mixture was warmed to room temperature and stirred overnight. The ethanol was removed under vacuum and the residue was taken up in diethyl ether (250 ml) and washed with 1M HCl (100 ml), water (3×75 ml), dried over anhydrous sodium sulphate. The organic layer concentrated under vacuum to give the crude product, 11 g (67%), which was used in the next step without further purification. $^1$H NMR (CDCl$_3$): δ 1.27 (3H, t), 2.72 (3H, s), 3.86 (3H, s), 4.26 (2H, q), 6.97 (2H, dd), 7.60 (2H, dd). MH$^+$=262.

Step Y4. To a stirred solution of ester (10 g, 0.033M) in THF/H$_2$O (175/40 ml) was added lithium hydroxide (8 g, 0.33M). The reaction mixture was stirred at room temperature for over night and the solvent, THF was removed from the reaction mixture under vacuum. The resulting mass was diluted with water and washed with diethyl ether (2×50 ml). Then the aqueous solution was acidified with sat. Oxalic acid (PH~4) and was extracted with ethyl acetate (2×75 ml). The combined organic layer was dried over anhydrous sodium sulphate, concentrated under vacuum to give the pure product (8 g, 84%). $^1$H NMR (DMSO-d$_6$): δ 2.69 (3H, s), 7.57 (2H, dd), 7.70 (2H, dd), 12.62 (1H, br s). $^{13}$C NMR (DMSO-d$_6$) δ 13.6, 109.0, 123.8, 128.0, 131.5, 131.7, 161.8, 163.0, 176.3. MH$^+$=234.

Preparations Z to AC

Preparations Z to AC were prepared according to the reference: Michael W. Ratheke, and Patrick Cowan, J. Org. Chem., 1985, 50, 2622.

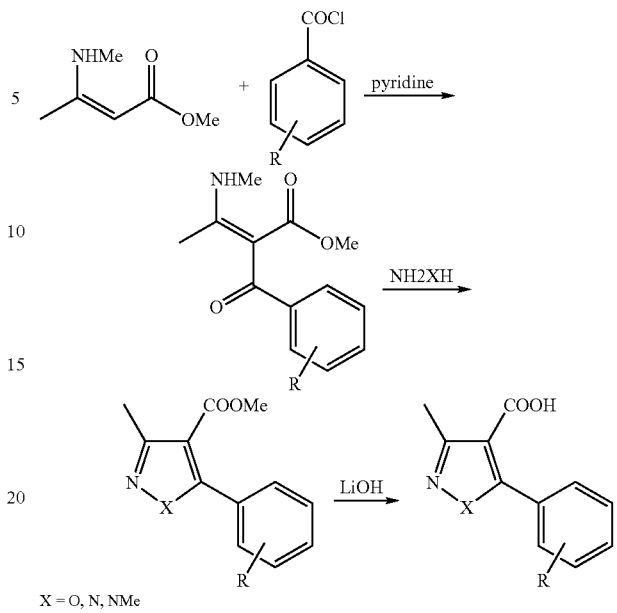

X = O, N, NMe

Preparation Z.
3-Methyl-5-(4-methoxyphenyl)isoxazole-4-carboxylic acid

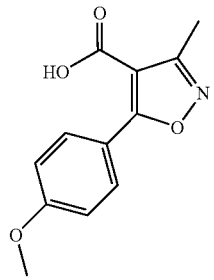

From 1.1 g of 4-methoxybenzoyl chloride, 1.04 g (69.7%) of the title compound was prepared. H$^1$-NMR(CDCl$_3$, 300 MHz): δ 7.90(2H, d, J=9 Hz)), 6.97(2H, d, J=9 Hz), 3.83(3H, S), 2.50(3H, s).

Preparation AA. 3-Methyl-5-(4-dimethylaminophenyl)isoxazole-4-carboxylic acid

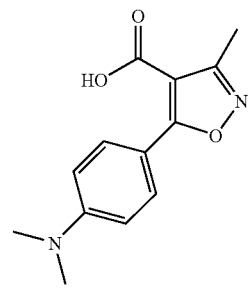

From 2.37 g of 4-methoxybenzoyl chloride, 761 mg (24%) of the title compound was prepared. H$^1$-NMR(CD$_3$OD, 500 MHz): δ 7.87(2H, d, J=9 Hz)), 6.82(2H, d, J=9 Hz), 3.87(3H, S), 3.08(6H, s), 2.45(3H, s).

Preparation AB. 5-(4-methoxyphenyl)-1,3-dimethyl-1H-pyrazole-4-carboxylic acid

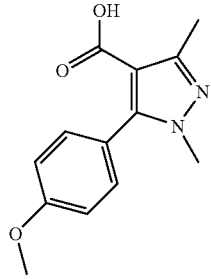

From 3.59 g of 4-methoxybenzoyl chloride, 1.97 g (59%) of a mixture of the title compound(major) and 3-(4-methoxyphenyl)-1,5-dimethyl-1H-pyrazole-4-carboxylic acid(minor) was prepared. $H^1$-NMR(CD$_3$OD, 500 MHz) for the title compound: δ 7.27(2H, d, J=9 Hz), 7.03(2H,d, J=9 Hz), 3.84 (3H, s), 3.60(3H, s), 2.43(3H, s).

Preparation AC. 5-(4-methoxyphenyl)-1-methyl-1H-pyrazole-4-carboxylic acid

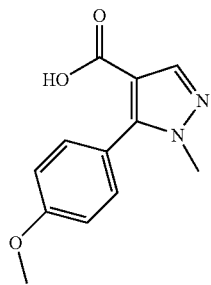

From 1.066 g of 4-methoxybenzoyl chloride, 943 mg (65%) of the title compound was prepared. $H^1$-NMR (CD$_3$OD, 300 MHz): δ 7.55(2H, d, J=9 Hz), 6.97(2H,d, J=9 Hz), 3.86(3H, s), 2.52(3H,s).

Preparation AD. 5-(4-fluorophenyl)-3-methylisoxazole-4-carboxylic acid

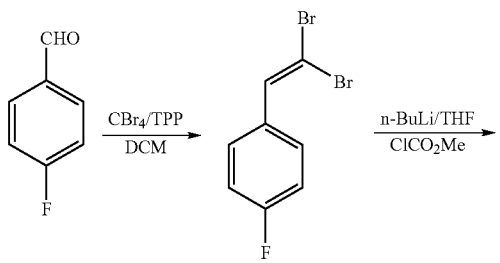

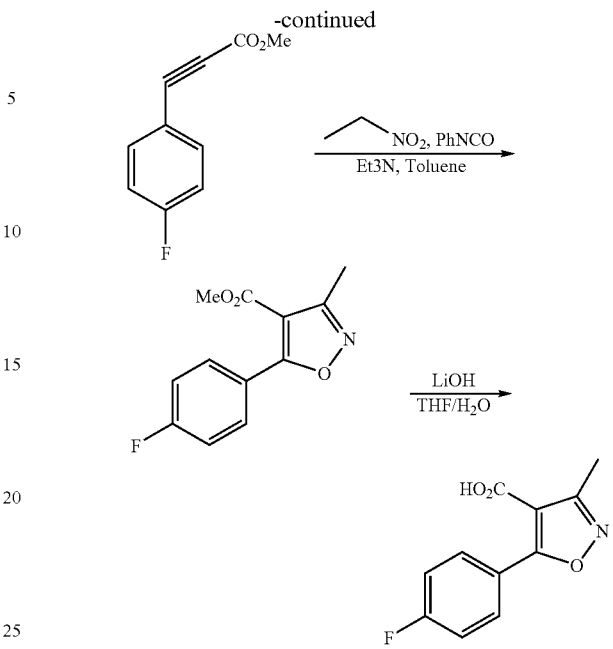

Step AD1. A solution of CBr$_4$ (26.5 g, 0.081M) in dry DCM (100 ml) at 0° C. under nitrogen was treated with PPh$_3$ (42 g, 0.16M) and stirred 1 hour at 0° C. The reaction mixture was treated with 4-fluorobenzaldehyde (5 g, 0.04M) and stirred for 1 hour at 0° C., quenched with water (50 ml). The DCM layer wash with brine solution (2×50 ml) and dried over anhydrous sodium sulphate and concentrated under vacuum to get crude product which was purified by column chromatography over silica gel (60-120) using PE/EtOAC (9.7/0.3) as eluent to afford dibromo compound 10 g (88%).

Step AD2. A solution of dibromo compound (21 g, 0.081M) in dry THF (200 ml) under nitrogen at −78° C. was treated drop wise with n-butyl lithium (2.98M).(59 ml, 0.0178M) and stirred 30 minutes at −78° C. and 30 min at 0° C. The RM was quenched with methyl chloroformate (8.9 ml, 0.113M) at −78° C. and warmed to 0° C. for an hour. The RM was diluted with 1:1 sat.NaHCO$_3$/NH$_4$Cl(aq) (125 ml) and the aqueous layer was extracted with diethyl ether (2×75 ml) The combined organic layer was dried over anhydrous sodium sulphate and concentrated under vacuum to get crude product which was purified by column chromatography over silica gel (60-120) using PE/EtOAC (9.7/0.3) as eluent to afford ester 9.5 g (66%).

Step AD3. To a stirred solution of the product of Step AD2 (9 g, 0.05M) in dry toluene (90 ml) under nitrogen, nitro ethane (8.5 ml, 0.050M) was added, followed by triethylamine (3.4 ml, 0.025M). Then a solution of phenyl isocyanate (6 g, 0.05M) in dry toluene was added to the RM at 80° C. After the addition was over the stirring was continued for overnight at 80° C. The RM was cooled under ice bath, filtered and the filtrate was concentrated under vacuum. The resulting mass was taken in ethyl acetate (75 ml) and washed with water (2×20 ml), 5% NH$_4$OH (40 ml), dried over anhydrous sodium sulphate and concentrated under vacuum to get crude product which was purified by column chromatography over silica gel (60-120) using PE/EtOAC (9.9/0.1) as eluent to afford isoxazole ester 3.7 g (32%).

Step AD4. To a stirred solution of ester (4.7 g, 0.020M) in THF/H$_2$O (90/25 ml) was added lithium hydroxide (4.8 g, 0.2M). The reaction mixture was stirred at RT for over night and the solvent, THF was removed from the reaction mixture under vacuum. The resulting mass was diluted with water and washed with diethyl ether (2×50 ml). Then the aqueous solution was acidified with sat. Oxalic acid (PH~4) and was extracted with ethyl acetate (2*75 ml). The combined organic layer was dried over anhydrous sodium sulphate, concentrated under vacuum to give the pure product (3.5 g, 78%). $^1$H NMR (DMSO-$d_6$): δ 2.49 (3H, s), 7.25 (2H, dd), 8.01 (2H, dd), 12.62 (1H, br s). $^{13}$C NMR (DMSO-$d_6$) δ 12.2, 109.2, 115.9, 116.1, 123.6, 132.1, 161.1, 162.8, 163.3, 165.3, 171.2. $MH^+$=222.

Preparation AE.
5-(4-chlorophenyl)-3-methylisoxazole-4-carboxylic acid

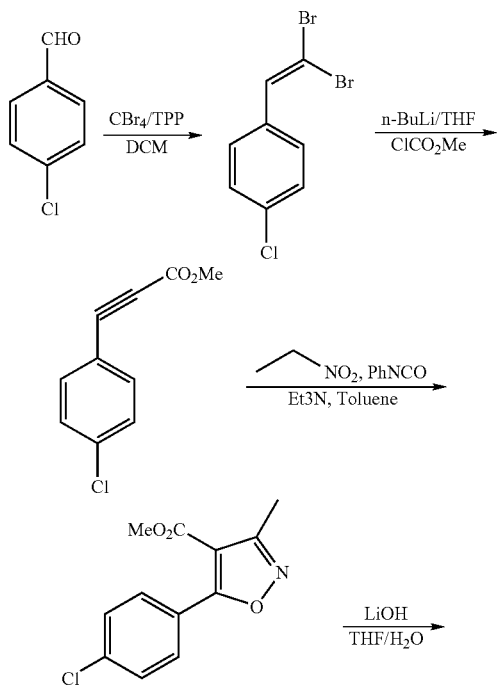

Step AE1. A solution of $CBr_4$ (23.6 g, 0.071M) in dry DCM (100 ml) at 0° C. under nitrogen was treated with $PPh_3$ (36.6 g, 0.16M) and stirred 1 hour at 0° C. The reaction mixture was treated with 4-chlorobenzaldehyde (5 g, 0.04M) and stirred for 1 hour at 0° C., quenched with water (50 ml). The DCM layer wash with brine solution (2×50 ml) and dried over anhydrous sodium sulphate and concentrated under vacuum to get crude product which was purified by column chromatography over silica gel (60-120) using PE/EtOAC (9.8/0.2) as eluent to afford pure dibromide 10 g (95%).

Step AE2. A solution of dibromide (20 g, 0.072M) in dry THF (200 ml) under nitrogen at −78° C. was treated drop wise with n-butyl lithium (2.98M).(53 ml, 0.0158M) and stirred 30 minutes at −78° C. and 30 min at 0° C. The reaction mixture was quenched with methyl chloroformate (5.6 ml, 0.072M) at −78° C. and warmed to 0° C. for an hour. The reaction mixture was diluted with 1:1 sat.$NaHCO_3$/$NH_4Cl$ (125 ml) and the aqueous layer was extracted with diethyl ether (2×75 ml) The combined organic layer was dried over anhydrous sodium sulphate and concentrated under vacuum to get crude product which was purified by column chromatography over silica gel (60-120) using PE/EtOAC (9.7/0.3) as eluent to afford 9.2 g (65%).

Step AE3. To a stirred solution of the product of Step AE2 (6 g, 0.030M) in dry toluene (60 ml) under nitrogen, nitro ethane (2.3 g, 0.030M) was added, followed by triethylamine (2.1 ml, 0.015M). Then a solution of phenyl isocyanate (3.6 g, 0.030M) in dry toluene was added to the reaction mixture at 80° C. After the addition was over the stirring was continued for overnight at 80° C. The reaction mixture was cooled under ice bath, filtered and the filtrate was concentrated under vacuum. The resulting residue was taken in ethyl acetate (75 ml) and washed with water (2×20 ml), 5% $NH_4OH$ (40 ml), dried over anhydrous sodium sulphate and concentrated under vacuum to get crude product which was purified by column chromatography over silica gel (60-120) using PE/EtOAC (9.9/0.1) as eluent to afford 3.8 g (49%)

Step AE4. To a stirred solution of product of Step AE3 (3.8 g, 0.015M) in THF/$H_2O$ (90/25 ml) was added lithium hydroxide (3.6 g, 0.15M). The reaction mixture was stirred at RT for over night and the solvent, THF was removed from the reaction mixture under vacuum. The resulting mass was diluted with water and washed with diethyl ether (2×50 ml). Then the aqueous solution was acidified with sat. Oxalic acid (PH~4) and was extracted with ethyl acetate (2×75 ml). The combined organic layer was dried over anhydrous sodium sulphate, concentrated under vacuum to give the pure product (3.2 g, 89%). $^1$H NMR (DMSO-$d_6$): δ 2.50 (3H, s), 7.54 (2H, dd), 7.96 (2H, dd), 12.62 (1H, br s). $^{13}$C NMR (DMSO-$d_6$) δ 12.6, 110.5, 127.4, 130.1, 132.2, 138.8, 162.9, 165.0, 173.3. $MH^+$=238.

Preparation AF.
5-(3-fluorophenyl)-3-methylisoxazole-4-carboxylic acid

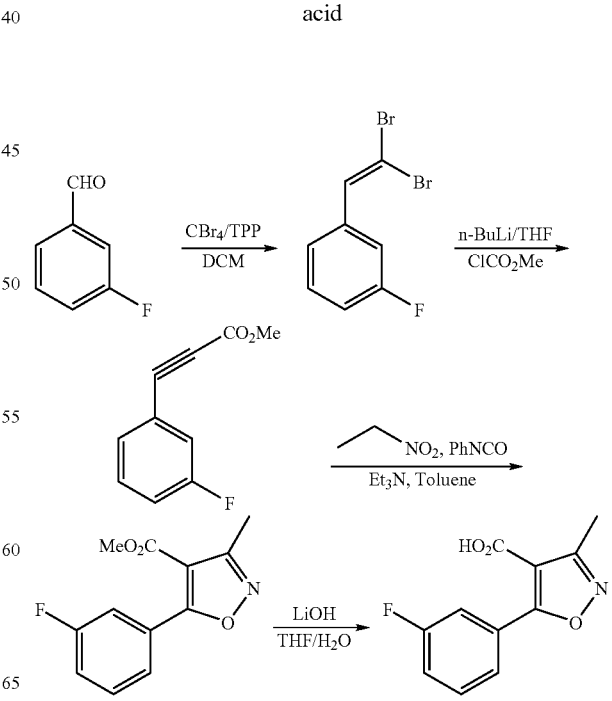

Step AF1. A solution of CBr₄ (42 g, 0.018M) in dry DCM (200 ml) at 0° C. under nitrogen was treated with PPh₃ (67 g, 0.285M) and stirred 1 hour at 0° C. The reaction mixture was treated with 3-fluorobenzaldehyde (8 g, 0.064M) and stirred for 1 hour at 0° C., quenched with water (25 ml). The DCM layer washed with brine solution (2×50 ml) and dried over anhydrous sodium sulphate and concentrated under vacuum to get crude product which was purified by column chromatography over silica gel (60-120) using PE/EtOAC (9.8/0.2) as eluent to afford 13 g (72%).

Step AF2. A solution of dibromide (13 g, 0.072M) in dry THF (200 ml) under nitrogen at −78° C. was treated drop wise with n-butyl lithium (2.98M), (38 ml, 0.1158M) and stirred 30 minutes at −78° C. and 30 min at 0° C. The reaction mixture was quenched with methyl chloroformate (6.6 g, 0.072M) at −78° C. and warmed to 0° C. for an hour. The reaction mixture was diluted with 1:1 sat.NaHCO₃/NH₄Cl (125 ml) and the aqueous layer was extracted with diethyl ether (2×75 ml) The combined organic layer was dried over anhydrous sodium sulphate and concentrated under vacuum to get crude product which was purified by column chromatography over silica gel (60-120) using PE/EtOAC (9.7/0.3) as eluent to afford desired compound 6 g (67%).

Step AF3. To a stirred solution of product of Step AF2 (6.3 g, 0.030M) in dry toluene (65 ml) under nitrogen, nitro ethane (2.7 g, 0.030M) was added, followed by triethylamine (2.5 ml, 0.018M). Then a solution of phenyl isocyanate (4.6 g, 0.030M) in dry toluene was added to the reaction mixture at 80° C. After the addition was over the stirring was continued for overnight at 80° C. The reaction mixture was cooled under ice bath, filtered and the filtrate was concentrated under vacuum. The resulting mass was taken in ethyl acetate (75 ml) and washed with water (2×20 ml), 5% NH₄OH (40 ml), dried over anhydrous sodium sulphate and concentrated under vacuum to get crude product which was purified by column chromatography over silica gel (60-120) using PE/EtOAC (9.9/0.1) as eluent to afford desired compound 4 g (45%).

Step AF4. To a stirred solution of product of Step AF3 (2.5 g, 0.010M) in THF/H₂O (52/10 ml) was added lithium hydroxide (2.5 g, 0.105M). The reaction mixture was stirred at RT for over night and the solvent, THF was removed from the reaction mixture under vacuum. The resulting mass was diluted with water and washed with diethyl ether (2×50 ml). Then the aqueous solution was acidified with sat. Oxalic acid (PH~4) and was extracted with ethyl acetate (2×75 ml). The combined organic layer was dried over anhydrous sodium sulphate, concentrated under vacuum to give the pure product (2.1 g, 89%). ¹H NMR (DMSO-d₆): δ 2.43 (3H, s), 7.45 (1H, d), 7.60 (1H, m), 7.71 (1H, m), 7.77 (1H, m), 12.62 (1H, br s). ¹³C NMR (DMSO-d₆) δ 12.1, 109.9, 116.2, 118.5, 118.7, 129.0, 131.1, 161.2, 163.2, 170.6. MH⁺=222.

Preparation AG.
5-(3-methoxyphenyl)-3-methylisoxazole-4-carboxylic acid

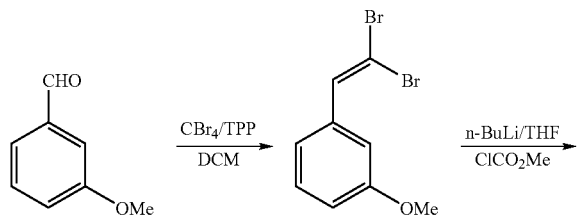

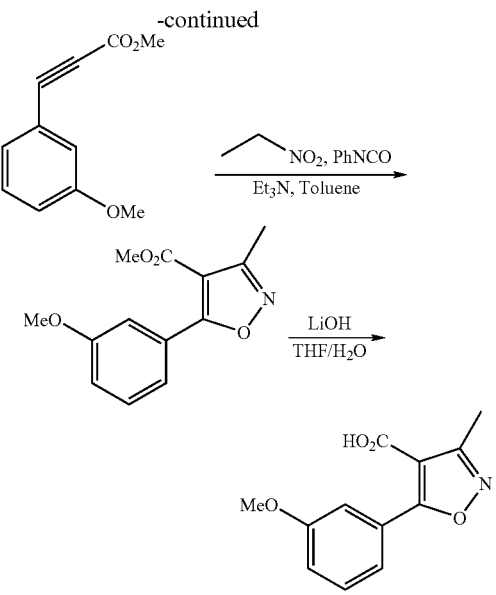

Step AG1. A solution of CBr₄ (48 g, 0.147M) in dry DCM (200 ml) at 0° C. under nitrogen was treated with PPh₃ (76 g, 0.285M) and stirred 1 hour at 0° C. The reaction mixture was treated with 3-methoxybenzaldehyde (10 g, 0.073M) and stirred for 1 hour at 0° C., quenched with water (75 ml). The DCM layer washed with brine solution (2×50 ml) and dried over anhydrous sodium sulphate and concentrated under vacuum to get crude product which was purified by column chromatography over silica gel (60-120) using PE/EtOAC (9.8/0.2) as eluent to afford dibromo compound 20 g (93%)

Step AG2. A solution of the product of Step AG1 (20 g, 0.068M) in dry THF (200 ml) under nitrogen at −78° C. was treated drop wise with n-butyl lithium (2.98M).(51 ml, 0.158M) and stirred 30 minutes at −78° C. and 30 min at 0° C. The RM was quenched with methyl chloroformate (9 g, 0.095M) at −78° C. and warmed to 0° C. for an hour. The reaction mixture was diluted with 1:1 sat.NaHCO₃/NH₄Cl (125 ml) and the aqueous layer was extracted with diethyl ether (2×75 ml). The combined organic layer was dried over anhydrous sodium sulphate and concentrated under vacuum to get crude product which was purified by column chromatography over silica gel (60-120) using PE/EtOAC (9.7/0.3) as eluent to afford pure product 9 g (70%).

Step AG3. To a stirred solution of the product of Step AG2 (6.4 g, 0.030M) in dry toluene (65 ml) under nitrogen, nitro ethane (2.5 g, 0.030M) was added, followed by triethylamine (2.4 ml, 0.018M). Then a solution of phenyl isocyanate (4 g, 0.030M) in dry toluene was added to the reaction materials at 80° C. After the addition was over the stirring was continued for overnight at 80 C. The RM was cooled under ice bath, filtered and the filtrate was concentrated under vacuum. The resulting mass was taken in ethyl acetate (75 ml) and washed with water (2×20 ml), 5% NH₄OH (40 ml), dried over anhydrous sodium sulphate and concentrated under vacuum to get crude product which was purified by column chromatography over silica gel (60-120) using PE/EtOAC (9.9/0.1) as eluent to afford pure product 4 g (47%).

Step AG4. To a stirred solution of product of Step AG3 (4.5 g, 0.018M) in THF/H₂O (90/10 ml) was added lithium hydroxide (4.3 g, 0.180M). The reaction mixture was stirred at room temperature for over night and the solvent was removed from the reaction mixture under vacuum. The resulting mass was diluted with water and washed with diethyl ether (2×50 ml). Then the aqueous solution was acidified with sat. Oxalic acid (PH~4) and was extracted with ethyl acetate (2×75 ml). The combined organic layer was dried over anhydrous sodium sulphate, concentrated under vacuum to give the pure product 3.8 g (89%). $^1$H NMR (DMSO-d$_6$): δ 2.56 (3H, s), 3.87 (3H, s), 7.11 (1H, dd), 7.43 (1H, t), 7.48 (1H, s), 7.53 (1H, d), 12.15 (1H, br s). $^{13}$C NMR (DMSO-d$_6$) δ 12.3, 55.4, 107.3, 114.3, 117.7, 121.8, 127.7, 129.5 159.3 161.2, 167.3, 174.2. MH$^+$=234.

Preparation AH.
5-(4-bromophenyl)-3-methylisoxazole-4-carboxylic acid

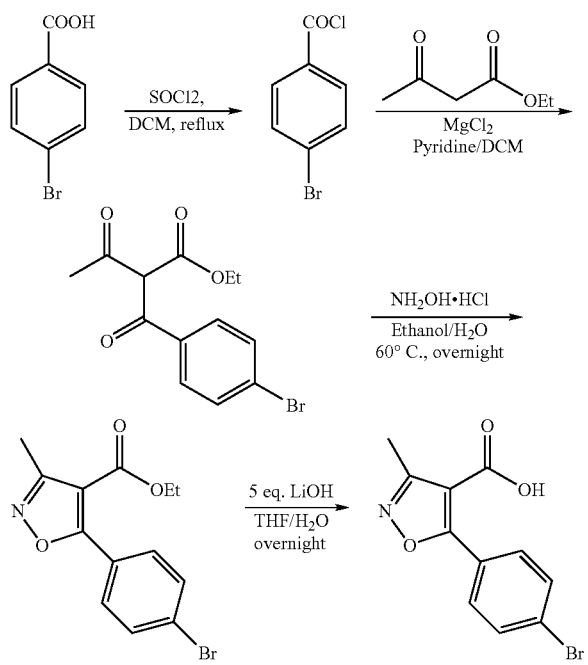

Step AH1. To a suspension of 4-bromobenzoic acid (10 g, 0.0494M) in dry DCM (100 mL) under N$_2$ at 0° C., thionyl chloride (9 ml, 0.0745M) was added in drop wise. After the addition was over, the reaction mixture was heated to reflux at 50° C. for overnight. Then the reaction mixture was concentrated under vacuum to get the product, 10.5 g (96%).

Step AH2. To a stirred suspension of dried MgCl$_2$ (4.55 g, 0.0478M) in dry DCM under nitrogen, ethylacetoacetate (6 ml, 0.0478M) was added. Then the reaction mixture was cooled using ice bath and pyridine 80 ml was added, stirred for 15 min. A solution of (10.5 g, 0.0458M) in dry DCM was added in drop wise at 0° C. and stirred for an hour. The reaction mixture was quenched with 5M HCL (15 ml) and extracted with diethyl ether (2×75 ml) The combined organic layer was-washed with water (2×50 ml) and the brine solution (2×50 ml), dried over anhydrous sodium sulphate and concentrated under vacuum to get the crude product which was purified by column chromatography over silica gel (60-120) using PE/EtOAC (9.8/0.2) as a eluent to afford pure product 6.8 g (45%).

Step AH3. To a stirred solution of the product of Step AH2 (6.8 g, 0.021M) in absolute alcohol (40 ml) was added hydroxylamine hydrochloride salt (6 g, 0.068M) in water (30 ml). Then the reaction mixture was heated to 60° C. for overnight and concentrated under vacuum to remove ethanol. The resulting residue diluted with water (30 ml), extracted with diethyl ether (2*100 ml). The combined organic layer was washed with dilute sodium hydroxide solution until the alkaline extracts gave no precipitates upon acidification, then with water, dried over anhydrous sodium sulphate and concentrated under vacuum to get the crude product which was purified by column chromatography over silica gel (60-120) using PE/EtOAC (9.8/0.2) as a eluent to afford pure compound 3.2 g (47%).

Step AH4. To a stirred solution of ester (3.2 g, 0.010M) in THF/H$_2$O (79/35 ml) was added lithium hydroxide (2.4 g, 0.10M). The reaction mixture was stirred at room temperature for over night and the solvent, THF was removed from the reaction mixture under vacuum. The resulting mass was diluted with water and washed with diethyl ether (2×50 ml). Then the aqueous solution was acidified with sat. Oxalic acid (PH~4) and was extracted with ethyl acetate (2×75 ml). The combined organic layer was dried over anhydrous sodium sulphate, concentrated under vacuum to give the pure product 2.8 g (96%). $^1$H NMR (DMSO-d$_6$): δ 2.52 (3H, s), 7.37 (2H, dd), 7.91 (2H, dd), 12.42 (1H, br s). $^{13}$C NMR (DMSO-d$_6$) δ 12.0, 110.0, 126.6, 127.2, 131.7, 132.5, 162.4, 164.4, 172.7. MH$^+$=282.

Preparations AI and AJ

Preparation of 5-alkyl(longer than methyl)-3-arylisoxazole-4-carboxylic acids were prepared according to the reference: N. R. Natale, John I. McKenna, Chorng-Shyr Niou, and Mark Borth, J. Org. Chem., 1985, 50, 5660.

Preparation AI.
3-Phenyl-5-ethylisoxazole-4-carboxylic acid

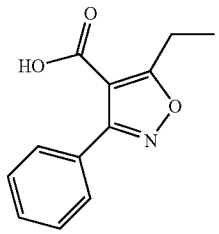

From 5 g of 3-phenyl-5-methylisoxazole-4-carboxylic acid, 4.4 g (82%) of the title compound was prepared. H$^1$-NMR(CD$_3$OD, 500 MHz): δ 7.65~7.64(2H, m), 7.53-7.46(2H,m), 3.21(2H, m), 1.39(3H, m).

Preparation AJ. 5-(2-(2-methoxyethoxy)ethyl)-3-(4-methoxyphenyl)isoxazole-4-carboxylic acid

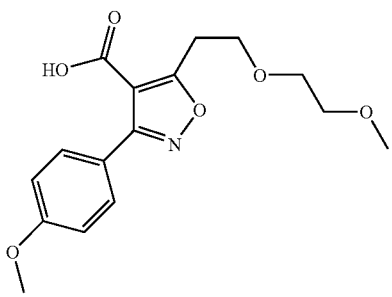

From 1.175 g of 3-(4-methoxyphenyl)-5-methylisoxazole-4-carboxylic acid, 1.2 g (74%) of the title compound was prepared. $H^1$-NMR(CD$_3$OD, 500 MHz): δ 7.61(2H, d), 7.01 (2H,d), 3.91(2H, t), 3.86(3H,s), 3.65(2H, t), 3.55(2H, t), 3.44 (2H,t), 3.35(3H,s).

Preparation AK. 3-(4-methoxyphenyl)-5-methyl-isothiazole-4-carboxylic acid

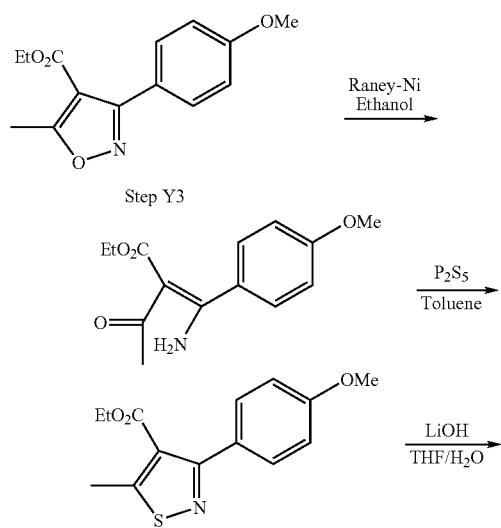

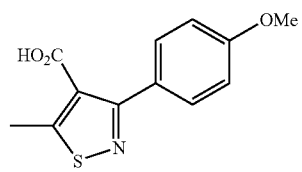

Step AK1. To the isoxazole ester (40 g, synthesized as described in Steps Y1-Y3 of Preparation Y) dissolved in ethanol (400 ml), 10% Raney-Ni in ethanol was added and the reduction was carried out at 5 kg/cm$^2$ pressure in Parr's apparatus. After 2 hours, the catalyst was removed by filtration and the filtrate was concentrated under reduced pressure to afford 34 g (90%) vinyl amine.

Step AK2. To the vinyl amine (34 g, 0.0129M) dissolved in dry toluene (350 ml) was added chloranil (31.8 g, 0.123M) followed by P$_2$S$_5$ (57.36 g, 0.258M). The mixture was refluxed with an efficient stirring for 45 minutes. After cooling the reaction mixture was filtered and the filtrate was concentrated under reduce pressure. The resulting residue was purified by column chromatography (20% PE/EtOAC) to afford the pure ester, 5.5 g (15%).

Step AK3. To the ester obtained in Step AK2 (5.5 g, 0.0198M) dissolved in 50 ml THF/H$_2$O (4:1), NaOH (7.9 g, 0.19M) dissolved in 10 ml of H$_2$O was added. The reaction mixture was heated to 70° C. and allowed to stir overnight. The THF was removed under reduce pressure and the aqueous layer was acidified using citric acid to pH-4 and extracted with EtOAC to afford pure acid 4.9 g (95%). $^1$H NMR (DMSO-d$_6$): δ 2.66 (3H, s), 3.80 (3H, s), 7.00 (2H, dd), 7.51 (2H, dd), 12.80 (1H, br s). $^{13}$C NMR (DMSO-d$_6$) δ 13.3, 113.8, 128.3, 128.3 129.9, 160.2, 165.6, 167.4, 168.1. MH$^+$=250.

Preparation AL. 3-(3-fluorophenyl)-5-methylisothiazole-4-carboxylic acid

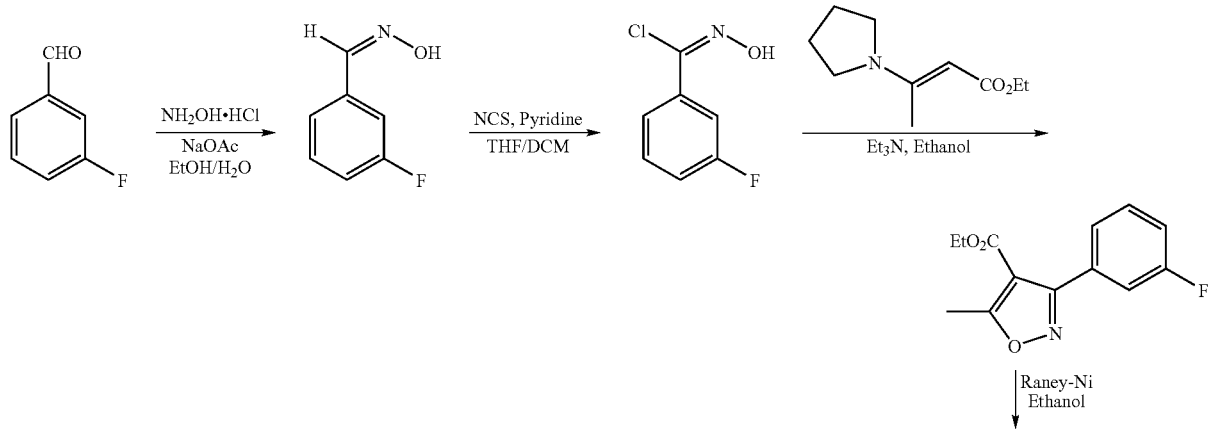

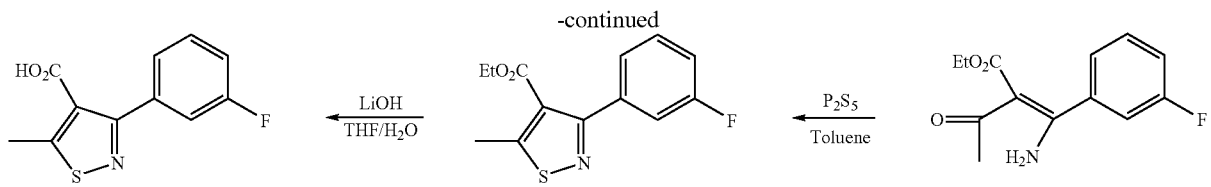

Step AL1. To a stirred solution of m-fluorobenzaldehyde (10 g, 0.080M) in ethanol (80 ml) was added the solution of hydroxylamine hydrochloride (6.72 g, 0.096M) in water (16 ml), followed by sodium acetate (45.18 g, 0.55M) in water (200 ml). The reaction mixture was allowed to stir for two hours. The solvent was removed under reduce pressure and extracted with chloroform (3×150 ml). The combined organic layer was dried over anhydrous sodium sulphate, concentrated under vacuum to afford 10 g white solid (90% crude). The oxime obtained was directly used for next step.

Step AL2. To a stirred solution of oxime (13.4 g, 0.096M) in dry CHCl$_3$/THF (130/100 ml) under N$_2$, N-chlorosuccinimide (15.4 g, 0.115M) was added, followed by pyridine (15 drops). The reaction mixture was stirred at room temperature for 2 hours and was concentrated under vacuum. The resulting residue was poured into ice water (250 ml) and extracted with diethyl ether (3×100 ml). The combined organic layer was washed with water (100 ml), dried over anhydrous sodium sulphate and concentrated under vacuum to give the crude product, 14.1 g (84%), which is taken for the next step.

Step AL3. To a stirred solution of the enamine of ethylacetoacetate (9.17 g, 0.05M) and triethylamine (3.8 ml) in absolute alcohol (100 ml) at 0° C. under N$_2$ was added a solution of the product of Step AL2 (8.75 g, 0.05M) in absolute alcohol (50 ml), drop wise via an addition funnel. The reaction mixture was warmed to room temperature and stirred overnight. The ethanol was removed under vacuum and the residue was taken up in diethyl ether (250 ml) and washed with 1.5N HCl, water (3×75 ml) and dried over anhydrous sodium sulphate. The organic layer concentrated under vacuum to give the crude product, 5 g (73%), of isoxazole ester.

Step AL4. To the isoxazole ester (5 g, 0.02M) is dissolved in ethanol (50 ml), 10% Raney-Ni in ethanol was added and the reduction was carried out at 5 kg/cm$^2$ pressure in a parr's apparatus. After two hours, the catalyst was removed by filtration. The filtrate was concentrated under reduce pressure to afford 4.5 g (90%) of vinyl amine.

Step AL5. To a solution of Vinyl amine (4.5 g, 0.017M) in toluene, P$_2$S$_5$ (5.16 g, 0.023M) was added. The reaction mixture was refluxed with efficient stirring for 30 minutes. After cooling the reaction mixture was filtered and the filtrate was concentrated under reduced pressure. The resulting residue was purified by column chromatography using Pet ether/EtOAc (9:1) as an eluent to afford pure product 1.4 g (28%).

Step AL6. To the ester obtained in Step AL5 (1.4 g, 0.02M) dissolved in 10 ml THF/H$_2$O (4:1), NaOH (2 g, 0.19M) dissolved in 2 ml of H$_2$O was added. The reaction mixture was heated to 70° C. and allowed to stir overnight. The THF was removed under reduce pressure and the aqueous layer was acidified using citric acid to pH-4 and extracted with EtOAC to afford pure acid, 1.1 g (95%). $^1$H NMR (DMSO-d$_6$): δ 2.76 (3H, s), 7.12 (1H, t), 7.29 (1H, t), 7.32 (1H, s), 7.34 (7.37, m), 12.72 (1H, br s). MH$^+$=238.

Preparation AM. (8-chloro-1-methyl-1,2,3,4-tetrahydroquinolin-6-yl)methanamine

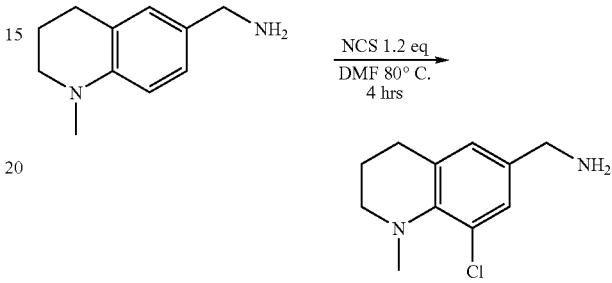

(8-Chloro-1-methyl-1,2,3,4-tetrahydroquinolin-6-yl) methanamine was synthesized from (1-methyl-1,2,3,4-tetrahydroquinolin-6-yl)methanamine (available from ASDI) by following a literature procedure (Kato, S. et al. *J. Heterocycl. Chem.* 1996, 33, 1171-1178). The product was purified by preparative HPLC. LCMS (method B) RT 0.208 min., MH$^{3O}$ 211. $^1$H NMR (500 MHz, CD$_3$OD) δ 7.36 (s, 1 H), 7.16 (s, 1 H), 4.01 (s, 2 H), 3.27 (t, J=5.2 Hz, 2 H), 3.00 (s, 3 H), 2.88 (t, J=6.7 Hz, 2 H), 1.99 (m, 2 H).

Preparation AN. 4-amino-3,5-dimethylbenzylamine

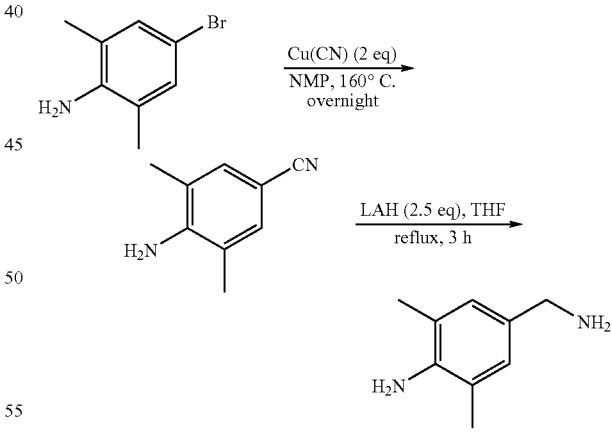

Step AN1. The mixture of 4-bromo-2,6-dimethylaniline (1.90 g, 9.50 mmol) and copper (I) cyanide (1.71 g, 19.1 mmol) in NMP (25 mL) was stirred at 160° C. overnight. The reaction mixture was cooled to room temperature. Water (10 mL) and ammonium hydroxide (10 mL) were added and the product was extracted with ethyl acetate (2×50 mL). The product was purified by flash chromatography (DCM) to give 1.19 g (86%, theoretical yield 1.39 g). LCMS (method B) RT 1.925 min., MH$^{3O}$ 147. $^1$H NMR (500 MHz, CDCl$_3$) δ 7.22 (s, 2 H), 2.18 (s, 6 H).

Step AN2. To the suspension of 0.26 g of lithium aluminum hydride in 30 mL of THF was added dropwise a solution of 0.49 g of 4-amino-3,5-dimethylbenzonitrile in 5 mL of THF. The reaction mixture was stirred at reflux for 3 hours and cooled to room temperature. The reaction mixture was quenched with 1.0 mL of 1.0 N NaOH aqueous solution. The precipitate was filtered off and the solvent was evaporated in vacuo to provide the crude product, which can be used without purification. A portion of the crude product was purified by preparative HPLC. LCMS (method B) RT 0.152 min., (2M+H)$^+$ 301. $^1$H NMR (500 MHz, CD$_3$OD) δ 7.04 (s, 2 H), 3.95 (s, 2 H), 2.25 (s, 6 H).

Preparation AO. Propyl 4-(aminomethyl)-2-chloro-6-methylphenylcarbamate

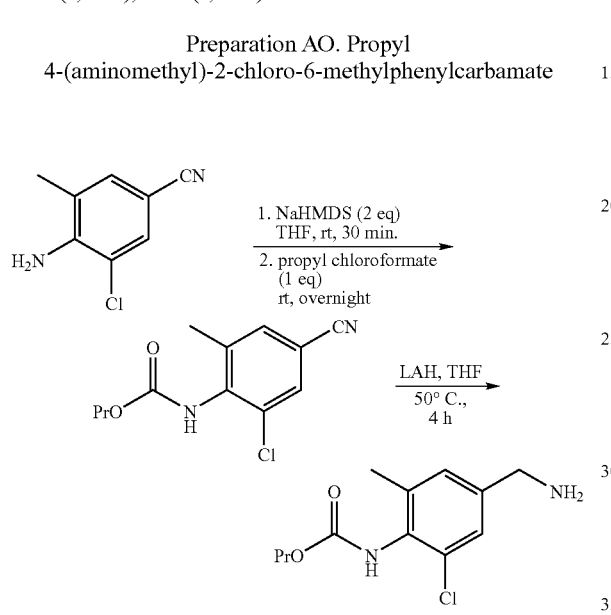

The procedure is exactly the same as preparing 4-acetamido-3-chloro-5-methylbenzylamine (Preparation D), except that propyl chloroformate was used instead of acetyl chloride.

Step AO1. See Preparation D, Step D1. LCMS (method B) RT 2.46 min., MH$^+$253. $^1$H NMR (500 MHz, CDCl$_3$) δ 7.57 (s, 1 H), 7.45 (s, 1 H), 6.40 (s, 1 H), 4.14 (t, J=6.7 Hz, 2 H), 2.36 (s, 3 H), 1.70 (m, 2 H), 0.96 (t, J=7.5 Hz, 3 H).

Step AO2. See Preparation D, Step D2. The title compound was used without further purification. LCMS (method B) RT 1.72 min., (2M+H)$^+$513.

Preparation AP. 3-Chloro-4-amino-5-iodobenzylamine

To 3-Chloro-4-aminobenzylamine (200 mg, 1.28 mmol) in methanol (5 mL) was added Iodine monochloride (230 mg, 1.42 mmol). The mixture was stirred for 1 hour, then purified by HPLC to give 3-chloro-4-amino-5-iodobenzylamine (150 mg, 42%).

Preparation AQ. α-methyl-4-amino-3,5-dichlorobenzylamine

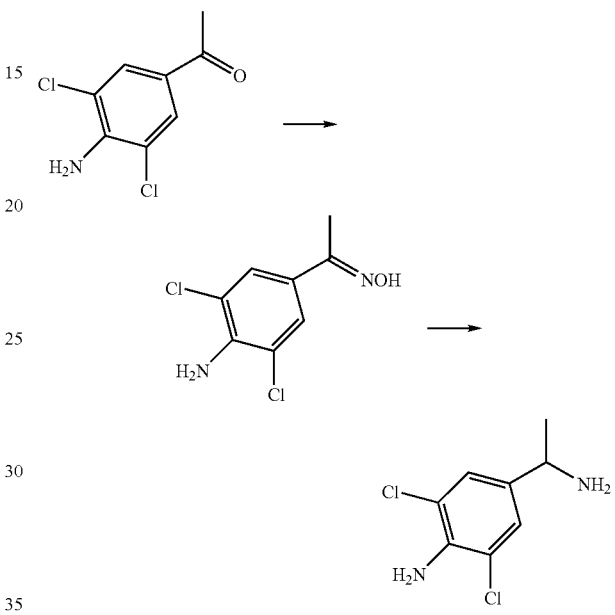

Step AQ1. A mixture of 4-amino-3,5-dichloroacetophenone (4.06 g, 20 mmol) and hydroxylamine (660 mg, 20 mmol) was stirred in THF (30 mL) overnight. After the solvent was removed, the oxime was obtained as a white solid (4.72 g, 100%).

Step AQ2. The oxime (219 mg, 1 mmol) and borane-methyl sulfide complex (370 mg, 5 mmol) was refluxed in THF overnight. The excess reagent was quenched with methanol. After the solvent was removed, the residue was purified by flash chromatography with DCM, then 20% MeOH in DCM. α-Methyl-4-amino-3,5-dichlorobenzylamine was obtained (35 mg, 17%).

Preparation AR. 3-chloro-5-bromo-4-(propylamino)-benzylamine

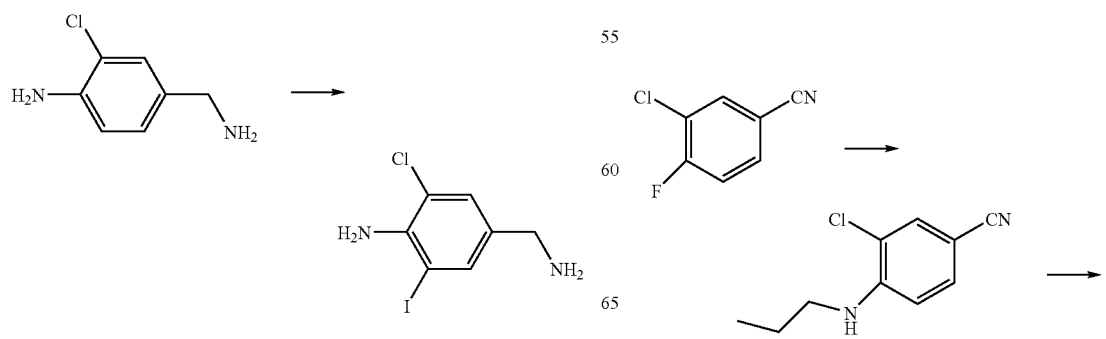

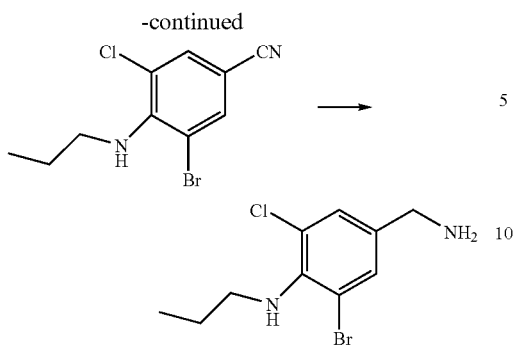

Step AR1. A mixture of 3-chloro-4-florobenzonitrile (312 mg, 2 mmol) and propylamine (236 mg, 4 mmol) in THF (4 mL) was heated at 50° C. overnight. After the solvent was removed, the residue was purified by flash chromatography with DCM to give 3-chloro-4-(propylamino)benzonitrile (365 mg, 94%).

Step AR2. To 3-chloro-4-(propylamino)benzonitrile (365 mg, 1.87 mmol) in MeOH (10 ml) was added bromine (300 mg, 1.87 mmol) in MeOH (2 mL) dropwise. After stirred for 30 minutes, the solvent was removed and crude 3-chloro-5-bromo-4-(propylamino)-benzonitrile was obtained (549 mg, 100%).

Step AR3. To crude 3-chloro-5-bromo-4-(propylamino)-benzonitrile (450 mg, 1.65 mg) in dry THF (15 mL) was added lithium aluminum hydride (200 mg, 5.3 mmol) in portion. After stirred at RT for 3 hours, sodium sulfate decahydrate (1.7 g, 5.3 mmol) was added in portion and the mixture was stirred for 30 minutes. The solid was filtered off and the filtration was added to a silicon gel column and trapped there for 24 hours. Flash chromatography with DCM, then 20% MeOH in DCM, then 50% MeOH in DCM gave 3-chloro-5-bromo-4-(propylamino)-benzylamine (121 mg, 26.4%). $^1$H NMR (CD$_3$OD): δ 1.04 (t, 3H), 1.66 (m, 2H), 3.34 (t, 2H), 3.80 (s, 3H), 7.43 (s, 1H), 7.57 (s, 1H).

Preparation AS.
4,6-dibromo-2,3-dihydro-1H-indene-1,5-diamine

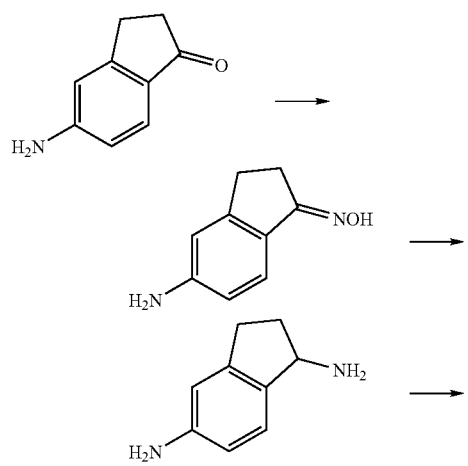

Step AS1. A mixture of 5-aminoindan-1-one (441 mg, 3 mmol) and hydroxylamine hydrochloride (350 mg, 5 mmol) in THF (20 mL) and water (2 mL) was stirred overnight. After the solvents was removed and residue (crude 5-aminoindan-1-one oxime) was dried in vacuum (100%).

Step AS2. A mixture of crude 5-aminoindan-1-one oxime (486 mg, 3 mmol) and borane-methyl sulfide complex (1.2 g, 16 mmol) was refluxed in THF for 3 days. The excess reagent was quenched with methanol. After the solvent was removed, the residue was purified by flash chromatography with DCM, then 20% MeOH in DCM, then 50% MeOH in DCM to give 2,3-dihydro-1H-indene-1,5-diamine.

Step AS3. To 2,3-dihydro-1H-indene-1,5-diamine (30 mg, 0.2 mmol) in MeOH (2 mL) was added bromine (60 mg, 0.4 mmol) in MeOH (1 mL). After stirred for 30 minutes, the solvent was removed and residue was purified by HPLC to give 4,6-dibromo-2,3-dihydro-1H-indene-1,5-diamine (8 mg).

Preparation AT.
4-acetamido-3,5-dichloro-benzylamine

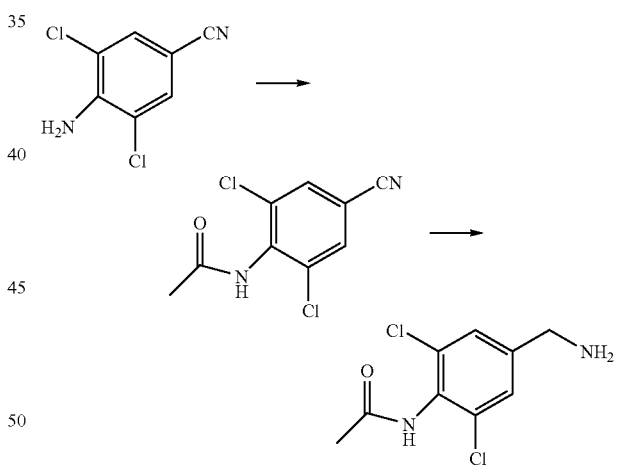

Step AT1. To a solution of 3,5-dichloro-4-amino-benzonitrile (187 mg, 1 mmol) in 4 mL of THF at room temperature was added 2.2 mL of 1.0 M NaHMDS in THF. The resulting reaction mixture was stirred at room temperature for 30 min., at which time acetyl chloride (3.1 mmol) was added. DCM (100 mL) and water (100 mL) were added to the reaction mixture after being stirred overnight, followed by the addition of 5 mL of 1.4 N HCl aqueous solution. Layers were separated and the aqueous layer was extracted with DCM (2×100 mL). The extracts were combined and solvents were evaporated in vacuo. The residue was purified by HPLC to give 4-acetamido-3,5-dichloro-benzonitrile.

Step AT2. To a solution of 4-acetamido-3,5-dichloro-benzonitrile (114 mg, 0.5 mmol) in 5 mL of THF was added lithium aluminum hydride (120 mg, 3.2 mmol) in portion and the resulting mixture was stirred for 3 hours. Sodium sulfate decahydrate (1 g, 3.2 mmol) was added in portion and the mixture was stirred for 30 minutes. The solid was filtered off and the filtration was concentrated. Residue was purified by HPLC to give 4-acetamido-3,5-dichloro-benzylamine (35 mg, 30%).

Preparation AU. tert-butyl methylthiocarbonoimidoylcarbamate

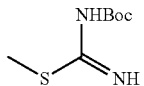

To a rapidly stirred suspension of S-Methylisothiourea hemisulfate (60.8 g, 0.437mol) in CH$_2$Cl$_2$ (600 mL) was added 2N NaOH (300 mL, 0.6 mol). This was cooled to 0° C. on an ice bath, and a solution of di-tert-butyl dicarbonate (43.2 g, 0.198 mol) was added dropwise over 6 h. Upon completion of the addition, the mixture was stirred an additional 20 min, diluted with 1 L CH$_2$Cl$_2$ and the phases were separated. The organic portion was washed with water (2×500 ml) and dried over Na$_2$SO$_4$. Filtration and concentration provided the desired tert-butyl methylthiocarbonoimidoylcarbamate as a white solid (35.5 g, 0.187 mol, 94% yield based on Boc$_2$O).

Preparation AV. tert-butyl N-(3-(4-methoxyphenyl)-5-methylisoxazole-4-carbonyl)(methylthio)carbonoimidoylcarbamate

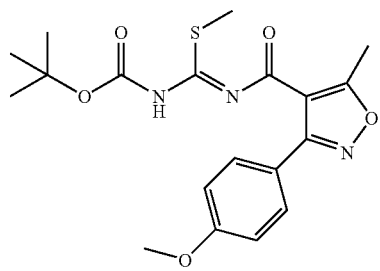

A mixture of tert-butyl methylthiocarbonoimidoylcarbamate (Preparation AU, 0.98 g, 5.16 mmol), 3-(4-methoxyphenyl)-5-methyl-4-isoxazolecarboxylic acid (Preparation Y, 1.17 g, 5 mmol), EDCI (1.2 g, 6.26 mmol) and DIPEA (1 g, 7.75 mmol) in DCM (30 mL) was stirred for 3 hours. The solvent was concentrated by rotovap and residue was purified by column with EtOAc/DCM (5/95) as the eluant. The product was obtained as a white solid (1.2 g, 60%). $^1$H NMR (CD$_3$OD): δ 1.52 (s, 9H), 1.89 (s, 3H), 2.76 (s, 3H), 3.86(s, 3H), 7.00,7.02 (d, 2H), 7.47,7.49 (d, 2H). MH$^+$=406.19

Preparation AW. tert-butyl N-(3-(4-methoxyphenyl)-5-methylisothiazole-4-carbonyl)(methylthio)carbonoimidoylcarbamate

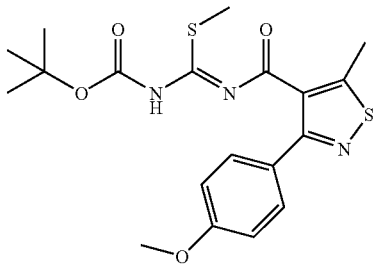

By analogy to the synthesis of the compound of preparation AV, but using the compound of preparation AK, tert-butyl N-(3-(4-methoxyphenyl)-5-methylisothiazole-4-carbonyl)(methylthio)carbonoimidoylcarbamate was prepared as a white solid. $^1$H NMR (CDCl$_3$): δ 1.51 (s, 9H), 1.71 (s,3H), 2.73 (s, 3H), 3.82(s, 3H), 6.89,6.91 (d, 2H), 7.44,7.46 (d, 2H). MH$^+$=422.18

SPECIFIC EMBODIMENTS

EXAMPLE 1

(R)-N-(amino(1-(naphthalene-1-yl)ethylamino)methylene)-5-methyl-3-phenylisoxazole-4-carboxamide

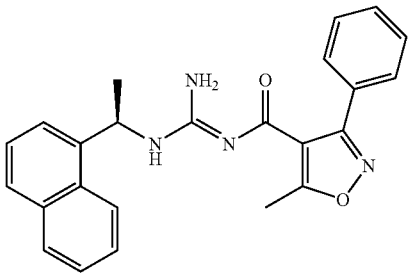

The title compound was prepared on solid support as outlined in Scheme 1.

Step 1A.

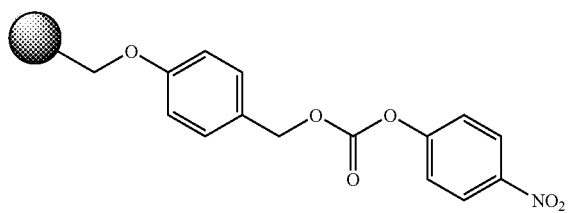

To a 1000 ml round bottom flask was added Wang resin (30 g, 39 mMol, 1.0 eq), anhydrous dichloromethane (DCM, 400 ml), and p-nitrophenyl chloroformate (19.65 g, 97.5 mMol,). To the resulting suspension was slowly added 4-methylmorpholine (12.9 ml, 117 mMol,) at room temperature. The mixture was shaken at room temperature for 12 hours, then filtered and washed with DCM (4×150 ml), ether (2×150 ml), dried in vacuo overnight to afford 38 g resin.

Step 1B.

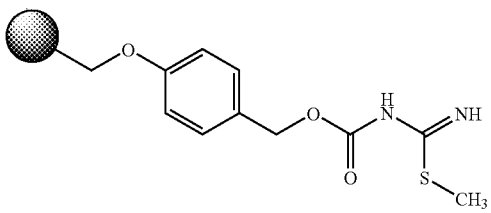

To a suspension of 14 g (18.2 mMol,) of the resin prepared in Step 1B and 2-methyl-2-thiopseudourea sulfate (26.5 g, 95 mMol,) in 400 ml of anhydrous DMF was added cesium carbonate (31 g, 95 mMol,). The resulting mixture was shaken at room temperature for 60 hrs. Drained and washed with DMF (3×300), H$_2$O (3×300 ml), DMF (2×300 ml), THF (3×300 ml), MeOH (3×300 ml), dried in vacuo overnight to afford 12.8 resin.

Step 1C.

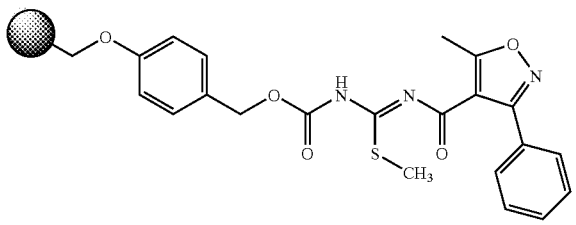

5 g of the resin prepared in Step 1B was suspended in 50 ml of anhydrous N-methylpyrrolidinone (NMP). To the suspension 5.587 g (27.5 mMol) of 5-methyl-3-phenylisoxazole-4-carboxylic acid, 14.3 g of PyAOP (27.5 mMol), and 4.8 ml (27.5 mMol) of diisopropylethylamine (DIEA) were added at room temperature. The resulting mixture was shaken at room temperature for 2 days. The mixture was drained, and washed with DMF (3×50 ml), THF (3×50 ml), MeOH (3×50 ml), dried in vacuo overnight. 35 mg of the dried resin was treated with a mixture of 50% trifluoroacetic acid and 50% DCM for 1 hr at room temperature. After concentrated in vacuo, 16 mg (41 uMol, ~1.17 mMol/g resin) of white crystallized solid recovered.

Step 1D.

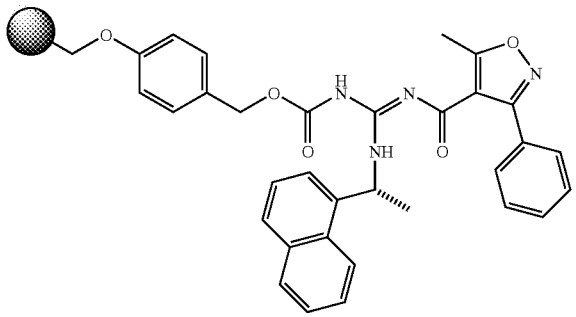

2.1 g of the resin prepared in Step 1C was filled into 60 Microkans (from IRORI company, 35 mg resin/Microkan, ~41 uMol/Microkan). One Microkan was placed in a reaction vial, to which 3 ml of anhydrous DCM, 40.88 mg (0.26 mMol) of 1-naphthalenemethylamine and 45 ul (0.26 mMol) of DIEA were added at room temperature. The reaction vial was shaken at room temperature for 2 days. The Microkan was pooled together with other 59 Microkans for other reactions, washed with DCM (3×200 ml), 1/1 DMF/MeOH (3×200 ml), THF(3×200 ml), and DCM (3×200 ml), dried in vacuo overnight.

Step 1E. The Microkan was treated with 1.5 ml of 50% TFA/50% DCM at room temperature for 1 hr., filtered and collected, concentrated in vacuo to afford the title compound.

EXAMPLE 2

N-((3,5-dichlorobenzylamino)(amino)methylene)-5-methyl-3-phenylisoxazole-4-carboxamide

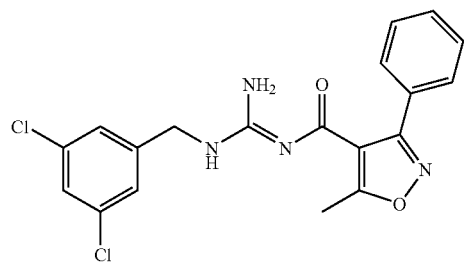

The title compound was prepared by analogy to Example 1. After purification by preparative HPLC, 9.5 mg (46%) of the title compound was obtained. MS(ESP+)m/e: 403.1(MH$^+$), HPLC (Phenomenex C18, 10 u 3.0×50 mm, 10% MeOH/90% H$_2$O/0.1% TFA to 90% MeOH/10% H$_2$O/0.1% TFA, gradient 2 min., flow rate=5 ml/min.), Rt: 2.1 min. $^1$H-NMR (CD$_3$OD, 500 MHz), δ 7.70 (d, 2H, J=9.5 Hz), 7.54-7.53(3H, m), 7.48(1H,s), 7.37(2H,s), 4.59(2H, s), 2.72(3H,s).

EXAMPLE 3

N-((3,5-dichlorobenzylanmino)(amino)methylene)-5-methyl-3-(4-fluorophenylisoxazole-4-carboxamide

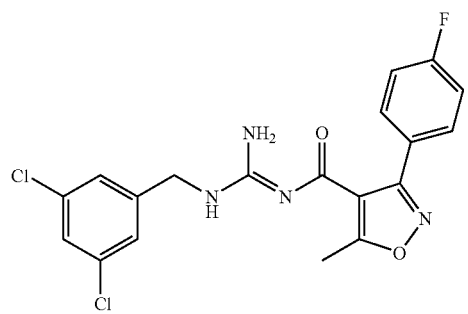

The title compound was prepared by analogy to Example 1. After purification by preparative HPLC, 4.6 mg (21%) of the title compound was obtained. MS(ESP+)m/e: 420.1 (MH$^+$), HPLC(Phenomenex C18, 10 u 3.0×50 mm, 10% MeOH/90% H$_2$O/0.1% TFA to 90% MeOH/10% H$_2$O/0.1% TFA, gradient 2 min., flow rate=5 ml/min.), Rt: 2.21 min. $^1$H-NMR (CD$_3$OD, 500 MHz), δ 7.75 (d, 2H, Br.), 7.48(1H, s), 7.38 (2H,s), 7.27(2H, Br), 4.60(2H, s), 2.72(3H,s).

EXAMPLE 4

N-((3,5-dichlorobenzylanmino)(amino)methylene)-5-methyl-3-(4-methoxyphenylisoxazole-4-carboxamide

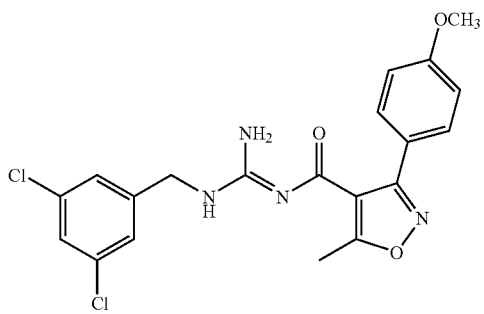

The title compound was prepared from 200 mg resin by analogy to Example 1. After purification by preparative HPLC, 28.5 mg (24%) of the title compound was obtained. MS(ESP+)ml/e: 433.13(MH$^+$)., HPLC(Phenomenex C18, 10 u 3.0×50 mm, 10% MeOH/90% H$_2$O/0.1% TFA to 90% MeOH/10% H$_2$O/0.1% TFA, gradient 2 min., flow rate=5 ml/min.), Rt: 2.24 min. $^1$H-NMR (CD$_3$OD, 500 MHZ) δ 7.64 (2H, d, J=8.5 Hz.), 7.48(1H, s), 7.38(2H,s), 7.07(2H, d, J=8.5 Hz.), 4.60(2H, s), 3.87 (3H,s), 2.70(3H,s).

EXAMPLE 5

N-(amino(naphthalene-1-ylmethylamino)methylene)-3-methyl-5-phenylisoxazole-4-carboxamide

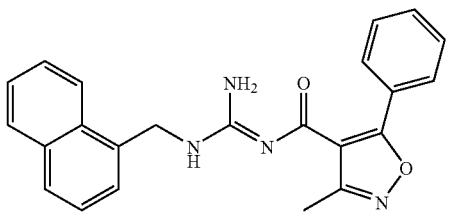

The title compound was prepared by analogy to Example 1. After purification by preparative HPLC, 11.1 mg (54%) of the title compound was obtained. MS(ESP+)m/e: 385.2(MH$^+$)., HPLC(Phenomenex C18, 10 u 3.0×50 mm, 10% MeOH/90% H$_2$O/0.1% TFA to 90% MeOH/10% H$_2$O/0.1% TFA, gradient 2 min., flow rate=5 ml/min.), Rt: 2.54 min. $^1$H-NMR (CD$_3$OD, 500 MHz) δ 8.03 (2H, d, J=8.5 Hz.), 7.99(2H, d, J=8.0 Hz), 7.96(2H,d, J=8.5 Hz), 7.83(4H, d, J=8.5 Hz.), 7.66(2H, t, J=7.0 Hz), 5.07(2H, s),2.47(3H,s).

EXAMPLE 6

N-(amino(3,5-dichlorobenzylamino)methylene)-3-methyl-5-(4-methoxyphenyl)isoxazole-4-carboxamide

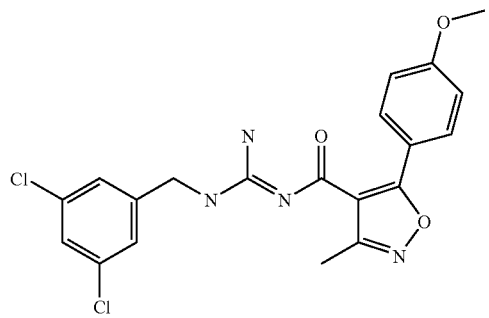

The title compound was prepared by analogy to Example 1. After purification by preparative HPLC, 15.7 mg (69%) of the title compound was obtained. MS(ESP+)m/e: 433.1(MH$^+$)., HPLC(Phenomenex C18, 10 u 3.0×50 mm, 10% MeOH/90% H$_2$O/0.1% TFA to 90% MeOH/10% H$_2$O/0.1% TFA, gradient 2 min., flow rate=5 ml/min.), Rt: 2.27 min. $^1$H-NMR (CD$_3$OD, 500 MHz) δ 7.81 (2H, d, J=8.5 Hz.), 7.49(1H, s), 7.39(2H,s), 7.13(2H, d, J=8.0 Hz.), 4.61(2H, s), 3.89(3H,s), 2.46(3H,s).

EXAMPLE 7

N-(amino(naphthalen-1-ylmethylamino)methylene)-5-methyl-3-(4-methoxyphenylisothiazole-4-carboxamide

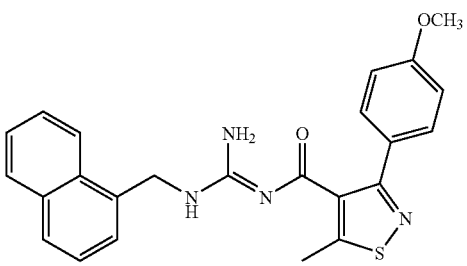

The title compound was prepared by analogy to Example 1. After purification by preparative HPLC, 14.0 mg (62%) of the title compound was obtained. MS(ESP+)m/e: 431.1 (MH$^+$)., HPLC(Waters-Sunfire, 4.6×50 mm, 10% MeOH/90% H$_2$O/ 0.1% TFA to 90% MeOH/10% H$_2$O/0.1% TFA, gradient 2 min., flow rate=4 ml/min.), Rt: 2.14 min. $^1$H-NMR(CD$_3$OD, 300 MHz) δ 7.99~7.93(3H, m), 7.65~7.48(6H, m), 7.01(2H, d, J=8.7 Hz), 5.05(2H, s), 3.86(3H,s), 2.74(3H,s).

EXAMPLE 8

N-((3,5-dichlorobenzylamino)(amino)methylene)-5-methyl-3-(4-methoxyphenyl)isothiazole-4-carboxamide

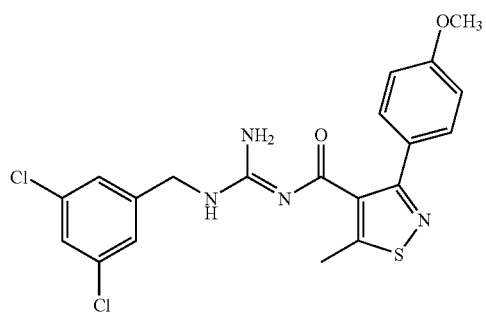

The title compound was prepared from 200 mg resin by analogy to Example 1. After purification by preparative HPLC, 28.5 mg (24%) of the title compound was obtained. MS(ESP+)m/e: 449.2(MH+)., HPLC(Waters-Sunfire, 4.6×50 mm, 10% MeOH/90% H$_2$O/0.1% TFA to 90% MeOH/10% H$_2$O/0.1% TFA, gradient 2 min., flow rate=5 ml/min.), Rt: 1.98 min. $^1$H-NMR(CD$_3$OD, 300 MHz) δ 7.61(2H, d, J=8.7 Hz.), 7.48(1H, s), 7.33(2H,s), 7.02(2H, d, J=8.7 Hz.), 4.59 (2H, s), 3.84 (3H,s), 2.73(3H,s).

EXAMPLE 9

N-(amino(naphthalen-2-ylmethylamino)methylene)-5-methyl-3-(4-methoxyphenyl)isothiazole-4-carboxamide

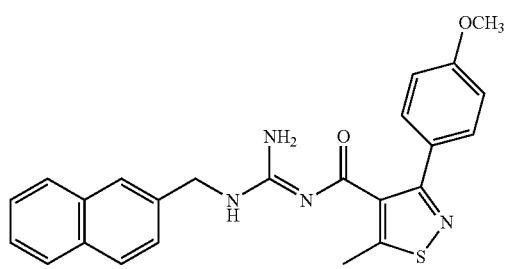

The title compound was prepared by analogy to Example 1. After purification by preparative HPLC, 3 mg (17%) of the title compound was obtained. MS(ESP+)m/e: 431.1 (MH+)., HPLC(Waters-Sunfire, 4.6×50 mm, 10% MeOH/90% H$_2$O/ 0.1% TFA to 90% MeOH/10% H$_2$O/0.1% TFA, gradient 2 min., flow rate=4 ml/min.), Rt: 2.13 min. $^1$H-NMR(CD$_3$OD, 300 MHz) δ 7.97~7.88(3H,m), 7.81(1H, s), 7.62(2H, d, J=8.7 Hz), 7.57~7.54(2H,m), 7.47(1H, m), 7.0(2H, d, J=8.7 Hz), 4.75(2H, s), 3.79(3H,s), 2.74(3H,s).

EXAMPLE 10

N-((3,5-dichlorobenzylamino)(amino)methylene)-3-methyl-5-(3-fluorophenylisothiazole-4-carboxamide

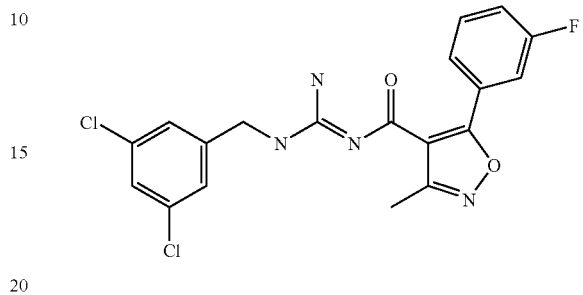

The title compound was prepared by analogy to Example 1. After purification by preparative HPLC, 19.8 mg (31%) of the title compound was obtained from 100 mg of the resin. MS(ESP+)m/e: 437.1(MH+)., HPLC(Waters-Sunfire, 4.6×50 mm, 10% MeOH/90% H$_2$O/0.1% TFA to 90% MeOH/10% H$_2$O/0.1% TFA, gradient 2 min., flow rate=4 ml/min.), Rt: 1.96 min. $^1$H-NMR(CD$_3$OD, 300 MHz) δ 7.48~7.46(4H, m), 7.32(2H, s), 7.23 (1H, m), 4.58(2H, s), 2.75(3H,s).

EXAMPLE 11

N-((3,5-dichlorobenzylamino)(amino)methylene)-5-methyl-3-(3-methoxyphenylisoxazole-4-carboxamide

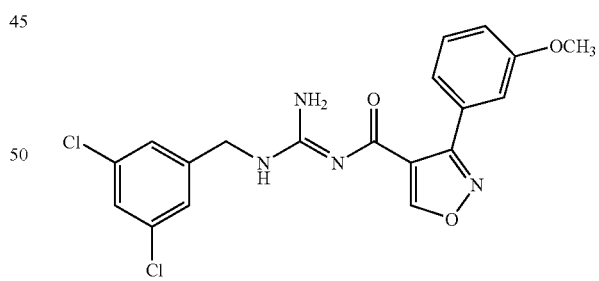

The title compound was prepared by analogy to Example 1. After purification by preparative HPLC, 19.8 mg (31%) of the title compound was obtained from 100 mg of the resin. MS(ESP+)m/e: 433.1(MH+)., HPLC(Phenomenex C18, 10 u 3.0×50 mm, 10% MeOH/90% H$_2$O/0.1% TFA to 90% MeOH/10% H$_2$O/0.1% TFA, gradient 2 min., flow rate=5 ml/min.), Rt: 2.13 min. $^1$H-NMR(CD$_3$OD, 500 MHz) δ 7.48 (1H, s), 7.44(1H, t, J=8.0 Hz), 7.37(2H, s), 7.24~7.22(2H,m), 7.11(1H, d,J=7.5 Hz), 4.59(2H, s), 3.85(3H,s), 2.71 (3H,s).

EXAMPLE 12

N-(amino(naphthalen-2-ylmethylamino)methylene)-
5-methylthiomethyl-3-phenylisoxazole-
4-carboxamide

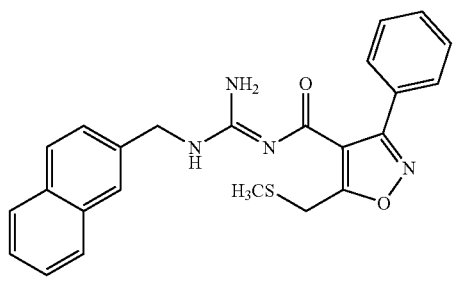

The title compound was prepared by analogy to Example 1. After purification by preparative HPLC, 4.5 mg (18%) of the title compound was obtained. MS(ESP+)m/e: 431.2(MH$^+$)., HPLC(Phenomenex C18, 10 u 3.0×50 mm, 10% MeOH/90% H$_2$O/0.1% TFA to 90% MeOH/10% H$_2$O/0.1% TFA, gradient 2 min., flow rate=5 ml/min.), Rt: 2.32 min. $^1$H-NMR (CD$_3$OD, 300 MHz) δ 8.01~7.94(3H, m), 7.71~7.53(9H, m), 5.06(2H, s), 4.1(2H,s), 2.22(3H,s).

EXAMPLE 13

N-((3,5-dichlorobenzylamino)(amino)methylene)-5-
methyl-3-(4-ethoxyphenyl)isoxazole-4-carboxamide

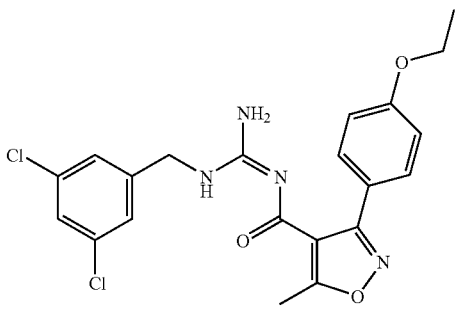

The title compound was prepared by analogy to Example 1. After purification by preparative HPLC, 6.0 mg (26%) of the title compound was obtained. MS(ESP+)m/e: 447.1 (MH$^+$)., HPLC(Phenomenex C18, 10 u 3.0×50 mm, 10% MeOH/90% H$_2$O/0.1% TFA to 90% MeOH/10% H$_2$O/0.1% TFA, gradient 2 min., flow rate=5 ml/min.), Rt: 2.41 min. $^1$H-NMR (CD$_3$OD, 300 MHz) δ 7.62(2H, d, J=8.5 Hz.), 7.49(1H, s), 7.48(2H,s), 7.05(2H, d, J=8.5 Hz.), 4.59(2H, s), 4.14(2H, q, J=6.9 Hz), 2.69(3H,s), 1.42(3H, t, J=7.2 Hz).

EXAMPLE 14

N-(amino(naphthalen-1-ylmethylamino)methylene)-
5-methyl-3-(4-ethoxyphenyl)isoxazole-
4-carboxamide

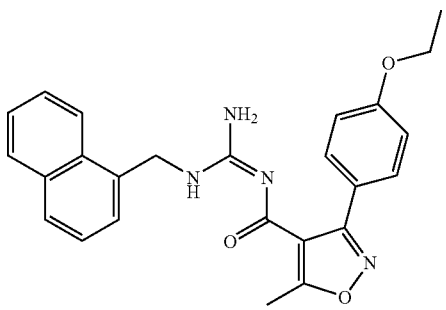

The title compound was prepared by analogy to Example 1. After purification by preparative HPLC, 9.3 mg (42%) of the title compound was obtained. MS(ESP+)m/e: 429.2(MH$^+$)., HPLC(Phenomenex C18, 10 u 3.0×50 mm, 10% MeOH/90% H$_2$O/0.1% TFA to 90% MeOH/10% H$_2$O/0.1% TFA, gradient 2 min., flow rate=5 ml/min.), Rt: 2.64 min. $^1$H-NMR (CD$_3$OD, 500 MHz) δ 8.02~7.94(3H, m), 7.67(1H, t, J=6.0 Hz), 7.65-7.62(5H,m), 7.01(2H, d, J=8.5 Hz), 5.04(2H, s), 4.1(2H,q, J=6.5 Hz), 2.67(3H,s), 1.42(3H, t, J=6.5 Hz).

EXAMPLE 15

N-((3,5-dichlorobenzylamino)(amino)methylene)-3-
methyl-5-(4-dimethylaminoxyphenylisoxazole-4-
carboxamide

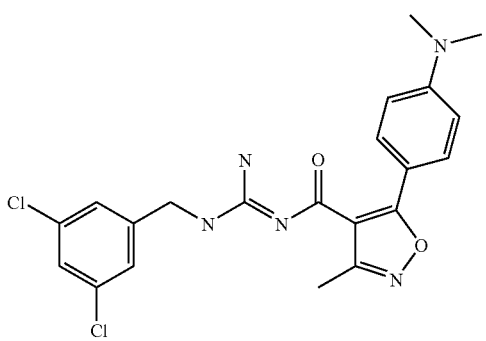

The title compound was prepared by analogy to Example 1. After purification by preparative HPLC, 2.3 mg (10%) of the title compound was obtained. MS(ESP+)m/e: 446.1(MH$^+$)., HPLC(Phenomenex C18, 10 u 3.0×50 mm, 10% MeOH/90% H$_2$O/0.1% TFA to 90% MeOH/10% H$_2$O/0.1% TFA, gradient 2 min., flow rate=5 ml/min.), Rt: 2.09 min. $^1$H-NMR (CD$_3$OD, 300 MHz) δ 7.70(2H, d, J=8.7 Hz), 7.49(1H, s), 7.39(2H,s), 6.86(2H, d, J=9.0 Hz), 4.61(2H, s), 3.07(6H, s), 2.43(3H,s).

EXAMPLE 16

N-(amino(naphthalen-1-ylmethylamino)methylene)-3-methyl-5-(4-dimethylaminophenyl)isoxazole-4-carboxamide

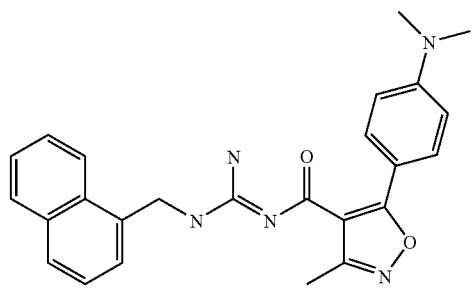

The title compound was prepared by analogy to Example 1. After purification by preparative HPLC, 1.1 mg (5%) of the title compound was obtained. MS(ESP+)m/e: 428.2(MH$^+$)., HPLC(Phenomenex C18, 10 u 3.0×50 mm, 10% MeOH/90% H$_2$O/0.1% TFA to 90% MeOH/10% H$_2$O/0.1% TFA, gradient 2 min., flow rate=5 ml/min.), Rt: 2.31 min. $^1$H-NMR (CD$_3$OD, 500 MHz) δ 8.02~7.90(3H, m), 7.67~7.51(6H, m), 6.80(2H, m), 5.06(2H, s), 3.04(6H, s), 2.42(3H,s).

EXAMPLE 17

N-((3,5-dichlorobenzylamino)(amino)methylene)-1,3-dimethyl-5-(4-methoxyphenyl)-1H-pyrazol-4-carboxamide

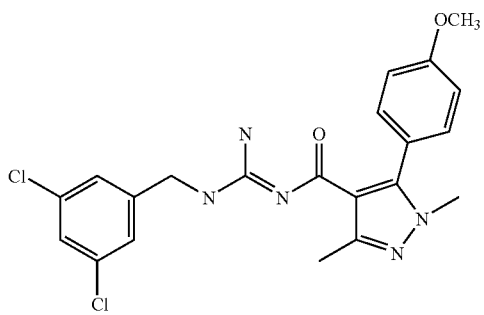

The title compound was prepared by analogy to Example 1. After purification by preparative HPLC, 2.0 mg (8.5%) of the title compound was obtained. MS(ESP+)m/e: 446.1(MH$^+$)., HPLC(Phenomenex C18, 10 u 3.0×50 mm, 10% MeOH/90% H$_2$O/0.1% TFA to 90% MeOH/10% H$_2$O/0.1% TFA, gradient 2 min., flow rate=5 ml/min.), Rt: 2.09 min. $^1$H-NMR (CD$_3$OD, 300 MHz) δ 7.48(3H, m), 7.30(2H, s), 7.11(2H, d, J=8.7 Hz), 4.5(2H, s), 3.87(3H, s), 3.71(3H, s), 2.46(3H,s).

EXAMPLE 18

N-((3,5-dichlorobenzylamino)(amino)methylene)-3-methyl-5-(4-methoxyphenyl)-1H-pyrazol-4-carboxamide

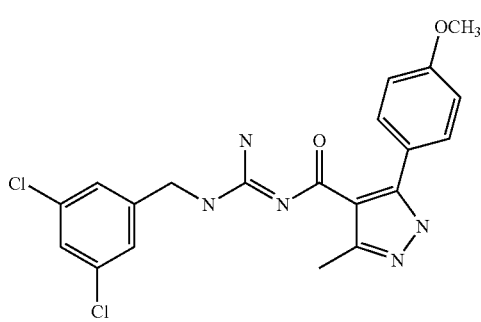

The title compound was prepared by analogy to Example 1. After purification by preparative HPLC, 3.8 mg (17%) of the title compound was obtained. MS(ESP+)m/e: 432.1(MH$^+$)., HPLC(Phenomenex C18, 10 u 3.0×50 mm, 10% MeOH/90% H$_2$O/0.1% TFA to 90% MeOH/10% H$_2$O/0.1% TFA, gradient 2 min., flow rate=5 ml/min.), Rt: 1.88 min. $^1$H-NMR (CD$_3$OD, 500 MHz) δ 7.56(2H, d, J=9 Hz), 7.48(1H, s), 7.35(2H, s), 7.06(2H, d, J=8.5 Hz), 4.57(2H, s), 3.85(3H, s), 2.51(3H, s).

EXAMPLE 19

N-((3,5-dichloro-4-hydroxybenzylamino)(amino)methylene)-5-methyl-3-(4-methoxyphenyl)isoxazole-4-carboxamide

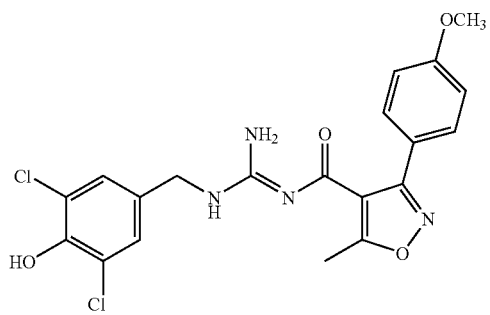

The title compound was prepared by analogy to Example 1. After purification by preparative HPLC, 7.9 mg (34%) of the title compound was obtained. MS(ESP+)m/e: 449.1 (MH$^+$)., HPLC(Phenomenex C18, 10 u 3.0×50 mm, 10% MeOH/90% H$_2$O/0.1% TFA to 90% MeOH/10% H$_2$O/0.1% TFA, gradient 2 min., flow rate=5 ml/min.), Rt: 1.86 min. $^1$H-NMR (CD$_3$OD, 500 MHz) δ 7.63(2H, d, J=8.5 Hz), 7.34(2H, s), 7.07(2H, d, J=9.0 Hz), 4.47(2H, s), 3.87(3H, s), 2.69(3H, s).

EXAMPLE 20

N-((3,5-dichlorobenzylamino)(amino)methylene)-3-(3,5-dimethoxyphenyl)-5-methylisoxazole-4-carboxamide

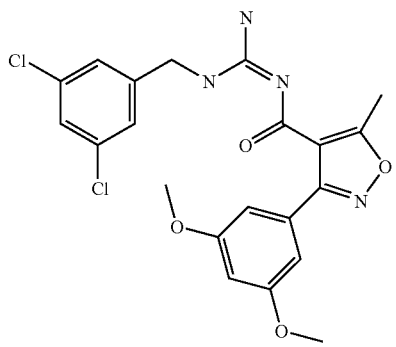

The title compound was prepared by analogy to Example 1. After purification by preparative HPLC, 3.1 mg (13%) of the title compound was obtained. MS(ESP+)m/e: 463.1 (MH+)., HPLC(Waters-Sunfire, 4.6×50 mm, 10% MeOH/90% H$_2$O/0.1% TFA to 90% MeOH/10% H$_2$O/0.1% TFA, gradient 2 min., flow rate=5 ml/min.), Rt: 1.97 min. $^1$H-NMR(CD$_3$OD, 300 MHz) δ 7.48(1H, s), 7.38(2H, s), 6.95(2H, s), 6.73(1H, s), 4.61(2H,s), 3.84(6H, s), 2.47(3H, s).

EXAMPLE 21

N-((3,5-dichlorobenzylamino)(amino)methylene)-3-methyl-5-(4-nitrophenyl)isoxazole-4-carboxamide

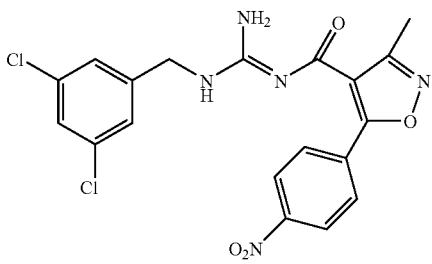

The title compound was prepared by analogy to Example 1. After purification by preparative HPLC, 3.4 mg (15%) of the title compound was obtained. MS(ESP+)m/e: 448.1(MH+)., HPLC(Phenomenex C18, 10 u 3.0×50 mm, 10% MeOH/90% H$_2$O/0.1% TFA to 90% MeOH/10% H$_2$O/0.1% TFA, gradient 2 min., flow rate=5 ml/min.), Rt: 2.24 min. $^1$H-NMR (CD$_3$OD, 500 MHz) δ 8.43(2H, d, J=8.0 Hz), 8.13(2H, d, J=8.5 Hz), 7.48(1H, s), 7.40(2H, s), 4.62(2H,s), 2.52(3H, s).

EXAMPLE 22

N-((3,5-dichloro-4-aminobenzylamino)(amino)methylene)-3-methyl-5-phenyl)isoxazole-4-carboxamide

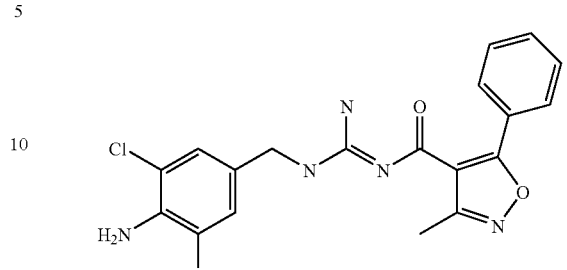

The title compound was prepared by analogy to Example 1. After purification by preparative HPLC, 14.2 mg (65%) of the title compound was obtained. MS(ESP+)m/e: 418.1(MH+)., HPLC(Phenomenex C18, 10 u 3.0×50 mm, 10% MeOH/90% H$_2$O/0.1% TFA to 90% MeOH/10% H$_2$O/0.1% TFA, gradient 2 min., flow rate=5 ml/min.), Rt: 1.97 min. $^1$H-NMR (CD$_3$OD, 500 MHz) δ 7.82(2H, d, J=8.0 Hz), 7.61~7.56(3H, m), 7.27(2H, s), 4.42(2H, s), 2.47(3H, s).

EXAMPLE 23

N-((3-chloro-5-hydroxybenzylamino)(amino)methylene)-5-methyl-3-(4-methoxyphenyl)isoxazole-4-carboxamide

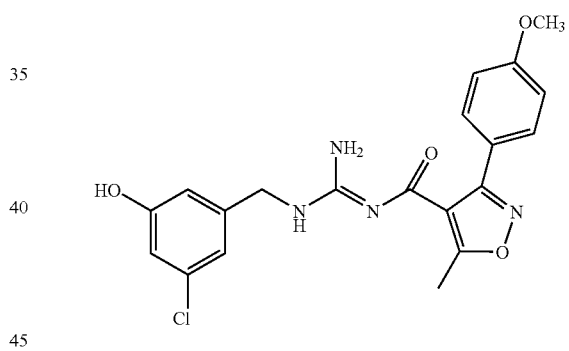

The title compound was prepared by analogy to Example 1. After purification by preparative HPLC, 7.1 mg (33%) of the title compound was obtained. MS(ESP+)m/e: 449.1(MH+)., HPLC(Phenomenex C18, 10 u 3.0×50 mm, 10% MeOH/90% H$_2$O/0.1% TFA to 90% MeOH/10% H$_2$O/0.1% TFA, gradient 2 min., flow rate=5 ml/min.), Rt: 1.85 min. $^1$H-NMR (CD$_3$OD, 300 MHz) δ 7.61(2H, d), 7.04(2H, d), 6.84(1H, s), 6.81(1H, s), 6.72(1H, s), 4.50(2H,s), 3.86(3H, s), 2.68(3H, s).

EXAMPLES 24 TO 147

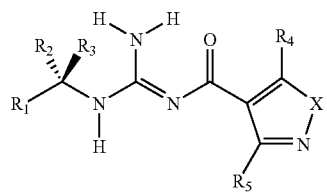

EXAMPLES 24 TO 147 WERE SYNTHESIZED BY ANALOGY TO EXAMPLE 1

| Ex. | R$_1$ | R$_2$ | R$_3$ | R$_4$ | R$_5$ | X | m/z | RT | LC/MS |
|---|---|---|---|---|---|---|---|---|---|
| 24 | 3-chloronaphthalen-1-yl | H | H | methyl | 4-methoxyphenyl | O | 449 | 2.63 | A |
| 25 | 3-chloronaphthalen-1-yl | H | H | methyl | 4-chlorophenyl | O | 453 | 2.81 | A |
| 26 | 3-chloronaphthalen-1-yl | H | H | methyl | 4-fluorophenyl | O | 437 | 2.68 | A |
| 27 | 2,3-dimethyl-1H-indol-5-yl | H | H | methyl | 4-methoxyphenyl | O | 432 | 2.15 | F |
| 28 | 3-isopropoxy-phenyl | H | H | methyl | 4-methoxyphenyl | O | 423 | 2.21 | F |
| 29 | 4-morpholinyl-methylphenyl | H | H | methyl | 4-methoxyphenyl | O | 464 | 1.64 | F |
| 30 | phenyl | H | H | methyl | 4-methoxyphenyl | O | 365 | 1.99 | H |
| 31 | 2-thienyl | H | H | methyl | 4-fluorophenyl | O | 359 | 1.89 | H |
| 32 | 1-naphthyl | CH$_3$ | H | methyl | 4-fluorophenyl | O | 417.2 | 1.52 | G |
| 33 | 3,4-dichlorophenyl | H | H | methyl | phenyl | O | 404 | 2.10 | J |
| 34 | 2,5-dichlorophenyl | H | H | methyl | phenyl | O | 404 | 1.90 | J |
| 35 | 2-naphthyl | CH$_3$ | H | methyl | phenyl | O | 400 | 2.00 | J |
| 36 | cyclohexyl | H | H | methyl | phenyl | O | 341.1 | 1.11 | G |
| 37 | 1-naphthyl | H | H | methyl | phenyl | O | 385.5 | 1.11 | G |
| 38 | 3-chloro-4-methylphenyl | H | H | methyl | phenyl | O | 383.1 | 1.13 | G |
| 39 | 3,4-dimethylphenyl | H | H | methyl | phenyl | O | 363.2 | 1.18 | G |
| 40 | 1-naphthyl | CH$_3$ | H | methyl | phenyl | O | 399.1 | 1.19 | G |
| 41 | 1-naphthyl | H | H | methyl | 4-fluorophenyl | O | 402.9 | 1.16 | G |
| 42 | 3,4-dichlorophenyl | H | H | methyl | 4-fluorophenyl | O | 420.8 | 1.16 | G |
| 43 | 3-chloro-4-methylphenyl | H | H | methyl | 4-fluorophenyl | O | 401.1 | 1.16 | G |
| 44 | 3,4-dimethylphenyl | H | H | methyl | 4-fluorophenyl | O | 381 | 1.14 | G |
| 45 | 1-naphthyl | CH$_3$ | H | methyl | 4-fluorophenyl | O | 417.1 | 1.21 | G |
| 46 | 2-naphthyl | H | CH$_3$ | methyl | 4-fluorophenyl | O | 417 | 1.22 | G |
| 47 | 1-naphthyl | H | H | methyl | 4-methoxyphenyl | O | 415.2 | 1.15 | G |
| 48 | 3,4-dichlorophenyl | H | H | methyl | 4-methoxyphenyl | O | 432.9 | 1.14 | G |
| 49 | 3-chloro-4-methylphenyl | H | H | methyl | 4-methoxyphenyl | O | 413.1 | 1.17 | G |
| 50 | 3,4-dimethylphenyl | H | H | methyl | 4-methoxyphenyl | O | 393.1 | 1.15 | G |
| 51 | 4-chloro-3-fluorophenyl | H | H | methyl | 4-methoxyphenyl | O | 417 | 1.1 | G |
| 52 | 2,5-dichlorophenyl | H | H | methyl | 4-methoxyphenyl | O | 433.1 | 1.15 | G |
| 53 | 2,3-dimethylphenyl | H | H | methyl | 4-methoxyphenyl | O | 393.2 | 1.15 | G |
| 54 | 3-fluoro-4-methylphenyl | H | H | methyl | 4-methoxyphenyl | O | 397.0 | 1.09 | G |
| 55 | 1-naphthyl | H | CH$_3$ | methyl | 4-methoxyphenyl | O | 429.2 | 1.18 | G |
| 56 | 1-naphthyl | CH$_3$ | H | methyl | 4-methoxyphenyl | O | 429.2 | 1.16 | G |
| 57 | 2-naphthyl | CH$_3$ | H | methyl | 4-methoxyphenyl | O | 429.1 | 1.16 | G |
| 58 | 2-naphthyl | H | CH$_3$ | methyl | 4-methoxyphenyl | O | 429 | 1.16 | G |
| 59 | cyclohexyl | H | H | methyl | 3,5-difluorophenyl | O | 377.2 | 1.22 | G |
| 60 | 1-naphthyl | H | H | methyl | 3,5-difluorophenyl | O | 421.1 | 1.18 | G |
| 61 | 3-chloro-4-methylphenyl | H | H | methyl | 3,5-difluorophenyl | O | 419.1 | 1.2 | G |
| 62 | 3-fluoro-4-methylphenyl | H | H | methyl | 3,5-difluorophenyl | O | 403.1 | 1.21 | G |
| 63 | 1-naphthyl | CH$_3$ | H | methyl | 3,5-difluorophenyl | O | 435 | 1.26 | G |
| 64 | 2-naphthyl | CH$_3$ | H | methyl | 3,5-difluorophenyl | O | 435.1 | 1.24 | G |
| 65 | 2-naphthyl | H | CH$_3$ | methyl | 3,5-difluorophenyl | O | 435.1 | 1.22 | G |
| 66 | 1-naphthyl | H | H | methyl | 3,5-dimethylphenyl | O | 413.2 | 2.03 | G |
| 67 | 1-naphthyl | H | H | methyl | 4-chlorophenyl | O | 418.1 | 1.91 | I |
| 68 | 1-naphthyl | H | H | methyl | 4-methylsulfonyl-phenyl | O | 463.1 | 1.76 | H |
| 69 | 1-naphthyl | H | H | methylthiomethyl | phenyl | O | 431.2 | 1.85 | I |
| 70 | 1-naphthyl | H | H | methoxmethyl | phenyl | O | 415.1 | 1.81 | I |
| 71 | 1-naphthyl | H | H | methyl | 3-fluorophenyl | O | 403.1 | 1.75 | I |
| 72 | 2-naphthyl | H | H | phenyl | methyl | O | 385.2 | 2.02 | I |
| 73 | 2-naphthyl | H | H | methyl | 3,5-dimethylphenyl | O | 413.1 | 2.16 | I |
| 74 | 3,5-dichlorophenyl | H | H | methyl | 4-chlorophenyl | O | 437.1 | 1.88 | I |
| 75 | 2-naphthyl | H | H | methyl | 4-chlorophenyl | O | 419.2 | 2.03 | I |
| 76 | quinolin-4-yl | H | H | methyl | 4-chlorophenyl | O | 420.1 | 1.85 | I |
| 77 | 3,5-dichlorophenyl | H | H | methyl | 4-methylsulfonyl-phenyl | O | 481.1 | 1.79 | I |
| 78 | 2-naphthyl | H | H | methyl | 4-methylsulfonyl-phenyl | O | 463.2 | 1.85 | I |
| 79 | 3,5-dichlorophenyl | H | H | methylthiomethyl | phenyl | O | 449.1 | 1.9 | I |
| 80 | 3,5-dichlorophenyl | H | H | methoxymethyl | phenyl | O | 433.1 | 1.85 | I |

-continued

| Ex. | R₁ | R₂ | R₃ | R₄ | R₅ | X | m/z | RT | LC/MS |
|---|---|---|---|---|---|---|---|---|---|
| 81 | 2-naphthyl | H | H | methoxymethyl | phenyl | O | 415.2 | 1.93 | I |
| 82 | 3,5-dichlorophenyl | H | H | ethyl | phenyl | O | 417.1 | 1.92 | I |
| 83 | 2-naphthyl | H | H | ethyl | phenyl | O | 399.2 | 2.15 | I |
| 84 | 3,5-dichlorophenyl | H | H | methyl | 3-fluorophenyl | O | 421.1 | 1.82 | I |
| 85 | 2-naphthyl | H | H | methyl | 3-fluorophenyl | O | 403.2 | 1.9 | I |
| 86 | 2-naphthyl | H | H | methyl | 4-methoxyphenyl | O | 415.1 | 1.95 | I |
| 87 | 3-hydroxyphenyl | H | H | methyl | 4-methoxyphenyl | O | 381.2 | 1.63 | H |
| 88 | 3-hydroxyphenyl | H | H | methyl | 4-fluorophenyl | O | 369.1 | 1.65 | H |
| 89 | 3-phenylphenyl | H | H | methyl | 4-fluorophenyl | O | 429.3 | 2.41 | I |
| 90 | 1-naphthyl | H | H | methyl | 4-methylphenyl | O | 399.1 | 2.05 | I |
| 91 | 3,5-dichlorophenyl | H | H | methyl | 4-methylphenyl | O | 417.1 | 1.85 | I |
| 92 | 2-naphthyl | H | H | methyl | 4-methylphenyl | O | 399.2 | 2.01 | I |
| 93 | 1-naphthyl | H | H | methyl | 3-chlorophenyl | O | 419.2 | 1.99 | I |
| 94 | 3,5-dichlorophenyl | H | H | methyl | 3-chlorophenyl | O | 437.1 | 1.83 | I |
| 95 | 1-naphthyl | H | H | methyl | 3-methylphenyl | O | 399.2 | 1.98 | I |
| 96 | 3,5-dichlorophenyl | H | H | methyl | 3-methylphenyl | O | 417.1 | 1.81 | I |
| 97 | 1-naphthyl | H | H | methyl | 3,4-dimethoxyphenyl | O | 445.2 | 2.1 | I |
| 98 | 3,5-dichlorophenyl | H | H | methyl | 3,4-dimethoxyphenyl | O | 463.1 | 1.94 | I |
| 99 | 1-naphthyl | H | H | 4-methoxyphenyl | methyl | O | 415.2 | 1.9 | I |
| 100 | 1-naphthyl | H | H | methyl | 3,4-difluorophenyl | O | 421.2 | 1.92 | I |
| 101 | 3,5-dichlorophenyl | H | H | methyl | 3,4-difluorophenyl | O | 439.9 | 1.85 | I |
| 102 | 1-naphthyl | H | H | H | 4-methoxyphenyl | O | 401.1 | 1.79 | I |
| 103 | 3,5-dichlorophenyl | H | H | H | 4-methoxyphenyl | O | 419 | 1.68 | I |
| 104 | 1-naphthyl | H | H | 4-chlorophenyl | methyl | O | 419.2 | 2.01 | I |
| 105 | 3,5-dichlorophenyl | H | H | 4-chlorophenyl | methyl | O | 437.3 | 1.87 | I |
| 106 | 1-naphthyl | H | H | 3-methoxyphenyl | methyl | O | 415.3 | 2.03 | I |
| 107 | 3,5-dichlorophenyl | H | H | 3-methoxyphenyl | methyl | O | 433.1 | 1.84 | I |
| 108 | 2-naphthyl | H | H | 3-methoxyphenyl | methyl | O | 415.2 | 2.04 | I |
| 109 | 1-naphthyl | H | H | 4-fluorophenyl | methyl | O | 403.1 | 1.96 | I |
| 110 | 3,5-dichlorophenyl | H | H | 4-fluorophenyl | methyl | O | 421.1 | 1.82 | I |
| 111 | 2-naphthyl | H | H | 4-fluorophenyl | methyl | O | 403.1 | 1.94 | I |
| 112 | 1-naphthyl | H | H | methyl | 4-bromophenyl | O | 463.1 | 2.46 | H |
| 113 | 3,5-dichlorophenyl | H | H | methyl | 4-bromophenyl | O | 481.9 | 2.24 | H |
| 114 | 2-naphthyl | H | H | methyl | 4-bromophenyl | O | 463.1 | 2.45 | H |
| 115 | 1-naphthyl | H | H | methyl | 3-methoxyphenyl | O | 415.1 | 2.24 | H |
| 116 | 2-naphthyl | H | H | methyl | 3-methoxyphenyl | O | 415.1 | 2.22 | H |
| 117 | 1-naphthyl | H | H | 3-fluorophenyl | methyl | O | 403.2 | 2.08 | H |
| 118 | 3,5-dichlorophenyl | H | H | 3-fluorophenyl | methyl | O | 421.1 | 1.97 | H |
| 119 | 2-naphthyl | H | H | 3-fluorophenyl | methyl | O | 403.2 | 1.92 | I |
| 120 | 1-naphthyl | H | H | methyl | 3-fluorophenyl | S | 419.1 | 2.19 | I |
| 121 | 2-naphthyl | H | H | methyl | 3-fluorophenyl | S | 419.1 | 2.17 | I |
| 122 | 2-naphthyl | H | H | methyl | 4-methoxyphenyl | O | 429.2 | 2.43 | H |
| 123 | 3-fluoro-5-trifluoromethylphenyl | H | H | methyl | 4-methoxyphenyl | O | 451.24 | 1.96 | K |
| 124 | 3,5-difluorophenyl | H | H | methyl | 4-methoxyphenyl | O | 415.25 | 1.87 | K |
| 125 | 3,4-dichlorobenzyl | H | H | methyl | 4-methoxyphenyl | O | 447.18 | 2.01 | K |
| 126 | 3-bromo-5-chlorophenyl | H | H | methyl | 4-methoxyphenyl | O | 477.1, 479.0 | 2.06 | H |
| 127 | 3-bromo-5-chlorophenyl | H | H | methyl | 4-methoxyphenyl | S | 492.9, 494.9 | 2.09 | H |
| 128 | 3-chloro-5-fluorophenyl | H | H | methyl | 4-methoxyphenyl | O | 417.02 | 1.96 | H |
| 129 | 3,5-dibromophenyl | H | H | methyl | 4-methoxyphenyl | O | 520.9, 522.9 | 2.09 | H |
| 130 | 3-trifluoromethylcyclohexyl | H | H | methyl | 4-methoxyphenyl | O | 439.23 | 2.04 | H |
| 131 | 3,5-dichlorophenyl | CH₂—OH | H | methyl | 4-methoxyphenyl | O | 463.14 | 2.04 | H |
| 132 | 4-amino-3,5-dichlorophenyl | H | H | methyl | 4-methoxyphenyl | NH | 447.09 | 1.72 | H |
| 133 | 4-amino-3-chloro | H | H | methyl | 4-methoxyphenyl | O | 414.19 | 1.75 | H |
| 134 | 3-chloro-5-(hydroxymethyl)phenyl | H | H | methyl | 4-methoxyphenyl | O | 429.2 | 1.81 | H |
| 135 | 3-chloro-5-(hydroxymethyl)phenyl | H | H | methyl | 4-methoxyphenyl | S | 445.18 | 1.84 | H |
| 136 | 3,5-dimethylphenyl | H | H | methyl | 4-methoxyphenyl | O | 393 | 2.48 | A |

-continued

| Ex. | R$_1$ | R$_2$ | R$_3$ | R$_4$ | R$_5$ | X | m/z | RT | LC/MS |
|---|---|---|---|---|---|---|---|---|---|
| 137 | 3,5-dimethylphenyl | H | H | methyl | 4-methoxyphenyl | S | 409 | 2.57 | A |
| 138 | 3-(aminomethyl)-5-chlorophenyl | H | H | methyl | 4-methoxyphenyl | O | 428 | 1.96 | A |
| 139 | 3,5-bis(trifluoromethyl)phenyl | H | H | methyl | 4-methoxyphenyl | O | 501 | 2.75 | A |
| 140 | 3,5-dimethylphenyl | H | H | methyl | 4-methoxyphenyl | NH | 392 | 2.42 | A |
| 141 | 3-amino-5-chlorophenyl | H | H | methyl | 4-methoxyphenyl | O | 414 | 2.15 | A |
| 142 | 4-amino-3-chloro-5-methylphenyl | H | H | methyl | 4-methoxyphenyl | S | 444 | 2.29 | A |
| 143 | 3,5-dichlorophenyl | H | H | phenyl | methyl | O | 403 | 2.79 | B |
| 144 | 4-acetamido-3-chloro-5-methylphenyl | H | H | methyl | 4-methoxyphenyl | S | 486 | 2.33 | B |
| 145 | 3-bromo-5-chlorophenyl | H | H | methyl | 4-methoxyphenyl | NH | 476.3 | 2.06 | H |
| 146 | 3,5-dichloro-4-propyloxy-phenyl | H | H | methyl | 4-methoxyphenyl | O | 491.1 | 2.21 | H |
| 147 | 3,5-dichloro-4-(3-methoxy-propoxy)phenyl | H | H | methyl | 4-methoxyphenyl | O | 521.1 | 2.26 | H |

EXAMPLE 148

N-((3-Bromo-4-amino-5-chlorobenzylamino)(amino)methylene)-3-(4-methoxyphenyl)-5-methyl-isoxazole-4-carboxamide

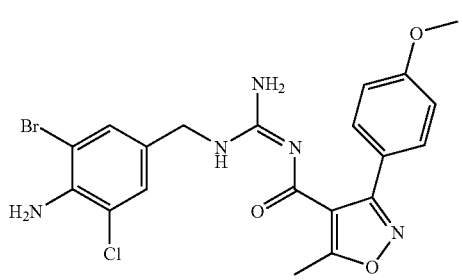

A mixture of tert-butyl-N-1-(3-(4-methoxyphenyl)-5-methylisoxazole-4-carbonyl)-2-methylisothiourea (150 mg, 0.37 mmol), 3-chloro-4-amino-5-bromobenzylamine (91 mg, 0.39 mmol) and DIPEA (65 mg, 0.5 mmol) in THF (3 mL) was stirred overnight. The solvent was removed and residue was treated with 20% TFA in DCM for 1 hour. The title compound was obtained (150 mg, 83%) by column with EtOAc/DCM (3/7) as the eluant. $^1$H NMR (CD$_3$OD): δ 2.68 (s, 3H), 3.87(s,3H), 4.41(s, 2H), 7.05, 7.07(d, 2H), 7.30(s, 1H), 7.42(s, 1H), 7.61, 7.63(d, 2H). MH$^+$=448.13, 450.13

EXAMPLE 149

N-((4-amino-3,5-dichlorobenzylamino)(amino)methylene)-3-(4-methoxyphenyl)-5-methylisothiazole-4-carboxamide

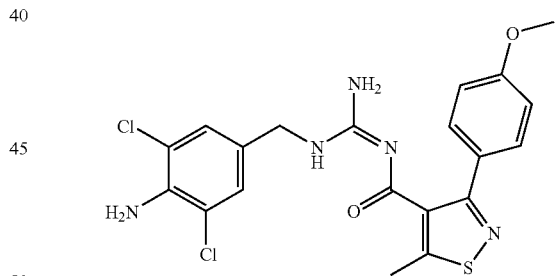

A mixture of Tert-butyl-N-1-(3-(4-methoxyphenyl)-5-methylisothiazole-4-carbonyl)-2-methylisothiourea (90 mg, 0.28 mmol), 3,5-dichloro-4-aminobenzylamine (57 mg, 0.30 mmol) and DIPEA (65 mg, 0.5 mmol) in THF (3 mL) was stirred overnight. The solvent was removed and residue was treated with 20% TFA in DCM for 1 hour. The title compound was obtained (84 mg, 43%) by HPLC purification. $^1$H NMR (CD$_3$OD): δ 2.73 (s, 3H), 3.85 (s, 3H), 4.42(s, 2H), 7.01, 7.03(d, 2H), 7.24 (s, 2H), 7.60, 7.62(d, 2H). MH$^+$=464.09, 466.09.

EXAMPLE 150

N-((3-Bromo-4-amino-5-chlorobenzylamino)(amino)methylene)-3-(4-methoxyphenyl)-5-methylisothiazole-4-carboxamide

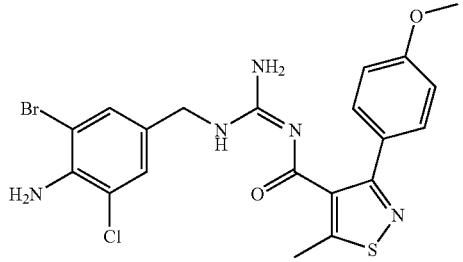

The title compound was prepared by analogy to Example 149. $^1$H NMR (CD$_3$OD): δ 2.73 (s, 3H), 3.85 (s, 3H), 4.42(s, 2H), 7.01, 7.03(d, 2H), 7.28 (s, H), 7.40(s,1H), 7.60, 7.62(d, 2H). MH$^+$=508.08, 510.07.

EXAMPLE 151

N-((3-chloro-4-amino-5-iodobenzylamino)(amino)methylene)-3-(4-methoxyphenyl)-5-methylisothiazole-4-carboxamide

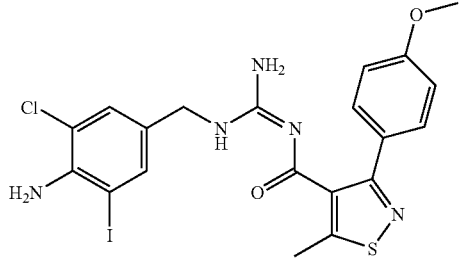

The title compound was prepared by analogy to Example 149. $^1$H NMR (CD$_3$OD): δ 2.73 (s, 3H), 3.85 (s, 3H), 4.39(s, 2H), 7.01, 7.03(d, 2H), 7.04 (s, H), 7.30(s,1H), 7.60, 7.62(d, 2H). MH$^+$=556.05

EXAMPLE 152

N-((3-chloro-5-((E)-3-methoxyprop-1-enyl)benzylamino)(amino)methylene)-3-(4-methoxyphenyl)-5-methylisoxazole-4-carboxamide

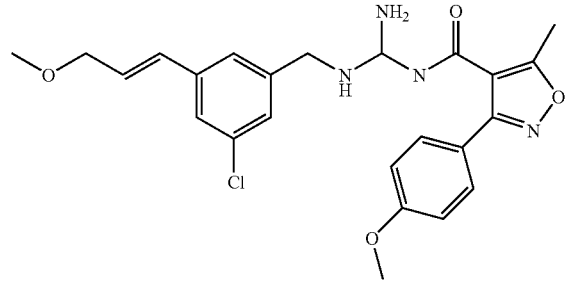

A mixture of N-((3-Bromo-5-chlorobenzylamino)(amino)methylene)-3-(4-methoxyphenyl)-5-methylisoxazole-4-carboxamide TFA salt (~10-15 mg) (Prepared by analogy to Example 1), (E)-2-(3-methoxypropenyl)-4,4,5,5,-tetramethyl-(1,3,2)-dioxaborolane (20 mg), tetrakis-(triphenylphosphine)-palladium (5 mg) and aqueous tripotassium phosphate (2M, 100 μl) in DMF (1 mL) was heated at 85° C. under nitrogen overnight. Product was obtained by HPLC purification. $^1$H NMR (CD$_3$OD): δ 2.69 (s, 3H), 3.40 (s, 3H), 3.86(s, 3H), 4.11, 4.13(d, 2H), 4.58(s, 2H), 6.44(m, 1H), 6.64, 6.67(d, 1H), 7.05, 7.07(d, 2H), 7.29 (s, 1H), 7.37(s,1 H), 7.46 (s, 1H), 7.62, 7.64(d, 2H). MH$^+$=469.23

EXAMPLE 153

N-((4-amino-3-chloro-5-((E)-3-methoxyprop-1-enyl)benzylamino)(amino)methylene)-3-(4-methoxyphenyl)-5-methylisoxazole-4-carboxamide

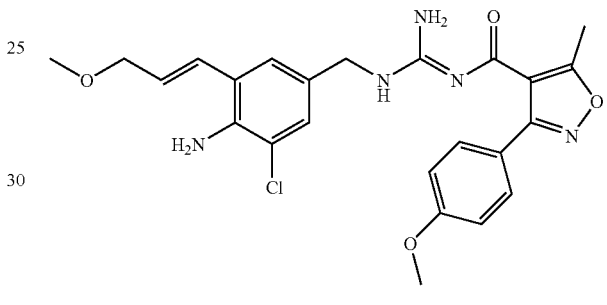

The title compound was prepared by analogy to Example 152. $^1$H NMR (CD$_3$OD): δ 2.68 (s, 3H), 3.42 (s, 3H), 3.86(s, 3H), 4.11, 4.13(d, 2H), 4.42(s, 2H), 6.23(m, 1H), 6.78, 6.81 (d, 1H), 7.04, 7.06(d, 2H), 7.23 (s, 1H), 7.28(s,1 H), 7.60, 7.62(d, 2H). MH$^+$=484.25

EXAMPLE 154

N-((4-amino-3-chloro-5-((E)-3-methoxyprop-1-enyl)benzylamino) (amino)methylene)-3-(4-methoxyphenyl)-5-methylisothiazole-4-carboxamide

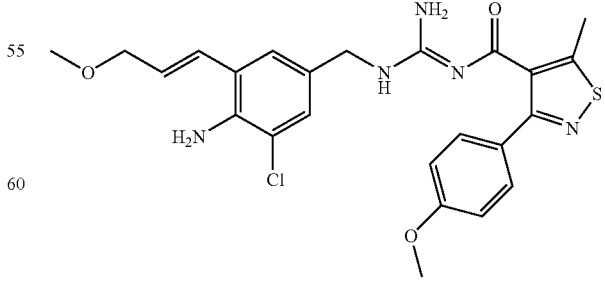

The title compound was prepared by analogy to Example 152. $^1$H NMR (CD$_3$OD): δ2.71 (s, 3H), 3.42 (s, 3H), 3.84(s, 3H), 4.11, 4.13(d, 2H), 4.41(s, 2H), 6.23(m, 1H), 6.79, 6.82 (d, 1H), 6.98, 7.00(d, 2H), 7.21 (s, 1H), 7.27(s, 1H), 7.59, 7.61(d, 2H). MH$^+$=500.16

EXAMPLES 155 TO 171

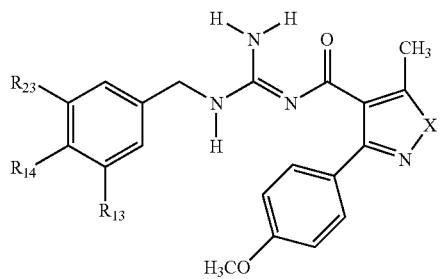

EXAMPLES 155 TO 171 WERE SYNTHESIZED BY ANALOGY TO EXAMPLE 152.

| Ex. | $R_{13}$ | $R_{14}$ | $R_{23}$ | X | MW | m/z | RT | Method |
|---|---|---|---|---|---|---|---|---|
| 155 | Cl | H | 4-chlorophenyl | O | 509.4 | 509, 511 | 2.25 | H |
| 156 | Cl | H | 3-chloro-4-fluorophenyl | O | 527.4 | 527, 529 | 2.26 | H |
| 157 | Cl | H | 3,4-dichlorophenyl | O | 543.8 | 543 | 2.32 | H |
| 158 | Cl | H | 3,5-difluorophenyl | O | 510.9 | 511 | 2.19 | H |
| 159 | Cl | H | allyl | O | 438.9 | 439 | 2.09 | H |
| 160 | Cl | H | 3-pyridyl | O | 475.9 | 476 | 1.72 | H |
| 161 | Cl | H | (E)-styryl | O | 501.0 | 501 | 2.52 | H |
| 162 | Cl | H | (Z)-propenyl | O | 438.9 | 439 | 2.11 | H |
| 163 | Cl | H | (E)-hex-1-enyl | O | 481.0 | 481 | 2.32 | H |
| 164 | Cl | H | (E)-pent-1-enyl | O | 467.0 | 467 | 2.19 | H |
| 165 | Cl | H | vinyl | O | 424.9 | 425 | 2.01 | H |
| 166 | Cl | H | (E)-3,3-dimethylbut-1-enyl | O | 481.0 | 481 | 2.27 | H |
| 167 | Cl | H | 3-thienyl | O | 481.0 | 481 | 2.02 | H |
| 168 | Cl | H | (E)-4-hydroxybut-1-enyl | O | 468.9 | 469 | 2.04 | H |
| 169 | Cl | H | (E)-prop-1-enyl | O | 438.9 | 439 | 2.14 | H |
| 170 | H | H | (E)-3-methoxyprop-1-enyl | O | 434.5 | 435 | 1.97 | H |
| 171 | Cl | NH2 | allyl | O | 453.9 | 454 | 2.19 | H |

EXAMPLE 172

N-((3-chloro-5-(3-methoxypropoxy)benzylamino)(amino)methylene)-3-(4-methoxyphenyl)-5-methyl-isoxazole-4-carboxamide)

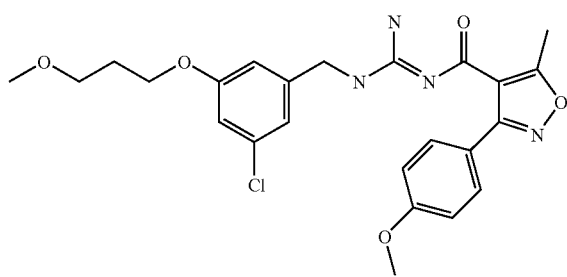

The title compound was prepared on solid support as outlined in Scheme 11.

Step 172A.

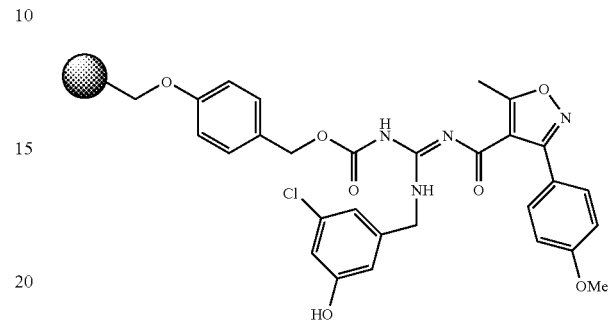

3-chloro-5-hydroxybenzyl resin was prepared by analogy to Example 1, steps 1A -1D.

Step 172B. To a reaction vial was placed a Microkan containing 35 mg of the resin prepared in Step 172A, 3 ml of anhydrous THF, 37 ul of 3-methoxy-1propanol, 41 mg of triphenylphosphine, and 49 ul of DEAD at room temperature. The reaction vial was shaken at room temperature overnight. Drained and washed with THF (3×), DMF(3×), 1/1 DMF/MeOH (3×), THF(2×), DCM(2×), and dried in vacuo overnight, then treated with 50% TFA/DCM at room temperature for 1 hr to afford 10.5 mg (43%) of the product after purification by preparative HPLC. MS(ESP+)m/e: 487.1(MH$^+$), HPLC(Waters-Sunfire, 4.6×50 mm S5), 10% MeOH/90% H$_2$O/0.1% TFA to 90% MeOH/10% H$_2$O/0.1% TFA, gradient 2 min., flow rate=4 ml/min.), Rt: 2.11 min. $^1$H-NMR (CD$_3$OD, 500 MHz) δ 7.61 (2H, d), 7.07(2H, d), 6.98~6.87 (3H, m), 4.55(2H,s), 4.21~4.13(2H, m), 3.86(3H, s), 3.59 (2H, m), 3.52(3H,s), 2.69(3H, s), 1.43(2H, m).

EXAMPLE 173

N-((3-chloro-5-propoxybenzylamino)(amino)methylene)-5-methyl-3-(4-methoxyphenyl)isoxazole-4-carboxamide

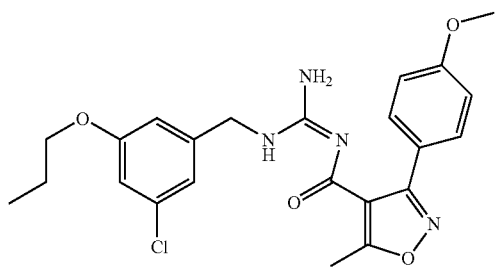

The title compound was prepared by analogy to Example 172. 7.5 mg (32%) of the product was obtained after purification by preparative HPLC. MS(ESP+)m/e: 457.1(MH+), HPLC(Waters-Sunfire, 4.6×50 mm S5), 10% MeOH/90% H$_2$O/0.1% TFA to 90% MeOH/10% H$_2$O/0.1% TFA, gradient 2 min., flow rate=4 ml/min.), Rt: 2.14 min. $^1$H-NMR (CD$_3$OD, 500 MHz) δ 7.61(2H, d), 7.07(2H, d), 6.98(2H, s), 6.88 (1H,s), 4.54(2H,s), 4.06~3.96(2H, m), 3.87(3H, s), 2.69 (3H, s), 1.84-1.79(2H,m), 1.05(3H, t).

EXAMPLE 174

N-((3-chloro-5-butoxybenzylamino)(amino)methylene)-5-methyl-3-(4-methoxyphenyl)isoxazole-4-carboxamide

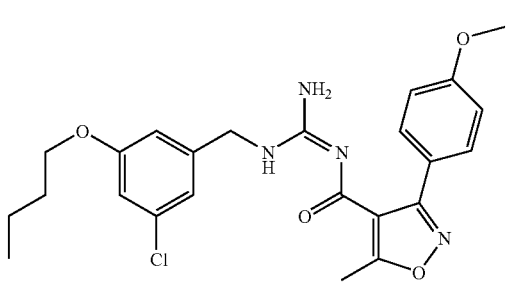

The title compound was prepared by analogy to Example 172. 4.1 mg (18%) of the product was obtained after purification by preparative HPLC. MS(ESP+)m/e: 471.1 (MH+), HPLC(Waters-Sunfire, 4.6×50 mm S5), 10% MeOH/90% H$_2$O/0.1% TFA to 90% MeOH/10% H$_2$O/0.1% TFA, gradient 2 min., flow rate=4 ml/min.), Rt: 2.26 min. $^1$H-NMR (CD$_3$OD, 500 MHz) δ 7.62(2H, d), 7.07(2H, d), 6.96(2H, s), 6.88 (1H,s), 4.54(2H,s), 4.02(2H, t), 3.87(3H, s), 2.69(3H, s), 1.81-1.75(2H,m), 1.56~1.49(2H,m), 1.01(3H, t).

EXAMPLES 175 TO 189

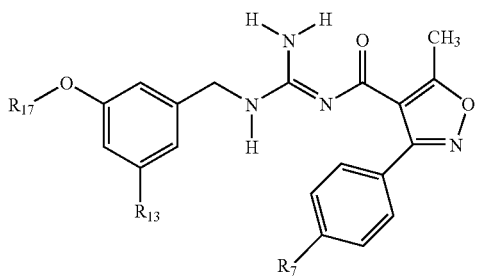

EXAMPLES 175 TO 189 WERE SYNTHESIZED BY ANALOGY TO EXAMPLE 172.

| Ex | R$_{17}$ | R$_{13}$ | R$_7$ | MW | m/z | RT | LC/MS |
|---|---|---|---|---|---|---|---|
| 175 | methyl | chloro | methoxy | 428.9 | 429 | 2.46 | A |
| 176 | 3-(methylamino)propyl | chloro | methoxy | 486.0 | 486 | 2.06 | A |
| 177 | 4-chlorobutyl | chloro | methoxy | 505.4 | 505 | 2.82 | A |
| 178 | 2-furylmethyl | chloro | methoxy | 494.9 | 495 | 2.02 | I |
| 179 | 3-benzyloxypropyl | chloro | methoxy | 563.1 | 563 | 2.41 | I |
| 180 | 3-chloropropyl | H | methoxy | 456.9 | 457 | 2.15 | I |
| 181 | 3-methoxypropyl | H | methoxy | 452.5 | 453 | 2.12 | I |
| 182 | 3-benzyloxypropyl | H | methoxy | 528.6 | 429 | 2.34 | I |
| 183 | propyl | H | methoxy | 422.5 | 423 | 2.09 | I |
| 184 | butyl | H | methoxy | 436.5 | 437 | 2.16 | I |
| 185 | 3-chloropropyl | chloro | fluoro | 479.3 | 479 | 2.24 | I |
| 186 | 3-methoxypropyl | chloro | fluoro | 474.9 | 475 | 2.17 | I |
| 187 | propyl | chloro | fluoro | 444.9 | 445 | 2.14 | I |
| 188 | butyl | chloro | fluoro | 458.9 | 459 | 2.22 | I |
| 189 | 3-chloropropyl | H | fluoro | 444.9 | 445 | 2.11 | I |

EXAMPLE 190

(E)-N-((3-chloro-5-(2-chloroethoxy)benzylamino)(amino)methylene)-3-(4-methoxyphenyl)-5-methyl-isoxazole-4-carboxamide

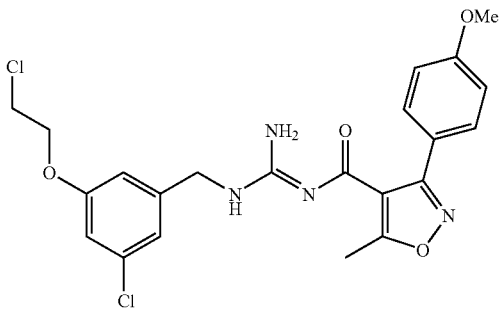

The compound of Example 23 (8.3 mg, 0.020 mmol), 1-bromo-2-chloroethane (14 mg, 0.1 mmol), cesium carbonate (13 mg, 0.04 mmol) and potassium iodide (4 mg, 0.024 mmol) were mixed in 1 mL of THF in an 8-mL glass vial. The vial was capped and shaken at RT overnight. The reaction mixture was filtered through Acrodisc Syringe Filter (0.45 μm). Solvent was evaporated in vacuo. The residue was purified by preparative HPLC to give 2.2 mg of the title compound. LC/MS (method A) RT 2.61, MH$^{30}$ 477. $^1$H NMR (500 MHz, CD$_3$OD) δ 7.60 (d, J=8.2 Hz, 2 H), 7.05 (d, J=8.2 Hz, 2 H), 6.99 (s, 2 H), 6.90 (s, 1 H), 4.53 (s, 2 H), 4.26 (t, J=5.3 Hz, 2 H), 3.86 (t, J=5.3 Hz, 2 H), 3.84 (s, 3 H), 2.66 (s, 3 H).

EXAMPLE 191

Preparation of (E)-ethyl 3-chloro-5-((2-(3-(4-methoxyphenyl)-5-methylisoxazole-4-carbonyl)guanidino)methyl)phenylcarbamate

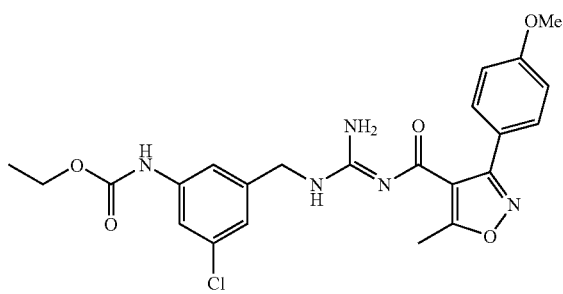

Step 191A.

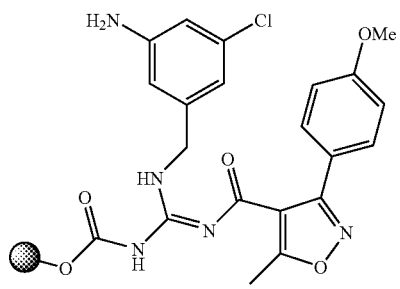

To 35 MicroKans containing the resin-bound methylisothiourea (40 mg in each MicroKan, 1.4 mmol in total) (prepared by analogy to Example 1, Steps 1A-1C) in a 160-mL glass jar was added a solution of 0.987 g (6.3 mmol) of 3-amino-5-chlorobenzylamine and 1.63 g (12.6 mmol) of DIEA in 60 mL of NMP. The jar was sealed with a cap and shaken at room temperature for 2 days. The liquid portion of the reaction mixture was removed and the MicroKans were washed with DMF (3×80 mL), THF (3×80 mL), and DCM (4×80 mL). The resin in MicroKans was dried in vacuo overnight.

Step 191B.

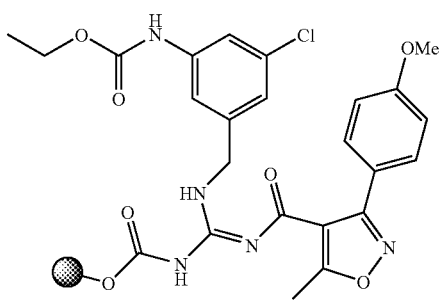

One MicroKan containing resin-bound aniline (0.040 mmol) from Step 191A was placed in an 8-mL glass vial. DCM (2 mL) and DIEA (0.21 mL, 1.2 mmol) were added, followed by the addition of ethyl chloroformate (43 mg, 0.40 mmol). The vial was capped and shaken at room temperature overnight. The MicroKan was washed with DCM (3×3 mL), DCM/MeOH (9:1) (2×3 mL), and DCM (3×3 mL). The MicroKan was dried in vacuo overnight.

Step 191C. The resin in the MicroKan from Step 191B was treated with 1.5 mL of TFA/DCM (30:70) at room temperature for 1.5 hrs. DCM and TFA were evaporated in vacuo to give a crude product after the MicroKan was removed. The product was purified by preparative HPLC to give 3.9 mg of the title compound. LC/MS (method C) RT 2.26 min., MH$^{30}$ 486. $^1$H NMR (500 MHz, CD$_3$OD) δ 7.61 (d, J=8.5 Hz, 2 H), 7.51 (s, 1 H), 7.39 (s, 1 H), 7.04 (d, J=8.5 Hz, 2 H), 7.02 (s, 1 H), 4.54 (s, 2 H), 4.18 (q, J=7.0 Hz, 2 H), 3.83 (s, 3 H), 2.67 (s, 3 H), 1.29 (t, J=7.0 Hz, 3 H).

EXAMPLES 192 TO 202

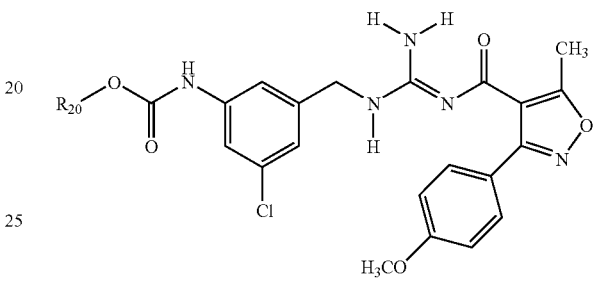

EXAMPLES 192 TO 202 WERE SYNTHESIZED BY ANALOGY TO EXAMPLE 191.

| Example | R$_{20}$ | MW | m/z | RT | LC/MS |
|---|---|---|---|---|---|
| 192 | methyl | 471.9 | 472 | 2.42 | E |
| 193 | isobutyl | 514.0 | 514 | 3 | E |
| 194 | propyl | 500.0 | 500 | 2.84 | E |
| 195 | butyl | 514.0 | 514 | 2.96 | E |
| 196 | 4-nitrobenzyl | 593.0 | 593 | 2.9 | E |
| 197 | 4-fluorophenyl | 552.0 | 552 | 2.91 | E |
| 198 | 2-methoxyethyl | 516.0 | 516 | 2.41 | E |
| 199 | 4-chlorobutyl | 548.4 | 548 | 2.93 | E |
| 200 | 2-propynyl | 495.9 | 496 | 2.57 | E |
| 201 | 1,1-dioxobenzothien-2-ylmethyl | 636.1 | 636 | 2.74 | E |
| 202 | 3-chloropropyl | 534.4 | 534 | 2.79 | E |

EXAMPLE 203

Ethyl 3-chloro-5-((2-(3-(4-methoxyphenyl)-5-methylisoxazole-4-carbonyl)guanidino)methyl)benzylcarbamate)

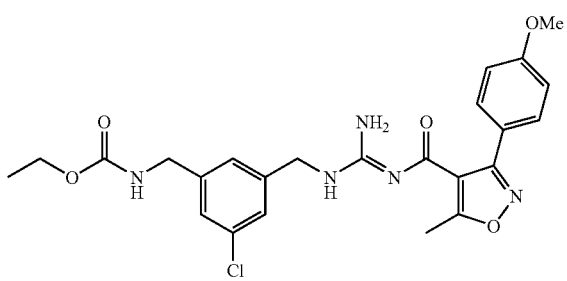

93

Step 203A.

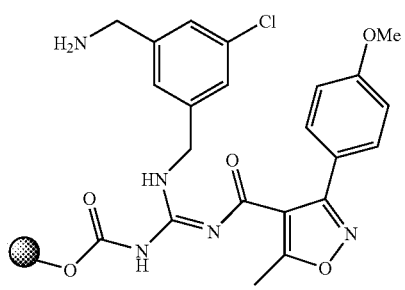

To the suspension of the resin-bound methylisothiourea (3.0 g, 3.5 mmol) (prepared by analogy to Example 1, Steps 1A-1C) in DCM (90 mL) in a 500-mL round bottom flask was added a solution of 5.97 g (35.0 mmol) of 3(aminomethyl)-5-chlorobenzylamine and 4.52 g (35.0 mmol) of DIEA in 10 mL of NMP. The flask, capped with a rubber septum, was shaken at room temperature for 2 days. The resin was washed with DCM (3×100 mL), DMF/MeOH (1:1) (3×100 mL), THF (3×100 mL), and DCM (3×100 mL). The resin was dried in vacuo overnight.

Step 203B.

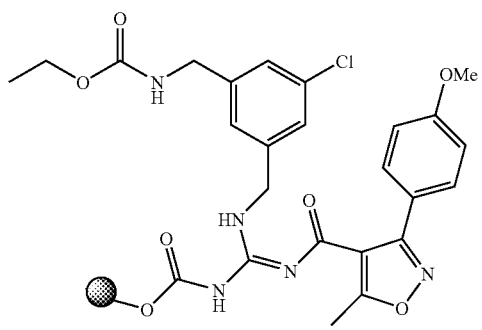

A MicroKan containing 30 mg of resin-bound benzylamine (0.030 mmol) from step 203A was placed in an 8-mL glass vial. DCM (2 mL) and DIEA (0.16 mL, 0.90 mmol) were added, followed by the addition of ethyl chloroformate (33 mg, 0.30 mmol). The vial was capped and shaken at room temperature overnight. The MicroKan was washed with DCM (3×3 mL), DCM/MeOH (9:1) (2×3 mL), and DCM (3×3 mL). The MicroKan was dried in vacuo overnight.

Step 203C. The resin in the MicroKan from step 203B was treated with 1.5 mL of TFA/DCM (30:70) at room temperature for 1.5 hrs. DCM and TFA were evaporated in vacuo to give a crude product after the MicroKan was removed. The product was purified by preparative HPLC to give 4.3 mg of the title compound. LC/MS (method C) RT 2.22 min., MH[30] 500. $^1$H NMR (500 MHz, CD$_3$OD) δ 7.61 (d, J=8.4 Hz, 2 H), 7.29 (s, 1 H), 7.27 (s, 1 H), 7.21 (s, 1 H), 7.04 (d, J=8.4 Hz, 2 H), 4.55 (s, 2 H), 4.26 (s 2 H), 4.07 (q, J=7.0 Hz, 2 H), 3.84 (s, 3 H), 2.67 (s, 3 H), 1.22 (t, J=7.0 Hz, 3 H).

94

EXAMPLES 204 TO 212

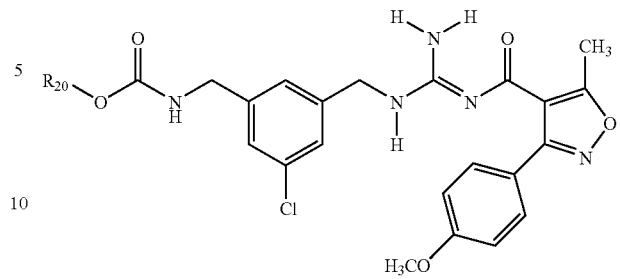

EXAMPLES 204 TO 212 WERE SYNTHESIZED BY ANALOGY TO EXAMPLE 203.

| Example | R$_{20}$ | MW | m/z | RT | LC/MS |
|---|---|---|---|---|---|
| 204 | 2-chloroethyl | 534.4 | 534 | 2.25 | C |
| 205 | propyl | 514.0 | 514 | 2.71 | E |
| 206 | butyl | 528.0 | 528 | 2.88 | E |
| 207 | 4-nitrobenzyl | 607.0 | 607 | 2.82 | E |
| 208 | 4-fluorophenyl | 566.0 | 566 | 2.85 | E |
| 209 | isopropyl | 514.0 | 514 | 2.70 | E |
| 210 | 4-chlorobutyl | 562.5 | 562 | 2.83 | E |
| 211 | 3-chloropropyl | 548.4 | 548 | 2.74 | E |
| 212 | 2-benzyloxyethyl | 606.1 | 607 | 2.89 | E |

EXAMPLE 213

N-((3-butyramido-5-chlorobenzylamino)(amino)methylene)-3-(4-methoxyphenyl)-5-methylisoxazole-4-carboxamide

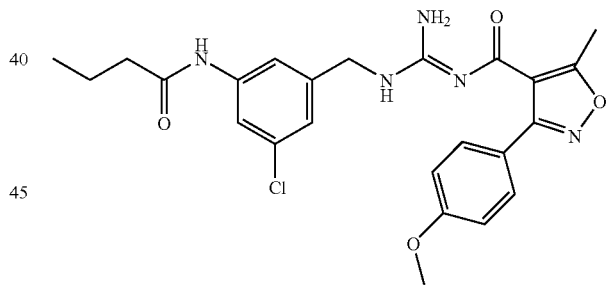

Step 213A.

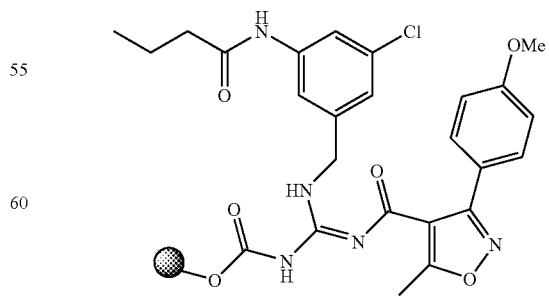

One MicroKan containing resin-bound aniline (0.040 mmol) was placed in an 8-mL glass vial. DCM (2 mL) and DIEA (0.14 mL, 0.8 mmol) were added, followed by the addition of butyryl chloride (43 mg, 0.40 mmol). The vial was capped and shaken at room temperature overnight. The MicroKan was washed with DCM (3×3 mL), DCM/MeOH (9:1) (2×3 mL), and DCM (3×3 mL). The MicroKan was dried in vacuo overnight.

Step 213B. The product was cleaved from the resin and purified as described in the carbamate synthesis to give 6.2 mg of the title compound. LC/MS (method A) RT 2.50 min., MH$^{30}$ 484. $^1$H NMR (500 MHz, CD$_3$OD) δ 7.68 (s, 1 H), 7.61 (d, J=8.5 Hz, 2 H), 7.50 (s, 1 H), 7.09 (s, 1 H), 7.04 (d, J=8.5 Hz, 2 H), 4.55 (s, 2 H), 3.83 (s, 3 H), 2.67 (s, 3 H), 2.35 (t, J=7.5 Hz, 2 H), 1.71 (m, 2 H), 0.98 (t, J=7.3 Hz, 3 H).

EXAMPLE 214

N-(((E)-3-chloro-5-(cinnamamidomethyl)benzylamino)(amino)methylene)-3-(4-methoxyphenyl)-5-methylisoxazole-4-carboxamide

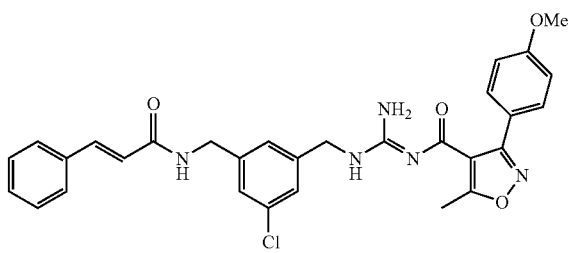

Step 214A.

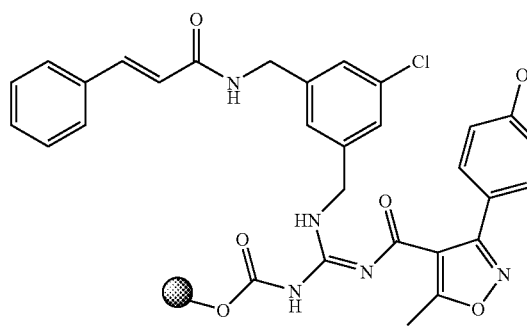

A MicroKan containing 30 mg of resin-bound benzylamine (0.030 mmol) was placed in an 8-mL glass vial. To this vial was added trans-cinnamic acid (44.4 mg, 0.30 mmol), EDCI (58 mg, 0.30 mmol), HOBt (48 mg, 0.312 mmol), DCM (2 mL) and DIEA (0.105 mL, 0.60 mmol). The vial was capped and shaken at room temperature overnight. The MicroKan was washed with DCM (3×3 mL), DCM/MeOH (9:1) (2×3 mL), and DCM (3×3 mL). The MicroKan was dried in vacuo overnight.

Step 214B. The product was cleaved off the resin and purified as described for the carbamate to give 4.8 mg of the title compound. LC/MS (method B) RT 2.80 min., MH$^{30}$ 558. $^1$H NMR (500 MHz, CD$_3$OD) δ 7.62-7.50 (m, 5 H), 7.39-7.35 (m, 3 H), 7.34 (s, 1 H), 7.29 (s, 1 H), 7.26 (s, 1 H), 7.03 (d, J=8.5 Hz, 2 H), 6.64 (d, J=15.9 Hz, 1 H), 4.56 (s, 2 H), 4.49 (s, 2 H), 3.82 (s, 3 H), 2.62 (s, 3 H).

EXAMPLES 215 TO 236

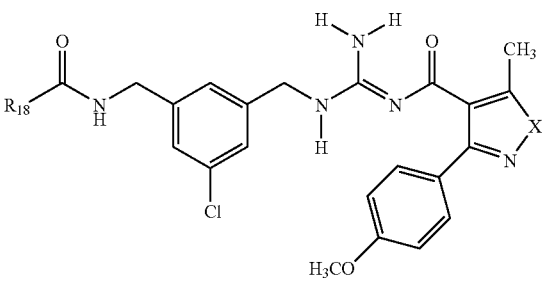

EXAMPLES 215 TO 236 WERE SYNTHESIZED BY ANALOGY TO EXAMPLE 214.

| Example | R$_{18}$ | X | MW | m/z | RT | LC/MS |
|---|---|---|---|---|---|---|
| 215 | methyl | O | 469.9 | 470 | 2.25 | A |
| 216 | propyl | O | 498.0 | 498 | 2.39 | A |
| 217 | cyanomethyl | O | 494.9 | 495 | 2.01 | D |
| 218 | ethyl | O | 484.0 | 484 | 2.02 | D |
| 219 | N,N dimethylaminomethyl | O | 513.0 | 513 | 1.93 | D |
| 220 | 4-methoxybenzyl | O | 576.1 | 576 | 2.31 | D |
| 221 | butyl | O | 512.0 | 512 | 2.31 | D |
| 222 | pentyl | O | 526.0 | 526 | 2.47 | D |
| 223 | 2-thienylmethyl | O | 552.1 | 552 | 2.30 | D |
| 224 | 3-thienylmethyl | O | 552.1 | 552 | 2.29 | D |
| 225 | 1H-imidazol-4-ylmethyl | O | 536.0 | 536 | 1.71 | D |
| 226 | 2-pyridinylmethyl | O | 547.0 | 547 | 1.99 | D |
| 227 | cyclopropylmethyl | O | 510.0 | 510 | 2.16 | D |
| 228 | 2-methoxyethyl | O | 514.0 | 514 | 1.95 | D |
| 229 | 2,2,2-trifluoroethyl | O | 537.9 | 538 | 2.24 | D |
| 230 | 2-(azepan-1-yl)ethyl | O | 581.1 | 581 | 1.92 | D |
| 231 | 2-morpholinoethyl | O | 569.1 | 569 | 1.83 | D |
| 232 | phenethyl | O | 560.1 | 560 | 2.78 | B |
| 233 | styryl | O | 558.0 | 558 | 2.80 | B |
| 234 | 2-phenylcyclopropyl | O | 572.1 | 572 | 2.85 | B |
| 235 | 2-benzothienyl | O | 588.1 | 588 | 2.86 | B |
| 236 | 2-benzofuryl | O | 572.0 | 572 | 2.86 | B |

EXAMPLE 237

N-(((E)-3-chloro-5-(cinnamamidomethyl)benzylamino)(amino)methylene)-3-(4-methoxyphenyl)-5-methylisothiazole-4-carboxamide

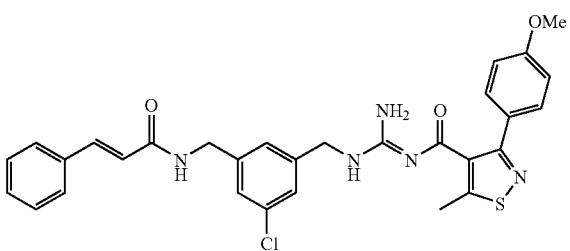

Step 237A:

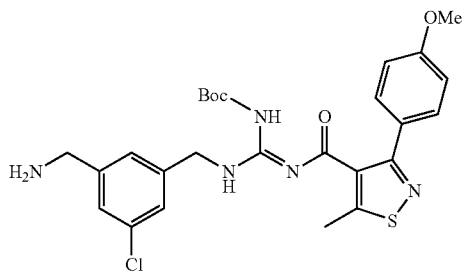

A solution of 0.300 g (0.712 mmol) of tert-butyl N-(3-(4-methoxyphenyl)-5-methylisothiazole-4-carbonyl)(methylthio)carbonoimidoylcarbamate (as prepared in Step 152B) in DCM (20 mL) was added dropwise to the solution of 3-(aminomethyl)-5-chlorobenzylamine (0.65 g, 3.81 mmol) and DIEA (1.5 mL, 8.61 mmol) in DCM (20 mL) with stirring. The resulting reaction mixture was stirred at room temperature overnight. Water (50 mL) was added to the reaction mixture and layers were separated. The aqueous layer was extracted with DCM and the combined DCM solution was washed with water. DCM was evaporated in vacuo to give a crude product, which was used without purification. LC/MS (method B) RT 3.02 min., MH$^{30}$ 544.

Step 237B. The crude benzyl amine intermediate (30 mg), EDCI (21 mg, 0.11 mmol), HOBt (17 mg, 0.11 mmol), and DIEA (28 mg, 0.22 mmol) were mixed in 1.5 mL of DCM in an 8-mL glass vial. The reaction mixture in the capped vial was shaken at room temperature overnight. Solvent was evaporated in vacuo to give a crude product, which was purified by preparative HPLC. LC/MS (method B) RT 3.52 min., MH$^{30}$ 674. The Boc-protecting group was removed by treating with TFA/DCM (55/45) at RT for 30 min. Purification by preparative HPLC yielded 9.1 mg of the title compound. LC/MS (method B) RT 2.89 min., MH$^+$574. $^1$H NMR (500 MHz, CD$_3$OD) δ 7.62-7.50 (m, 5 H), 7.41-7.33 (m, 4 H), 7.27 (s, 1 H), 7.25 (s, 1 H), 7.00 (d, J=8.5 Hz, 2 H), 6.64 (d, J=15.9 Hz, 1 H), 4.56 (s, 2 H), 4.50 (s, 2 H), 3.81 (s, 3 H), 2.68 (s, 3 H).

EXAMPLE 238

N-((3-chloro-5-(propylsulfonamidomethyl)benzylamino)(amino)methylene)-3-(4-methoxyphenyl)-5-methylisoxazole-4-carboxamide

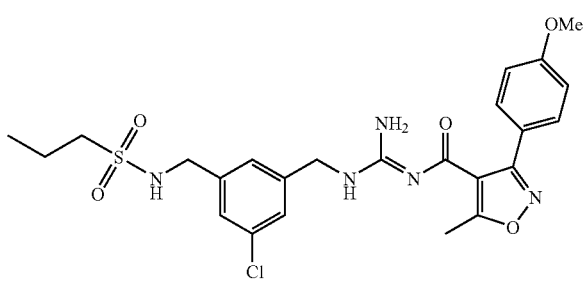

Step 238A.

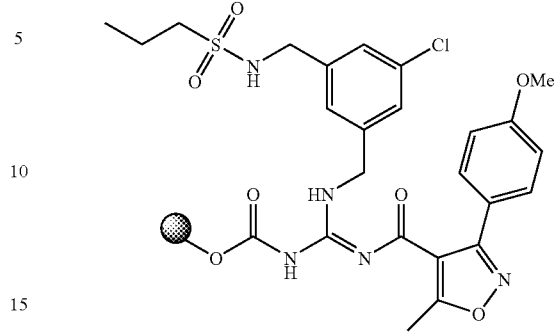

A MicroKan containing 30 mg of resin-bound benzylamine (0.030 mmol) was placed in an 8-mL glass vial. DCM (2 mL) and NMM (0.1 mL, 0.90 mmol) were added, followed by the addition of 1-propanesulfonyl chloride (43 mg, 0.30 mmol). The vial was capped and shaken at room temperature for 2 days. The MicroKan was washed with DCM (3×3 mL), DCM/MeOH (9:1) (2×3 mL), and DCM (3×3 mL). The MicroKan was dried in vacuo overnight.

Step 238B. The product was cleaved off the resin and purified by preparative HPLC to give 1.8 mg of the title compound. LC/MS (method A) RT 2.38 min., MH$^{30}$ 534. $^1$H NMR (500 MHz, CD$_3$OD) δ 7.61 (d, J=8.4 Hz, 2 H), 7.38 (s, 1 H), 7.34 (s, 1 H), 7.31 (s, 1 H), 7.05 (d, J=8.4 Hz, 2 H), 4.58 (s, 2 H), 4.24 (s 2 H), 3.84 (s, 3 H), 2.98 (t, J=7.8 Hz, 2 H), 2.67 (s, 3 H), 1.78 (m, 2 H), 1.02 (t, J=7.3, 3 H).

EXAMPLES 239 TO 247

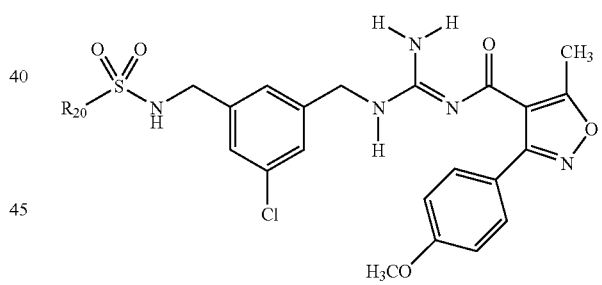

EXAMPLES 239 TO 247 WERE SYNTHESIZED BY ANALOGY TO EXAMPLE 238.

| Example | R$_{20}$ | MW | m/z | RT | LC/MS |
|---|---|---|---|---|---|
| 239 | 2-thienyl | 574.1 | 574 | 2.31 | D |
| 240 | phenyl | 568.1 | 568 | 2.52 | A |
| 241 | 3-nitrophenyl | 613.1 | 613 | 2.46 | D |
| 242 | 4-acetamidophenyl | 625.1 | 625 | 2.14 | D |
| 243 | 3-chloro-4-fluorophenyl | 620.5 | 620 | 2.36 | D |
| 244 | 3,5-dichlorophenyl | 636.9 | 636 | 2.73 | D |
| 245 | 3,4-dimethoxyphenyl | 628.1 | 628 | 2.54 | A |
| 246 | 4-acetylphenyl | 610.1 | 610 | 2.47 | A |
| 247 | 1,2-dimethyl-1H-imidazol-4-yl | 586.1 | 586 | 1.97 | D |

EXAMPLE 248

3-chloro-5-((2-(3-(4-methoxyphenyl)-5-methylisoxazole-4-carbonyl)guanidino)methyl)benzyl(tetrahydrofuran-2-yl)methylcarbamate

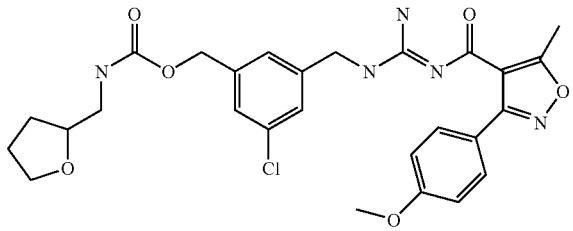

Step 248A. Solid phase linked —N-(3-(4-methoxypheny)-5-methylisoxazole-4-carbonyl)(methylthio)carbonoimidoylcarbamate (resin, 1 mmol/g, 30 mg of resin in a single Microkan, 0.03 mmol) in NMP (2 mL) was treated with 3-chloro-5-(hydroxymethyl)benzylamine (30 mg, 0.14 mmol) and DIPEA (30 mg, 0.20 mmol) overnight. Resin was washed with DMF (2×), MeOH/DCM (1:1, 2×), DCM (2×), then dried in vacuum.

Step 248B. The resin prepared in Step 248A (1 Microkan, 0.03 mmol) was treated with 4-nitrophenyl chloroformate (282 mg, 1.4 mmol) and DIPEA (258 mg, 2 mmol) in THF (2 mL) overnight. Resin in Microkans was washed with MeOH/DCM (1:1, 1×), DCM (1×).

Step 248C. The resin prepared in Step 248A (1 Microkan, 0.03 mmol) was treated with tetrahydrofuran-2-ylmethylamine (0.5 mmol) in DMF (2 mL) and shaken overnight. The resin was washed with DMF (2×), MeOH/DCM (1:1, 2×), DCM (2×), then cleaved with 20% TFA in DCM for 1.5 hours. The crude product was purified by HPLC to afford the title compound. $^1$H NMR (CD$_3$OD): δ 1.60 (s, 1H), 1.90 (m, 2H), 1.98 (m, 1H), 2.70 (s, 3H), 3.21(m, 2H), 3.73(m, 1H), 3.87(m, 4H), 3.96 (m, 1H), 4.59(s, 2H), 5.11(s, 2H), 7.07, 7.08(d, 2H), 7.30 (s, 1H), 7.36(s,1H), 7.42 (s, 1H),7.64, 7.65(d, 2H). MH$^+$=556.24, RT=1.98 Min.

EXAMPLE 249

3-chloro-5-((2-(3-(4-methoxyphenyl)-5-methylisoxazole-4-carbonyl)guanidino)methyl)benzyl 2-hydroxyethylcarbamate

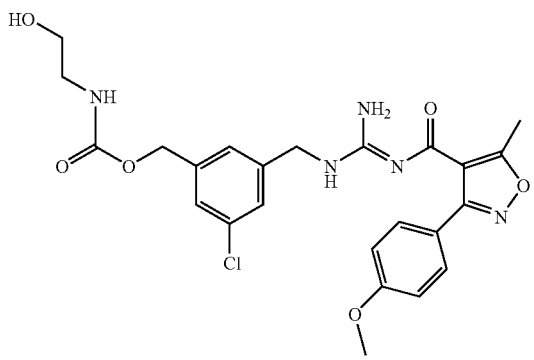

The title compound was prepared by analogy to Example 248. $^1$H NMR (CD$_3$OD): δ 2.70 (s, 3H), 3.24(t, 2H), 3.59(t, 2H), 3.87(s, 3H), 4.59(s, 2H), 5.11(s, 2H), 7.07, 7.09(d, 2H), 7.31 (s, 1H), 7.36(s,1H), 7.43 (s, 1H),7.64, 7.66(d, 2H). MH$^+$=516.20, RT=1.87 Min.

EXAMPLE 250

Benzyl 2-((3-chloro-5-((2-(3-(4-methoxyphenyl)-5-methylisoxazole-4-carbonyl)guanidino)methyl)benzyloxy)carbonyl)acetate

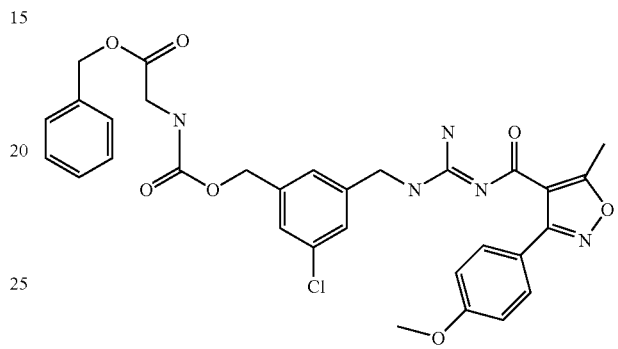

The title compound was prepared by analogy to Example 248. $^1$H NMR (CD$_3$OD): δ 2.69 (s, 3H), 3.86(s, 3H), 3.93(s, 2H), 4.59(s, 2H), 5.15(s, 2H), 5.18 (s, 2H), 7.06, 7.08(d, 2H), 7.32-7.39 (m, 7H), 7.43 (s, 1H),7.63, 7.65(d, 2H). MH$^+$=620.19, RT=2.10 Min.

EXAMPLE 251

N-((3-chloro-5-(hydroxymethyl)benzylamino)(amino)methylene)-3-(4-methoxyphenyl)-5-methylisothiazole-4carboxamide

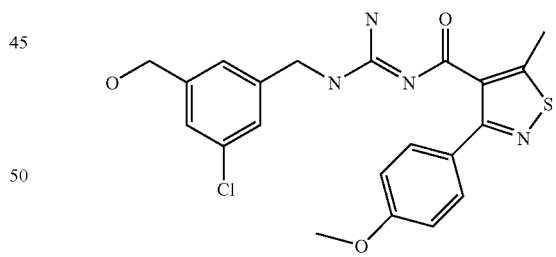

Step 251A. A mixture of tert-butyl N-(3-(4-methoxypheny)-5-methylisoxazole-4-carbonyl)(methylthio)carbonoimidoylcarbamate (100 mg, 0.24 mmol), 3-chloro-5-(hydroxymethyl)benzylamine (41 mg, 0.24 mmol) and DIPEA (39 mg, 0.3 mmol) was stirred in THF (5 mL) overnight.

Step 251B. The mixture was treated with 20% TFA/DCM (1 mL) for 1.5 hour. The title was obtained as an white solid after HPLC purification. $^1$H NMR (CD$_3$OD): δ 2.74 (s, 3H), 3.85(s, 3H), 4.60(s, 2H), 4.65(s, 2H), 7.02, 7.04(d, 2H), 7.28 (s, 2H), 7.39(s,1 H), 7.61, 7.63(d, 2H). MH$^+$=445.19, RT=1.83 Min.

EXAMPLE 252

3-chloro-5-((2-(3-(4-methoxyphenyl)-5-methyl-isothiazole-4-carbonyl)guanidino)methyl)benzyl 2-methoxyethylcarbamate

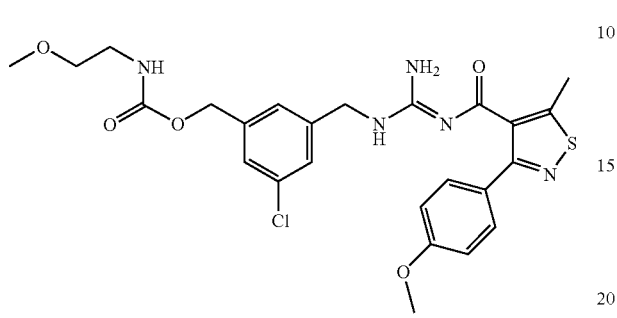

Step 252A. N-((3-chloro-5-(hydroxymethyl)benzylamino)(amino)methylene)-3-(4-methoxyphenyl)-5-methyl-isothiazole-4carboxamide (Example 251) (20 mg) was treated with 4-nitrophenyl chloroformate (45 mg) and N-methyl morpholine (100 mg) in $CH_2Cl_2$ overnight, then 2-methoxyethanamine (30 mg) was added and stirring continued for 1.5 hours. The title compound was obtained as a white solid after HPLC purification.

$^1$H NMR ($CD_3OD$): δ 2.74 (s, 3H), 3.30(t, 2H), 3.45(t, 3H), 3.35 (s, 3H), 3.85(s, 3H), 4.59(s, 2H), 5.11(s, 2H), 7.02, 7.04(d, 2H), 7.28 (s, 2H), 7.33(s, 1H), 7.42(s, 1H), 7.61, 7.63(d, 2H). $MH^+$=546.24, RT=1.96 Min.

EXAMPLE 253

3-chloro-5-((2-(3-(4-methoxyphenyl)-5-methyl-isothiazole-4-carbonyl)guanidino)methyl)benzyl 2-phenoxyethylcarbamate

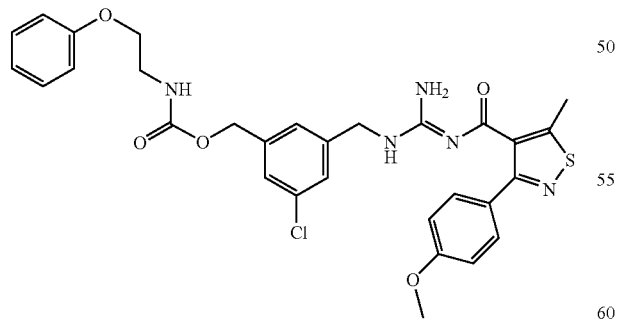

The title compound was prepared by analogy to Example 252. $^1$H NMR ($CD_3OD$): δ 2.74 (s, 3H), 3.51(t, 2H), 3.84(s, 3H), 4.03(t, 2H), 4.57(s, 2H), 5.13(s, 2H), 6.91, 6.93(m, 3H), 7.01, 7.03 (d, 2H), 7.26 (t, 3H), 7.32(s,1H), 7.42(s, 1H), 7.60, 7.62(d, 2H). $MH^+$=608.24, RT=2.15 Min.

EXAMPLE 254

N-((4-amino-3-chlorobenzylamino)(amino)methylene)-3-(4-methoxyphenyl)-5-methylisoxazole-4-carboxamide

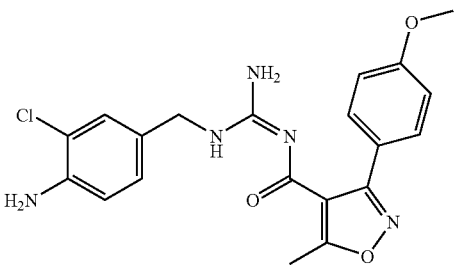

The title compound was prepared by analogy to Example 1. $^1$H NMR ($CD_3OD$): δ 2.68 (s, 3H), 3.87(s, 3H), 4.41(s, 2H), 6.89, 6.91(d, 1H), 7.05, 7.07 (d, 2H), 7.08,7.10 (d, 1H), 7.28 (s,1H), 7.60, 7.62(d, 2H). $MH^+$=414.19, RT=1.75 Min.

EXAMPLE 255

N-((3-chloro-4-(2-(2-methoxyethoxy)acetamido)benzylamino)(amino)methylene)-3-(4-methoxyphenyl)-5-methylisoxazole-4-carboxamide

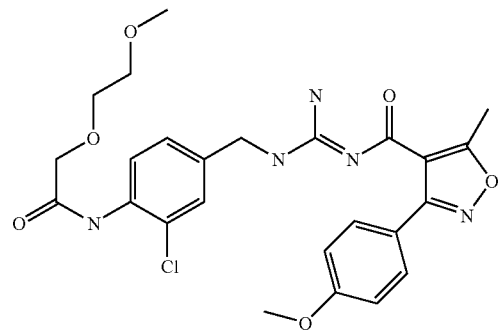

Step 255A.

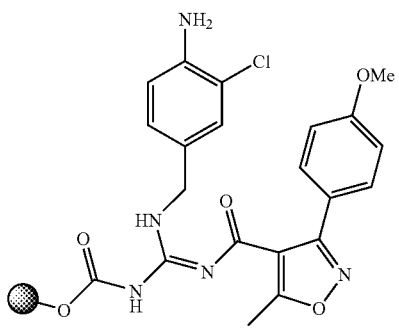

Solid phase linked N-(3-(4-methoxypheny)-5-methylisoxazole-4-carbonyl)(methylthio)carbonoimidoylcarbamate resin was prepared by analogy to Step 191A.

Step 255B. One Microkan containing 30 mg (0.03 mmol) of the resin prepared in Step 255A was treated with methoxyethoxyacetyl chloride (76 mg, 0.5 mmol) and DIPEA (129 mg, 1 mmol) in DCM overnight. Resin in Microkans was washed with DMF (2×), MeOH/DCM (1:1, 2×), DCM (2×), then treated with 20% TFA/DCM (1 mL) for 1.5 hours. Product was purified by HPLC to afford the title compound. $^1$H NMR (CD$_3$OD): δ 2.69 (s, 3H), 3.42 (s, 3H), 3.66(t, 2H), 3.82(t, 2H), 3.87(s, 3H), 4.21(s, 2H), 4.57(s, 2H), 7.05, 7.07 (d, 2H), 7.34,7.36 (d, 1H), 7.53(s,1H), 7.62, 7.64(d, 2H), 8.195, 8.211 (d, 1H). MH$^+$=530.30, RT =1.94 Min.

EXAMPLE 256

2-chloroethyl 2-chloro-4-((2-(3-(4-methoxyphenyl)-5-methylisoxazole-4-carbonyl)guanidino)methyl)phenylcarbamate

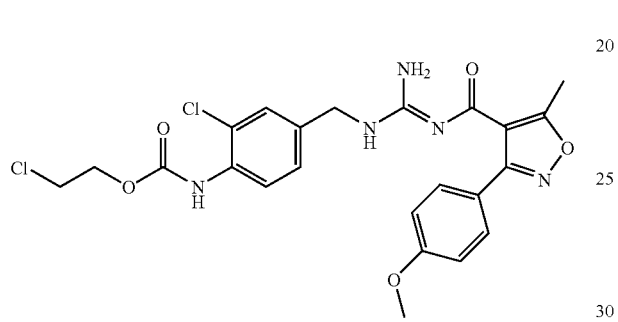

The title compound was prepared by analogy to Example 255. $^1$H NMR (CD$_3$OD): δ 2.69 (s, 3H), 3.82(t, 2H), 3.86(s, 3H), 4.44(t, 2H), 4.55(s, 2H), 7.05, 7.07 (d, 2H), 7.31,7.33 (d, 1H), 7.49(s,1H), 7.61, 7.63(d, 2H), 7.897, 7.914 (d, 1H). MH$^+$=520.24.

EXAMPLES 257 TO 268

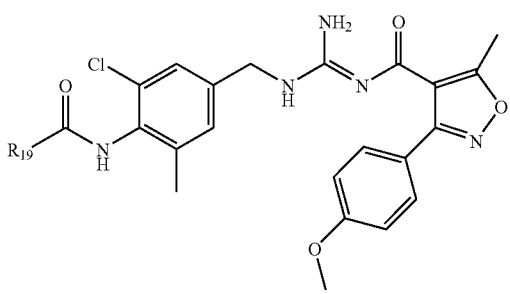

EXAMPLES 257 TO 268 WERE PREPARED BY ANALOGY TO EXAMPLE 148.

| Example | R$_{19}$ | MW | m/z | RT | LC/MS |
|---|---|---|---|---|---|
| 257 | 3-chloro-2-methylpyridin-4-yl | 581.5 | 581 | 1.38 | M |
| 258 | (N,N-dimethylamino)methyl | 513.0 | 513 | 1.21 | M |
| 259 | furan-2-yl | 522.0 | 522 | 1.26 | M |

-continued

| Example | R$_{19}$ | MW | m/z | RT | LC/MS |
|---|---|---|---|---|---|
| 260 | pyridin-2-yl | 533.0 | 533 | 1.33 | M |
| 261 | 2-(methylthio)ethyl | 530.1 | 530 | 1.23 | M |
| 262 | benzothiophen-2-yl | 588.1 | 588 | 1.49 | M |
| 263 | cyclohexyl | 538.1 | 538 | 1.47 | M |
| 264 | cyclopropyl | 496.0 | 496 | 1.22 | M |
| 265 | isobutyl | 512.0 | 512 | 1.32 | M |
| 266 | N-methylpyrrol-2-yl | 535.0 | 535 | 1.35 | M |
| 267 | ethyl | 484.0 | 484 | 1.24 | M |
| 268 | sec-butyl | 512.0 | 512 | 1.31 | M |

EXAMPLES 269 TO 270

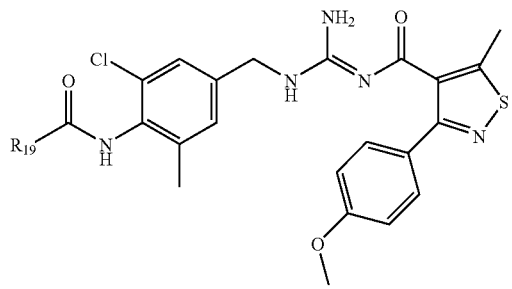

EXAMPLES 269 TO 270 WERE PREPARED BY ANALOGY TO EXAMPLE 149.

| Example | R$_{19}$ | MW | m/z | RT | LC/MS |
|---|---|---|---|---|---|
| 269 | phenyl | 548.1 | 548 | 2.66 | B |
| 270 | propyl | 514.0 | 514 | 2.55 | B |

EXAMPLE 271

(Z)-Propyl 2-chloro-4-((2-(3-(4-methoxyphenyl)-5-methylisoxazole-4-carbonyl)guanidino)methyl)-6-methylphenylcarbamate

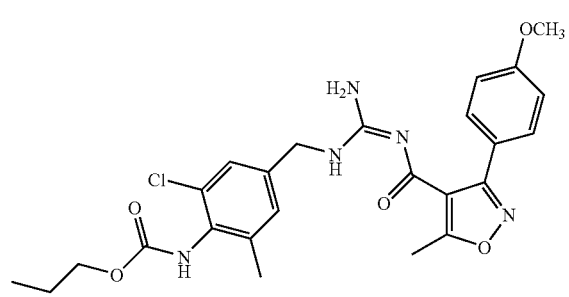

The title compound was prepared by analogy to Example 148, using Preparation AO as the amine.

$^1$H NMR (500 MHz, CDCl$_3$) δ 7.50 (d, J=8.6 Hz, 2 H), 7.13 (s, 1 H), 7.02 (s, 1 H), 6.94 (d, J=8.6 Hz, 2 H), 4.30 (s, 2 H), 4.11 (t, J=6.6 Hz, 2 H), 3.80 (s, 3 H), 2.63 (s, 3 H), 2.30 (s, 3 H), 1.70 (s, br 2 H), 0.96 (s, br, 3 H). MH$^+$=514, RT=2.72 (Method B).

EXAMPLE 272

(Z)-Propyl 2-chloro-4-((2-(3-(4-methoxyphenyl)-5-methylisothiazole-4-carbonyl)guanidino)methyl)-6-methylphenylcarbamate

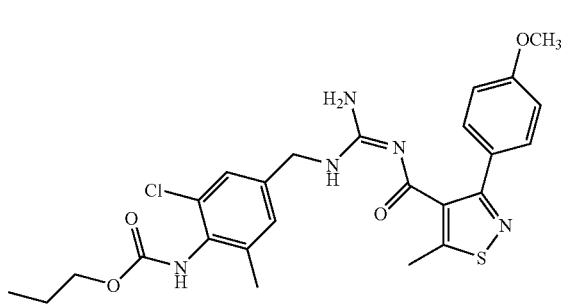

The title compound was prepared by analogy to Example 149, using Preparation AO as the amine. MH$^+$=530, RT=2.73 (Method B).

EXAMPLE 273

(E)-N-((4-amino-3-chloro-5-(pent-1-ynyl)benzylamino)(amino)methylene)-3-(4-methoxyphenyl)-5-methylisothiazole-4-carboxamide

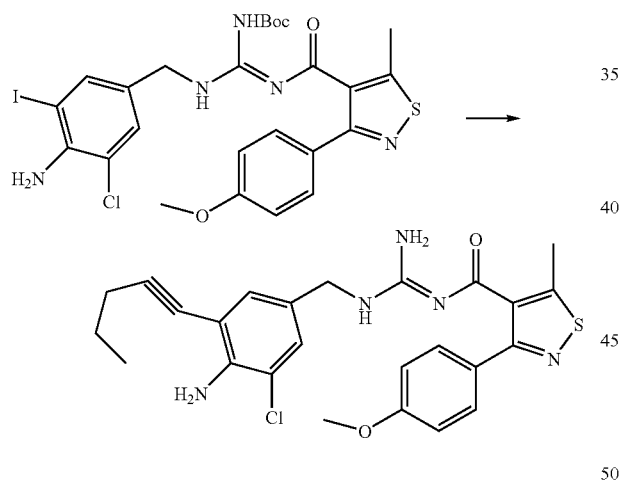

Step 273A. A mixture of (E)-N-((3-chloro-4-amino-5-iodobenzylamino)(amino)methylene)-3-(4-methoxyphenyl)-5-methylisothiazole-4-carboxamide (25 mg, 0.038 mmol), prepared by analogy to Example 149 using Preparation AP as the amine, 1-pentyne (50 mg, 0.735 mmol), dichlorobis(triphenylphosphine)-palladium(II) (8 mg), copper(I) iodide (15 mg), and diethylamine (50 mg) in DMF (2 mL) was stirred for 20 hours. The Boc protected product was obtained by HPLC purification.

Step 273B. The product from Step 273A was treated with 30% TFA in DCM for 1.5 h, desired product (E)-N-((4-amino-3-chloro-5-(pent-1-ynyl)benzylamino) (amino)methylene)-3-(4-methoxyphenyl)-5-methylisothiazole-4-carboxamide was obtained by HPLC purification (5 mg). $^1$H NMR (CD$_3$OD): δ 1.06 (t, 3H), 1.65 (m, 2H), 2.48 (t, 2H), 2.70 (s, 3H), 3.81(s, 3H), 4.36(s, 2H), 6.98, 7.00 (d, 2H), 7.13 (s,1H), 7.19 (s,1H), 7.56,7.58 (d, 2H). MH$^+$=496.16.

EXAMPLE 274

(E)-N-((4-amino-3-chloro-5-cyanobenzylamino)(amino)methylene)-3-(4-methoxyphenyl)-5-methyl-isothiazole-4-carboxamide

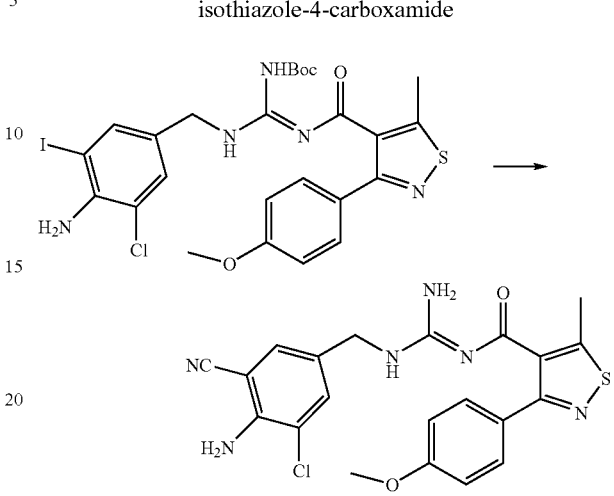

Step 274A. A mixture of (E)-N-((3-chloro-4-amino-5-iodobenzylamino)(amino)methylene)-3-(4-methoxyphenyl)-5-methylisothiazole -4-carboxamide (25 mg, 0.038 mmol), prepared by analogy to Steps 149 using Preparation AP as the amine, zinc cyanide (15 mg, 0.128 mmol), and tetrakis(triphenylphosphine)palladium (6 mg) in DMF (2 mL) was heated at 80° C. overnight. The Boc protected product was obtained by HPLC purification.

Step 275B. The product from Step 274A was treated with 30% TFA in DCM for 1.5 h, desired product (E)-N-((4-amino-3-chloro-5-cyanobenzylamino)(amino)methylene)-3-(4-methoxyphenyl)-5-methylisothiazole-4-carboxamide was obtained by HPLC purification (13 mg). $^1$H NMR (CD$_3$OD): δ 2.73 (s, 3H), 3.85(s, 3H), 4.42(s, 2H), 7.00, 7.02 (d, 2H), 7.39 (s,1H), 7.53 (s,1H), 7.59,7.61 (d, 2H). MH$^+$=455.13.

EXAMPLE 275

(E)-N-(amino(1-(4-amino-3,5-dichlorophenyl)ethylamino)methylene)-3-(4-methoxyphenyl)-5-methyl-isothiazole-4-carboxamide

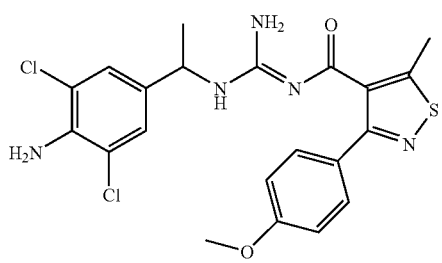

The title compound was prepared by analogy to Example 149, using Preparation AQ as the amine. $^1$H NMR (CD$_3$OD): δ 1.55 (d, 3H), 52.72 (s, 3H), 3.84(s, 3H), 4.78(m, 1H), 6.99, 7.01 (d, 2H), 7.24 (s,2H),7.57,7.59 (d, 2H). MH$^+$=478.14.

EXAMPLE 276

(E)-N-((3-bromo-5-chloro-4-(propylamino)benzylamino)(amino)methylene)-3-(4-methoxyphenyl)-5-methylisothiazole-4-carboxamide

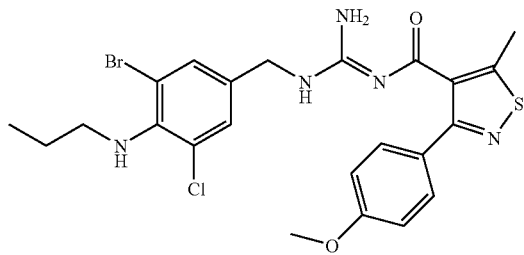

The title compound was prepared by analogy to Example 149, using Preparation AR as the amine. $^1$H NMR (CD$_3$OD): δ 0.995 (t, 3H), 1.62 (m, 2H), 2.73 (s, 3H), 3.35(t,2H), 3.86(s, 3H), 4.48(s, 2H), 7.02, 7.04 (d, 2H), 7.36(s,1H), 7.51 (s,1H), 7.60,7.62 (d, 2H). MH$^+$=550.00,552.00.

EXAMPLE 277

(E)-N-(amino(5-amino-2,3-dihydro-1H-inden-1-ylamino)methylene)-3-(4-methoxyphenyl)-5-methylisothiazole-4-carboxamide

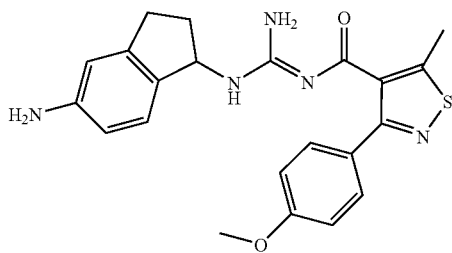

The title compound was prepared by analogy to Example 149, using the intermediate from Step AS2 in Preparation AS as the amine. $^1$H NMR (CD$_3$OD): δ 2.11 (m, 1H), δ 2.74 (s, 3H), 2.77(m, 1H), 3.03(m, 1H), 3.14(m, 1H), 3.87(s, 3H), 5.28(m, 1H), 7.03, 7.05(d, 2H), 7.29 (d,1H),7.32(s, 1H), 7.47 (d, 1H), 7.59,7.61 (d, 2H). MH$^+$=422.13.

EXAMPLE 278

(E)-N-(amino(5-amino-4,6-dibromo-2,3-dihydro-1H-inden-1-ylamino)methylene)-3-(4-methoxyphenyl)-5-methylisothiazole-4-carboxamide

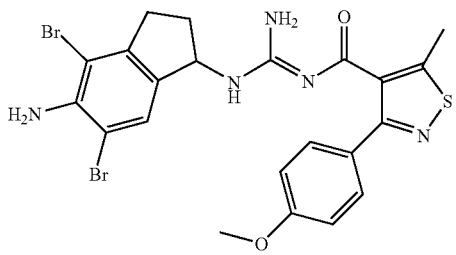

The title compound was prepared by analogy to Example 149, using Preparation AS as the amine. $^1$H NMR (CD$_3$OD): δ 2.01 (m, 1H), δ 2.59 (m, 1H), 2.70(s, 3H), 2.84(m, 1H), 2.99(m, 1H), 3.81(s, 3H), 5.21(m, 1H), 6.99(d, 2H), 7.37 (s, 1H), 7.58(d, 2H). MH$^+$=578.03,580.03.

EXAMPLE 279

(E)-N-((4-acetamido-3,5-dichlorobenzylamino)(amino)methylene)-3-(4-methoxyphenyl)-5-methylisothiazole-4-carboxamide

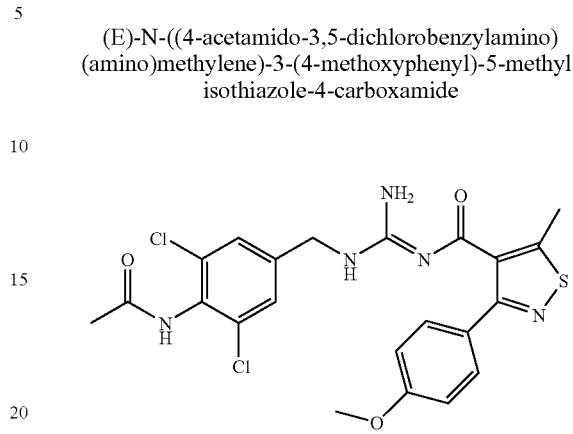

The title compound was prepared by analogy to Example 149, using Preparation AT as the amine. $^1$H NMR ((CD$_3$OD): δ 2.21 (s, 3H), 2.74 (s, 3H), 3.85(s, 3H), 4.60(s, 2H), 7.05 (d, 2H), 7.45 (s,2H), 7.63 (d, 2H). MH$^+$=506.12

Biological Methods

There are a number of methods by which inhibitors of the BACE enzyme can be identified experimentally. The enzyme can be obtained from membrane samples from natural tissues or cultured cells or can be expressed recombinantly in a host cell by well known methods of molecular biology. The whole enzyme or a portion thereof can be expressed, for example, in bacterial, insect or mammalian cells to obtain a catalytically active enzyme species. The enzymatic activity and/or ligand binding capability of the enzyme can be assessed within these membrane samples, or the enzyme can be purified to varying extents. As an illustrative example, the nucleic acid sequence encoding the pro and catalytic domains of human BACE can be appended on the 5' end with an untranslated and signal sequence from the gene for acetylcholinesterase, and on the 3' end with a sequence encoding a poly-histidine tag. This cDNA can then be expressed in *Drosophila melanogaster* S2 cells in which the signal and pro sequences of the transcribed/translated protein are removed by cellular proteases and the catalytic domain, appended by a C-terminal poly-histidine tag, is secreted out into the cellular medium. The enzyme can then be purified from the culture medium by nickel affinity chromatography by methods well known to those trained in the art [Mallender, W. et al., (2001) "Characterization of recombinant, soluble beta-secretase from an insect cell expression system." *Mol. Pharmacol.* 59: 619-626]. Similar strategies for expressing and purifying various forms of BACE in bacterial, mammalian and other cell types would be known to one skilled in the art. A preferred method for determining the potency of a test compound in binding to the BACE enzyme is by monitoring the displacement of a suitable radioligand.

Radioligand displacement assays with a radiolabeled BACE inhibitor (WO 2004 013098, compound 3, where the methoxy group is substituted for C($^3$H)$_3$) were carried out using standard methods (Keen, M. (1999) in *Receptor Binding Techniques* (Walker, J. M. ed) p. 106 Humana Press, Totowa, N.J.). The HEK293-9B.A1 cell line, which overexpresses the BACE1 enzyme, was derived from HEK293 cells (Simmons, N. L. (1990) A cultured human renal epithelioid cell line responsive to vasoactive intestinal peptide. *Exp. Physiol.* 75:309-19.) by RAGE™ (Harrington, J. J. et al. (2001) Creation of genome-wide protein expression libraries using random activation of gene expression. *Nat. Biotechnol.* 19:440-5.; U.S. Pat. Nos. 6,410,266 and 6,361,972). T225 flask cultures of HEK293-9B.A1 were grown to 80% confluency in DMEM supplemented with 2 mM L-glutamine, 10 μg/ml penicillin, 10 μg/ml streptomycin, 3 μg/ml puromycin, 100 nM methotrexate, and 10% fetal bovine serum (Invitrogen, Carlsbad, Calif.), harvested, and resuspended at $2 \times 10^8$ cells per 10 ml of lysis buffer consisting of 50 mM HEPES pH 7.0 containing a protease inhibitor cocktail of AEBSF 104 μM, aprotinin 80 nM, leupeptin 2 μM, bestatin 4 μM, pepstatin A 1.5 μM, and E-64 1.4 μM (0.1% of protease inhibitor cocktail P8340, Sigma-Aldrich, St. Louis, Mo.) at 4° C. The resuspended cells were homogenized using a Polytron (Brinkman, Westbury, N.Y.) at setting 6 for 10 sec., then centrifuged at 48,000×g for 10 min. The resulting pellet was washed by repeating the resuspension, homogenization and centrifugation steps. The final pellet was resuspended in buffer at 4° C. to yield a total protein concentration of 5 mg/ml, then aliquots were frozen in liquid nitrogen for further storage at −70° C. Immediately before carrying out a binding assay, an aliquot of cell homogenate was thawed and diluted to a concentration of 100 μg/ml in assay buffer consisting of 50 mM HEPES pH 5.0 and 0.1% CHAPSO. Assays were initiated in polypropylene 96-well plates (Costar, Cambridge, Mass.) by the addition of 200 μl of cell homogenate to 50 μl of assay buffer containing 1 nM radioligand (WO 2004 013098, compound 3, where the methoxy group is substituted for $C(^3H)_3$: 80 Ci/mMol) and various concentrations of unlabelled compounds, and incubated for 1.5 hr. at 25° C. Separation of bound from free radioligand was by filtration on GFF glass fiber filters (Innotech Biosystems International, Lansing, Mich.) using an Innotech cell harvester. Filters were washed three times with 0.3 ml of phosphate buffered saline pH 7.0 at 4° C. and assessed for radioactivity using a Wallac 1450 Microbeta liquid scintillation counter (PerkinElmer, Boston, Mass.). Ki values of competing compounds were derived through Cheng-Prussoff correction of IC50 values calculated using XLfit (IDBS, Guildford, UK).

Abbreviations

AEBSF: 4-(2-Aminoethyl)benzenesulfonyl fluoride hydrochloride
CHAPSO: 3-[(3-Cholamidopropyl)dimethylammonio]-2-hydroxy-1-propanesulfonate
D-MEM: Dulbecco's modified eagle medium

TABLE 1

HEPES: 4-(2-Hydroxyethyl)piperazine-1-ethanesulfonic acid
RAGE ™: Random Activation of Gene Expression ™
The activity of specific compounds described herein and tested in the above assay is provided in Table 1.

| Compounds of Examples | Activity Rating |
| --- | --- |
| 22 | ++ |
| 132 | ++ |
| 144 | +++ |
| 148 | ++ |
| 149 | +++ |
| 150 | +++ |
| 152 | ++ |
| 153 | +++ |
| 154 | +++ |

TABLE 1-continued

HEPES: 4-(2-Hydroxyethyl)piperazine-1-ethanesulfonic acid
RAGE ™: Random Activation of Gene Expression ™
The activity of specific compounds described herein and tested in the above assay is provided in Table 1.

| Compounds of Examples | Activity Rating |
| --- | --- |
| 168 | ++ |
| 203 | ++ |
| 237 | +++ |
| 279 | +++ |

[a]Activity based on $IC_{50}$ values:
+++ = <0.1 μM
++ = 0.1-1.0 μM

In vitro Assay to Identify β-Secretase Inhibitor Based on the Inhibition of Aβ Formations from Membrane Preparations.

An isolated membrane fraction which contains functionally active β-secretase and β-APP substrates can generate β-secretase cleavage products including Aβ (Roberts, S. B.; Hendrick, J. P.; Vinitsky, A.; Lewis, M.; Smith, D. W.; Pak, R. PCT Publication WO 01/0175435; Fechteler, K.; Kostka, M.; Fuchs, M. Patent Application No. DE 99-19941039; Shearman, M.; Beher, D. et al., *Biochemistry*, 2000, 39, 8698-8704; Zhang, L. Song, L. et al., *Biochemistry* 2001, 40, 5049-5055). An isolated membrane fraction can be prepared from human derived cell lines such as HeLa and H4 which have been transfected with wild type or mutant forms of β-APP or a human alkaline phosphatase β-APP fusion construct, and stably express high levels of β-secretase substrates. The endogenous β-secretase present in the isolated membranes prepared at 0-4° C. cleaves the β-APP substrates when the membranes are shifted from 0-4 to 37° C. Detection of the cleavage products including Aβ can be monitored by standard techniques such as immunoprecipitation (Citron, M.; Diehl, T. S. et al., *Proc. Natl. Acad. Sci. USA*, 1996, 93,13170-13175), western blot (Klafki, H.-W.; Ambramowski, D. et al., *J. Biol. Chem.* 1996, 271, 28655-28659), enzyme linked immunosorbent assay (ELISA) as demonstrated by Seubert, P.; Vigo-Pelfrey, C. et al., *Nature*, 1992, 359, 325-327, or by a preferred method using time-resolved fluorescence of the homogeneous sample containing membranes and Aβ (Roberts, S. B.; Hendrick, J. P.; Vinitsky, A.; Lewis, M.; Smith, D. W.; Pak, R. PCT Publication WO 01/0175435; Shearman, M.; Beher, D. et al., *Biochemistry*, 2000, 39, 8698-8704). The Aβ present in a homogeneous sample containing membranes can be detected by time-resolved fluorescence with two antibodies that recognize different epitopes of Aβ. One of the antibodies recognizes an epitope that is present in Aβ but not present in the precursor fragments; preferably the antibody binds the carboxyl terminus of Aβ generated by the β-secretase cleavage. The second antibody binds to any other epitope present on Aβ. For example, antibodies that bind the N-terminal region (e.g., 26D6-B2-B3 SIBIA Neurosciences, La Jolla, Calif.) or bind the C-terminal end (e.g., 9S3.2® antibody, Biosolutions, Newark, Del.) of the Aβ peptide are known. The antibodies are labeled with a pair of fluorescent adducts that transfer fluorescent energy when the adducts are brought in close proximity as a result of binding to the N- and C-terminal ends or regions of Aβ. A lack of fluorescence is indicative of the absence of cleavage products, resulting from inhibition of β-secretase. The isolated membrane assay can be used to identify candidate agents that inhibit the activity of β-secretase cleavage and Aβ production.

A typical membrane-based assay requires 45 μg membrane protein per well in a 96- or 384-well format. Membranes in a neutral buffer are combined with the test compound and shifted from 0-4 to 37° C. Test agents may typically consist of synthetic compounds, secondary metabolites from bacterial or fungal fermentation extracts, or extracts from plant or marine samples. All synthetic agents are initially screened at doses ranging from 10-100 μM or in the case of extracts at sufficient dilution to minimize cytotoxicity. Incubation of the membranes with the test agent will continue for approximately 90 minutes at which time fluorescence labeled antibodies are added to each well for Aβ quantitation. The time-resolved fluorescence detection and quantitation of Aβ is described elsewhere (Roberts, S. B.; Hendrick, J. P.; Vinitsky, A.; Lewis, M.; Smith, D. W.; Pak, R. PCT Publication WO 01/0175435; Shearman, M.; Beher, D. et al., *Biochemistry*, 2000. 39, 8698-8704). Results are obtained by analysis of the plate in a fluorescence plate reader and comparison to the mock treated membranes and samples in which known amounts of Aβ were added to construct a standard concentration curve. A positive acting compound is one that inhibits the AP relative to the control sample by at least 50% at the initial tested concentration. Compounds of the present application are considered active when tested in the above assay if the $IC_{50}$ value for the test compound is less than 50 μM. A preferred $IC_{50}$ value is less than 1 μM. A more preferred $IC_{50}$ value is less than 0.1 μM. If a compound is found to be active then a dose response experiment is performed to determine the lowest dose of compound necessary to elicit the inhibition of the production of Aβ.

In Vivo Assays for the Determination of Aβ Reduction by a β-Secretase Inhibitor.

In vivo assays are available to demonstrate the inhibition of P-secretase activity. In these assays, animals, such as mice, that express normal levels of APP, β- and γ-secretase or are engineered to express higher levels of APP and hence Aβ can be used to demonstrate the utility of β-secretase inhibitors, as demonstrated with γ-secretase inhibitors [Dovey, H. et al., (2001), J. Neurochem. 76: 173-181]. In these assays, β-secretase inhibitors are administered to animals and Aβ levels in multiple compartments, such as plasma, cerebral spinal fluid, and brain extracts, are monitored for Aβ levels using methods previously outlined. For instance, Tg2576 mice, which overexpress human APP, are administered β-secretase inhibitors by oral gavage at doses that will cause measurable Aβ lowering, typically less than 100 mg/kg. Three hours after dosing plasma, brain, and CSF are collected, frozen in liquid nitrogen, and stored at −80° C. until analysis. For Aβ detection, plasma is diluted 15-fold in PBS with 0.1% Chaps while CSF is diluted 15-fold in 1% Chaps with protease inhibitors (5 μg/ml leupeptin, 30 μg/ml aprotinin, 1 mM phenylmethylsulfonylfluoride, 1 μM pepstatin). Brains are homogenized in 1% Chaps with protease inhibitors using 24 ml solution/g brain tissue. Homogenates were then centrifuged at 100,000×g for 1 hr at 4° C. The resulting supernatants were then diluted 10-fold in 1% Chaps with protease inhibitors. Aβ levels in the plasma, CSF, and brain lysate can then be measured using time-resolved fluorescence of the homogenous sample or one of the other methods previously described.

A β-secretase inhibitor is considered active in one of the above in vivo assays if it reduces Aβ by at least 50% at a dosage of 100 mg/kg.

Dosage and Formulation

The compounds of the present application can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present application can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed to prevent or treat neurological disorders related to β-amyloid production or accumulation, such as Alzheimer's disease and Down's Syndrome.

The compounds of this application can be administered by any means that produces contact of the active agent with the agent's site of action in the body of a host, such as a human or a mammal., They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present application will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

Advantageously, compounds of the present application may be administered in a single daily dose, or the total daily dosage may be administered in divided doses of two, three, or four times daily.

The compounds for the present application can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present application, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or β-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present disclosure can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present disclosure may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palmitoyl residues. Furthermore, the compounds of the present disclosure may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

What is claimed is:

1. A compound of Formula (I); or a stereoisomer thereof

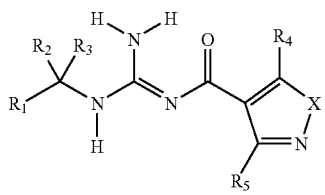

wherein
$R_1$ is naphthyl optionally substituted with halogen, quinolyl, thienyl, 2,3-dimethyl-1H-indol-5-yl, or phenyl in which said phenyl is optionally substituted with one or more groups selected from halogen, CN, $CF_3$, OH, —$NH_2$, $C_{3-6}$cycloalkyl, $C_{1-6}$alkoxy, $OR_{21}$, $C_{1-6}$alkyl optionally substituted with OH or —$NH_2$, —$(CH_2)_m$—NHC(=O)$OR_{17}$, —$(CH_2)_m$—NHC(=O)Ophenyl optionally substituted with halogen, —$(CH_2)_m$—NHC(=O)$R_{18}$, —NH(C=O)$R_{19}$, —$CH_2NH(SO_2)R_{20}$, $R_{22}$, $R_{23}$, and —$CH_2$morpholino;

$R_2$ and $R_3$ are each independently hydrogen, methyl or hydroxymethyl;

$R_4$ is hydrogen, $C_{1-6}$alkyl optionally substituted with $C_{1-4}$alkoxy or thiomethyl; or phenyl optionally substituted with one or more groups selected from halogen, $C_{1-4}$alkyl, $C_{1-4}$alkoxy, nitro and dimethylamino;

$R_5$ is phenyl in which said phenyl is optionally substituted with one or more groups selected from halogen, —$S(O)_2$methyl, $C_{1-4}$alkyl and $C_{1-4}$alkoxy;

X is O, S, NH or $NHCH_3$;

m is 0 or 1;

$R_{17}$ is $C_{1-6}$ alkyl optionally substituted with $C_{1-4}$alkoxy, halogen, $C_{2-3}$alkynyl, 4-nitrophenyl, benzyloxy or benzothiophene 1,1-dioxide;

$R_{18}$ is $C_{1-6}$alkyl or $C_{3-6}$cycloalkyl in which each is optionally substituted with a group selected from halogen, CN, $CF_3$, —$N(CH_3)_2$, $C_{1-4}$alkoxy, $C_{3-6}$cycloalkyl, morpholino, thienyl, imidazolyl, pyridyl, azepinyl, benzothienyl, benzofuranyl, phenyl and methoxyphenyl;

$R_{19}$ is $C_{1-6}$alkyl optionally substituted with methoxyethyloxy or methylthio; $C_{1-4}$alkoxy optionally substituted with halogen; $C_{3-6}$cycloalkyl, phenyl, pyridyl optionally substituted with one or two halogen and $C_{1-4}$alkyl; benzothienyl, 1-methyl-2-pyrrolyl or furanyl;

$R_{20}$ is $C_{1-6}$alkyl, 1,2-dimethyl-1H-imidazolyl, thienyl or phenyl in which said phenyl is optionally substituted with a group selected from acetyl, $C_{1-4}$alkoxy, benzyloxy, halogen, NH(C=O)$CH_3$ and nitro;

$R_{21}$ is $C_{1-6}$alkyl optionally substituted with a group selected from $C_{1-4}$alkoxy, halogen, phenyl, furanyl and methylamino;

$R_{22}$ is —CH=CH-phenyl or —CH=CH—$C_{1-4}$alkyl optionally substituted with $C_{1-4}$alkoxy or OH; and $R_{23}$ is pyridyl, thienyl, $C_{2-6}$alkenyl, or phenyl optionally substituted with halogen;

or a nontoxic pharmaceutically acceptable salt thereof.

2. The compound according to claim 1 of Formula (I); or a stereoisomer thereof,

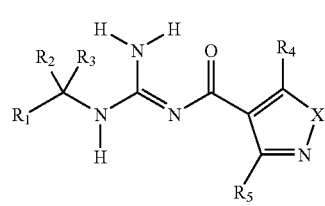

wherein
$R_1$ is naphthyl optionally substituted with halogen, quinolyl, thienyl, 2,3-dimethyl-1H-indol-5-yl, or phenyl in which said phenyl is optionally substituted with one or more groups selected from halogen, CN, $CF_3$, OH, —$NH_2$, $C_{3-6}$cyclalkyl, $C_{1-6}$alkoxy, $OR_{21}$, $C_{1-6}$alkyl optionally substituted with OH or —NH$_2$, —(CH$_2$)$_m$—NHC(=O)OR$_{17}$, —(CH$_2$)$_m$—NHC(=O)Ophenyl optionally substituted with halogen, —(CH$_2$)$_m$—NHC(=O)R$_{18}$, —NH(C=O)R$_{19}$, —CH$_2$NH(SO$_2$)R$_{20}$, R$_{22}$, R$_{23}$, and —CH$_2$morpholino;

R$_2$ and R$_3$ are each hydrogen;

R$_4$ is C$_{1-6}$alkyl optionally substituted with C$_{1-4}$alkoxy or thiomethyl;

R$_5$ is phenyl optionally substituted with one or more groups selected from halogen, C$_{1-4}$alkyl, —S(O)$_2$methyl and C$_{1-4}$alkoxy;

X is O, S, or NH;

m is 0 or 1;

R$_{17}$ is C$_{1-4}$alkoxy, halogen, C$_{2-3}$alkynyl, 4-nitrophenyl, benzyloxy or benzothiophene 1,1-dioxide;

R$_{18}$ is C$_{1-6}$alkyl or C$_{3-6}$cycloalkyl in which each is optionally substituted with a group selected from halogen, CN, CF$_3$, —N(CH$_3$)$_2$, C$_{1-4}$alkoxy, C$_{3-6}$cycloalkyl, morpholino, thienyl, imidazolyl, pyridyl, azepinyl, benzothienyl, benzofuranyl, phenyl and methoxyphenyl;

R$_{19}$ is C$_{1-6}$alkyl optionally substituted with methoxyethyloxy or methylthio; C$_{1-4}$alkoxy optionally substituted with halogen; C$_{3-6}$cycloalkyl, phenyl, pyridyl optionally substituted with one or two halogen and C$_{1-4}$alkyl; benzothienyl, 1-methyl-2-pyrrolyl or furanyl;

R$_{20}$ is C$_{1-6}$alkyl, 1,2-dimethyl-1H-imidazolyl, thienyl or phenyl in which said phenyl is optionally substituted with a group selected from acetyl, C$_{1-4}$alkoxy, benzyloxy, halogen, NH(C=O)CH$_3$ and nitro;

R$_{21}$ is C$_{1-6}$alkyl optionally substituted with a group selected from C$_{1-4}$alkoxy, halogen, phenyl, furanyl and methylamino; R$_{22}$ is —CH=CH-phenyl or —CHCH—C$_{1-4}$alkyl optionally substituted with C$_{1-4}$alkoxy or OH; and R$_{23}$ is pyridyl, thienyl, C$_{2-6}$alkenyl, or phenyl optionally substituted with halogen;

or a nontoxic pharmaceutically acceptable salt thereof.

3. The compound according to claim 2 of Formula (I); or a stereoisomer thereof,

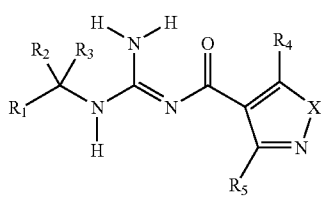

wherein

R$_1$ is phenyl optionally substituted with one or more groups selected from halogen, CN, CF$_3$, OH, —NH$_2$, C$_{3-6}$cycloalkyl, C$_{1-6}$alkoxy, OR$_{21}$, C$_{1-6}$alkyl optionally substituted with OH or —NH$_2$, —(CH$_2$)$_m$—NHC(=O)OR$_{17}$, —(CH$_2$)$_m$—NHC(=O)Ophenyl optionally substituted with halogen, —(CH$_2$)$_m$—NHC(=O)R$_{18}$, —NH(C=O)R$_{19}$, —CH$_2$NH(SO$_2$)R$_{20}$, R$_{22}$, R$_{23}$, and —CH$_2$morpholino;

R$_2$ and R$_3$ are hydrogen;

R$_4$ is C$_{1-3}$alkyl;

R$_5$ is phenyl optionally substituted with one or more groups selected from halogen, C$_{1-4}$alkyl, —S(O)$_2$methyl and C$_{1-4}$alkoxy;

X is O or S;

m is 0 or 1;

R$_{17}$ is C$_{1-4}$alkoxy, halogen, C$_{2-3}$alkynyl, 4-nitrophenyl, benzyloxy or benzothiophene 1,1-dioxide;

R$_{18}$ is C$_{1-6}$alkyl or C$_{3-6}$cycloalkyl in which each is optionally substituted with a group selected from halogen, CN, CF$_3$, —N(CH$_3$)$_2$, C$_{1-4}$alkoxy, C$_{3-6}$cycloalkyl, morpholino, thienyl, imidazolyl, pyridyl, azepinyl, benzothienyl, benzofuranyl, phenyl and methoxyphenyl;

R$_{19}$ is C$_{1-6}$alkyl optionally substituted with methoxyethyloxy or methylthio; C$_{1-4}$alkoxy optionally substituted with halogen; C$_{3-6}$cycloalkyl, phenyl, pyridyl optionally substituted with one or two halogen and C$_{1-4}$alkyl; benzothienyl, 1-methyl-2-pyrrolyl or furanyl;

R$_{20}$ is C$_{1-6}$alkyl, 1,2-dimethyl-1H-imidazolyl, thienyl or phenyl in which said phenyl is optionally substituted with a group selected from acetyl, C$_{1-4}$alkoxy, benzyloxy, halogen, NH(C=O)CH$_3$ and nitro;

R$_{21}$ is C$_{1-6}$alkyl optionally substituted with a group selected from C$_{1-4}$alkoxy, halogen, phenyl, furanyl and methylamino;

R$_{22}$ is —CH=CH-phenyl or —CH=CH—C$_{1-4}$alkyl optionally substituted with C$_{1-4}$alkoxy or OH; and R$_{23}$ is pyridyl, thienyl, C$_{2-6}$alkenyl, or phenyl optionally substituted with halogen;

or a nontoxic pharmaceutically acceptable salt thereof.

4. The compound according to claim 3 of Formula (Ib); or a stereoisomer thereof,

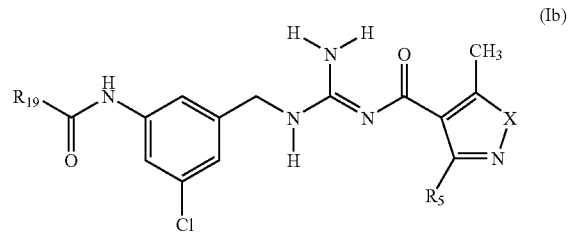

wherein

R$_5$ is phenyl optionally substituted with one or more groups selected from halogen, C$_{1-4}$alkyl, and C$_{1-4}$alkoxy;

X is O or S; and

R$_{19}$ is C$_{1-6}$alkyl optionally substituted with methoxyethyloxy or methylthio; C$_{1-4}$alkoxy optionally substituted with halogen; C$_{3-6}$cycloalkyl, phenyl, pyridyl optionally substituted with one or two halogen and C$_{1-4}$alky; benzothienyl, 1-methyl-2-pyrrolyl or furanyl;

or a nontoxic pharmaceutically acceptable salt thereof.

5. The compound according to claim 3 of Formula (1c); or a stereoisomer thereof,

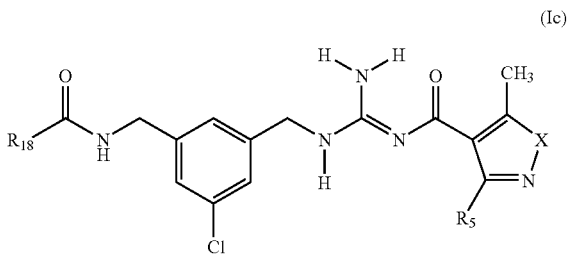

wherein

R$_5$ is phenyl optionally substituted with one or more groups selected from halogen, C$_{1-4}$alkyl and C$_{1-4}$alkoxy;

X is O or S; and

R$_{18}$ is C$_{1-6}$alkyl or C$_{3-6}$cycloalkyl in which each is optionally substituted with a group selected from halogen, CN, CF$_3$, —N(CH$_3$)$_2$, C$_{1-4}$alkoxy, C$_{3-6}$cycloalkyl, morpholino, thienyl, imidazolyl, pyridyl, azepinyl, benzothienyl, benzofuranyl, phenyl and methoxyphenyl;

or a nontoxic pharmaceutically acceptable salt thereof.

6. The compound according to claim 3 of Formula (Id); or a stereoisomer thereof,

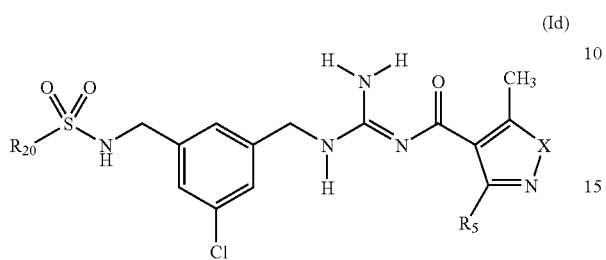

(Id)

wherein
R$_5$ is optionally substituted with one or more groups selected from halogen, C$_{1-4}$alkyl and C$_{1-4}$alkoxy;
X is O or S; and
R$_{20}$ is C$_{1-6}$alkyl, 1,2-dimethyl-1H-imidazolyl, thienyl or phenyl in which said phenyl is optionally substituted with a group selected from acetyl, C$_{1-4}$alkoxy, benzyloxy, halogen, NH(C═O)CH$_3$ and nitro;
or a nontoxic pharmaceutically acceptable salt thereof.

7. The compound according to claim 3 of Formula (Ie); or a stereoisomer thereof,

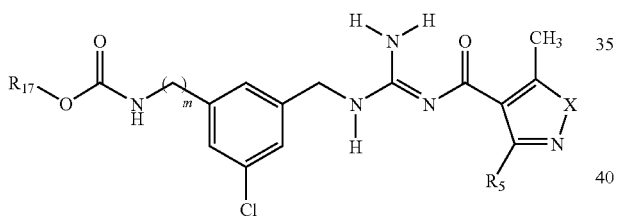

(Ie)

wherein
R$_5$ is phenyl optionally substituted with one or more groups selected from halogen, C$_{1-4}$alkyl and C$_{1-4}$alkoxy;
X is O or S;
m is 0 or 1; and
R$_{17}$ is C$_{1-4}$alkyl optionally substituted with C$_{1-4}$alkoxy, halogen, C$_{2-3}$alkynyl, 4-nitrophenyl, benzyloxy or benzothiophene 1,1-dioxide;
or a nontoxic pharmaceutically acceptable salt thereof 8. The compound according to claim 3 of Formula (Ih); or a stereoisomer thereof,

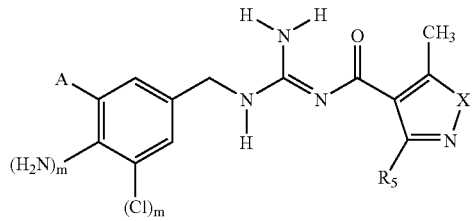

(Ih)

wherein
R$_5$ is phenyl optionally substituted with one or more groups selected from halogen, C$_{1-4}$alkyl and C$_{1-4}$alkoxy;
A is R$_{22}$ or R$_{23}$;
m is 0 or 1;
X is O or S;
R$_{22}$ is —CH═CH-phenyl, —CH═CH—C$_{1-4}$alkyl optionally substituted with C$_{1-4}$alkoxy or OH; and
R$_{23}$ is pyridyl, thienyl, C$_{2-6}$alkenyl, or phenyl optionally substituted with halogen;
or a nontoxic pharmaceutically acceptable salt thereof.

9. A pharmaceutical composition comprising a therapeutically effective amount of a compound of claim 1 in association with a pharmaceutically acceptable adjuvant, carrier or diluent.

10. A compound of the following formula; or a stereoisomer thereof:

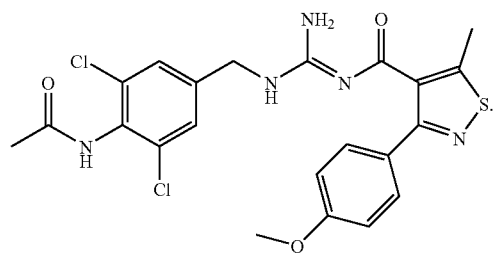

11. A pharmaceutical composition comprising a therapeutically effective amount of a compound of claim 10 in association with a pharmaceutically acceptable adjuvant, carrier or diluent.

* * * * *